(12) United States Patent
Kim et al.

(10) Patent No.: US 11,091,802 B2
(45) Date of Patent: *Aug. 17, 2021

(54) NUCLEIC ACID COMPLEX PAIR AND TARGET DETECTION METHOD USING THEREOF

(71) Applicant: Multilex, Inc., Seoul (KR)

(72) Inventors: Yong Tae Kim, Sejong-si (KR); Jun Hye Moon, Gyeonggi-do (KR)

(73) Assignee: MULTILEX, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/045,566

(22) Filed: Jul. 25, 2018

(65) Prior Publication Data

US 2019/0330679 A1    Oct. 31, 2019

Related U.S. Application Data

(60) Provisional application No. 62/536,898, filed on Jul. 25, 2017, provisional application No. 62/580,335, filed on Nov. 1, 2017.

(30) Foreign Application Priority Data

Jan. 19, 2018  (KR) ......................... 10-2018-0007355
Feb. 6, 2018   (KR) ......................... 10-2018-0014739

(51) Int. Cl.
  *C12Q 1/686*    (2018.01)
  *C12Q 1/6876*   (2018.01)
  *C12Q 1/6853*   (2018.01)

(52) U.S. Cl.
  CPC ........... *C12Q 1/686* (2013.01); *C12Q 1/6853* (2013.01); *C12Q 1/6876* (2013.01); *C12Q 2527/101* (2013.01); *C12Q 2565/1015* (2013.01); *C12Q 2565/60* (2013.01); *C12Q 2600/16* (2013.01); *C12Q 2600/166* (2013.01)

(58) Field of Classification Search
  CPC .............................. C12Q 1/686; C12Q 1/6876
  See application file for complete search history.

(56) References Cited

U.S. PATENT DOCUMENTS

| | | |
|---|---|---|
| 7,799,522 B2 | 9/2010 | Li et al. |
| 2002/0197611 A1 | 12/2002 | Chagovetz |
| 2007/0026429 A1 | 2/2007 | Livak et al. |
| 2008/0064033 A1 | 3/2008 | Haner et al. |
| 2010/0129792 A1 | 5/2010 | Makrigiorgos |
| 2011/0207131 A1 | 8/2011 | Fu |
| 2012/0052502 A1 | 3/2012 | Li |
| 2013/0323738 A1 | 12/2013 | Tanner et al. |

FOREIGN PATENT DOCUMENTS

| | | |
|---|---|---|
| EP | 2789689 A1 | 10/2014 |
| GB | 2512631 A | 10/2014 |
| KR | 1020120021262 A | 3/2012 |
| KR | 1020130008283 A | 1/2013 |
| WO | 2014135872 A1 | 9/2014 |
| WO | 2017106777 A1 | 6/2017 |

OTHER PUBLICATIONS

Li, Anti-primer quenching-based real-time PCR for simplex or multiplex DNA quantification and single-nucleotide polymorphism genotyping, Nature Protocols, 2(1):50-58, 2007. (Year: 2007).*
Huang, Q. et al., "Multiplex Fluorescence Melting Curve Analysis for Mutation Detection with Dual-Labeled, Self-Quenched Probes", PLoS ONE, vol. 6, issue 4, 2011, 9 pages.
Hur, D. et al., "Detection of genetic variation using dual-labeled peptide nucleic acid (PNA) probe-based melting point analysis", Biological Procedures Online, 2015, 17:14, 12 pages.
International Search Report and Written Opinion for PCT Application No. PCT/KR2018/008444, dated Jan. 31, 2019, 8 pages.
Kandimalla, E.R. et al., "'Cyclicons' as Hybridization-Based Fluorescent Primer-Probes: Synthesis, Properties and Application in Real-Time PCR", Bioorganic & Medicinal Chemistry 8, 2000, pp. 1911-1916.
Navarro, E. eet al., "Real-time PCR detection chemistry", Clinica Chimica Acta 439, 2015, pp. 231-250.
Notice of Allowance for Korean Patent Application No. 10-2018-0007355, dated Jun. 26, 2018, 7 pages.
Notice of Allowance for Korean Patent Application No. 10-2018-0014739, dated Jun. 26, 2018, 7 pages.
Office Action for Korean Patent Application No. 10-2018-0007355, dated Mar. 20, 2018, 13 pages.
Office Action for Korean Patent Application No. 10-2018-0014739, dated Mar. 20, 2018, 11 pages.
Office Action for Korean Patent Application No. 10-2018-0086860, dated Aug. 16, 2019, 11 pages.
Office Action for Korean Patent Application No. 10-2018-0097144, dated Aug. 16, 2019, 10 pages.

(Continued)

*Primary Examiner* — Samuel C Woolwine
*Assistant Examiner* — Carolyn L Greene
(74) *Attorney, Agent, or Firm* — Perkins Coie LLP

(57) ABSTRACT

The present invention relates to a nucleic acid complex pair for detecting a target nucleic acid in a sample, and more particularly to a nucleic acid complex pair used for detecting a target DNA in a sample, wherein the nucleic acid complex pair includes a first nucleic acid complex including a first determination region, a first pairing region, and a first detection region; and a second nucleic acid complex including a second determination region, a second paring region, and a second detection region, wherein the first determination region includes at least a partial domain that complementarily binds to a first target nucleic acid sequence, and the second determination region includes at least a partial domain that complementarily binds to a second target nucleic acid sequence, wherein the first pairing region and the second pairing region a domain where they can complementarily hybridize to each other.

17 Claims, 31 Drawing Sheets

Specification includes a Sequence Listing.

(56) References Cited

OTHER PUBLICATIONS

Office Action for Korean Patent Application No. 10-2018-0097145, dated Aug. 18, 2019, 11 pages.
Office Action for Korean Patent Application No. 10-2018-0097146, dated Aug. 18, 2019, 10 pages.
Office Action for Korean Patent Application No. 10-2018-0097147, dated Aug. 19, 2019, 10 pages.
Olivier, M., "The Invader assay for SNP genotyping", Mutation Research 573, 2005, pp. 103-110.
Notice of Allowance for Korean Patent Application No. 10-2018-0086860, dated Jun. 5, 2020, 3 pages.
Notice of Allowance for Korean Patent Application No. 10-2018-0097144, dated Jun. 5, 2020, 3 pages.
Extended European Search Report dated Mar. 31, 2021 for European Patent Application No. 18839013.2 (9 pages).
Kim, Yong-Tae, et al., "Simultaneous Detection of Multiple Pathogenic Targets with Stem-Tagged Primer Sets", ChemBioChem, vol. 21, No. 8, pp. 1116-1120, 2020.
Kim, Yong-Tae, et al., "Simultaneous Genotyping of Multiple Somatic Mutations by Using a Clamping PNA and DNA Detection Probes", ChemBioChem, vol. 16, Issue 2, pp. 209-213, 2014.
Luo, Weihao, et al., "Melting temperature of molecular beacons as an indicator of the ligase detection reaction for multiplex detection of point mutations", Analytical Methods, vol. 7, No. 10, pp. 4225-4230, 2015.
Notice of Allowance dated Feb. 4, 2021 for U.S. Appl. No. 16/752,277 (11 pages).
Office Action dated Feb. 1, 2021 for Canadian Patent Application No. 3,071,088 (4 pages).
Notice of Final Rejection for Korean Patent Application No. 10-2018-0097146, dated Aug. 31, 2020 (3 pages).
Non-Final Office Action dated Jun. 10, 2020 for U.S. Appl. No. 16/752,277 (18 pages).
Final Office Action dated Nov. 10, 2020 for U.S. Appl. No. 16/752,277, filed Jan. 24, 2020 (16 pages).
Grant of Patent dated Mar. 27, 2020 for Korean Patent Application No. 10-2018-0097145 (2 pages).
Grant of Patent dated Mar. 27, 2020 for Korean Patent Application No. 10-2018-0097147 (2 pages).

\* cited by examiner

FIG. 3
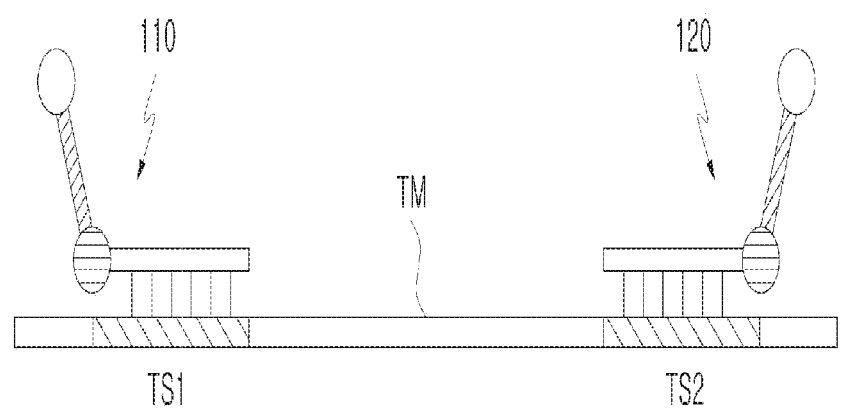
(a)
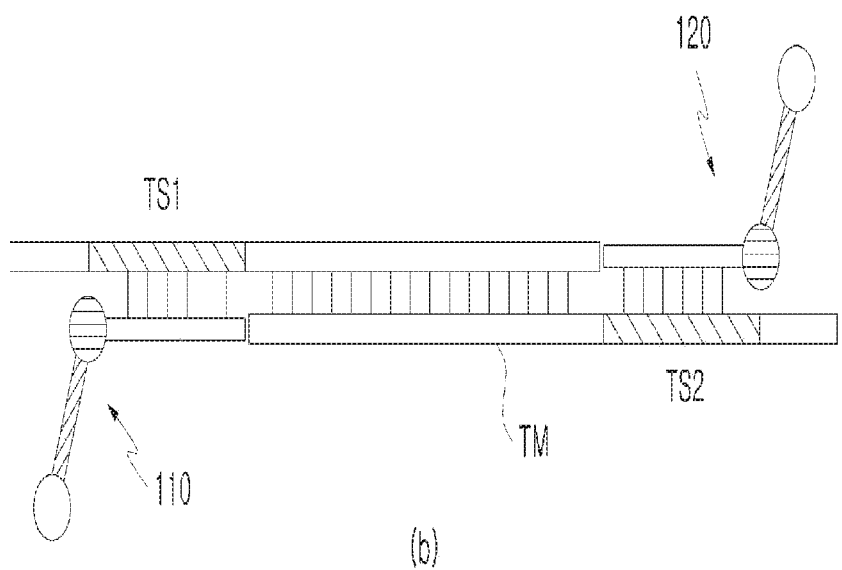
(b)

FIG. 4
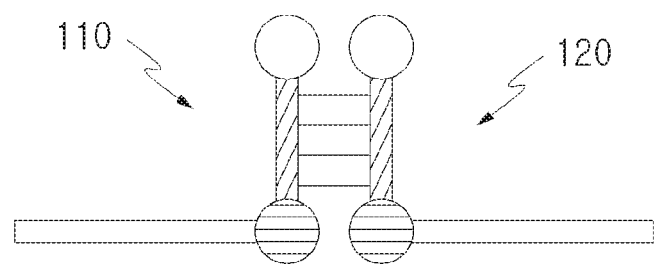
(a)
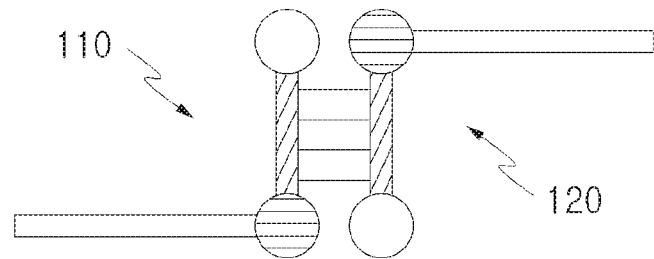
(b)

FIG. 5
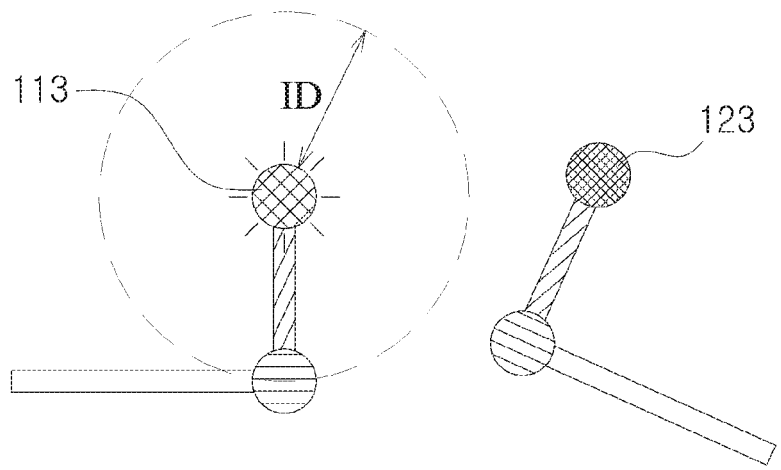
(a)
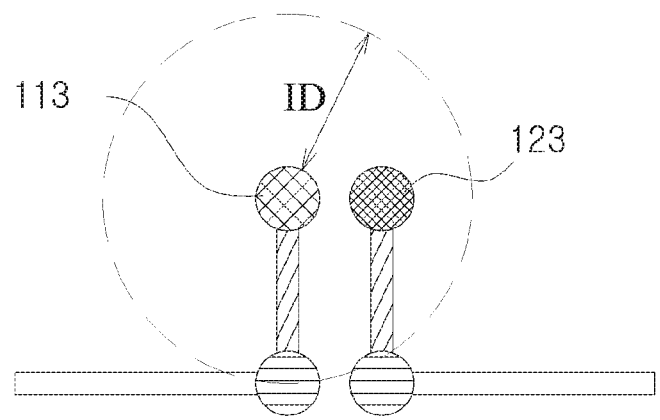
(b)
⊗ : FLUORESCENCE    ⊛ : QUENCHER
    MATERIAL

FIG. 8
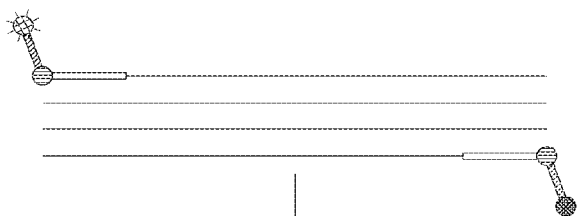
STEP OF HEAT DENATURATION
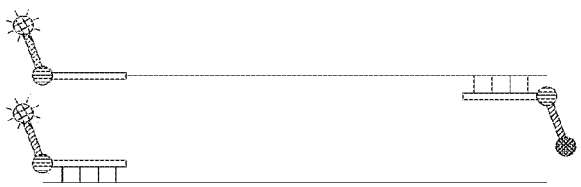
STEP OF ANNEALING
○ : FLUORESCENCE MATERIAL
● : QUENCHER
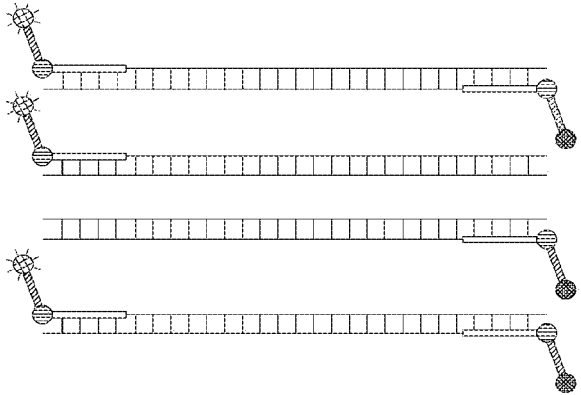
STEP OF POLYMERIZATION FIG. 10
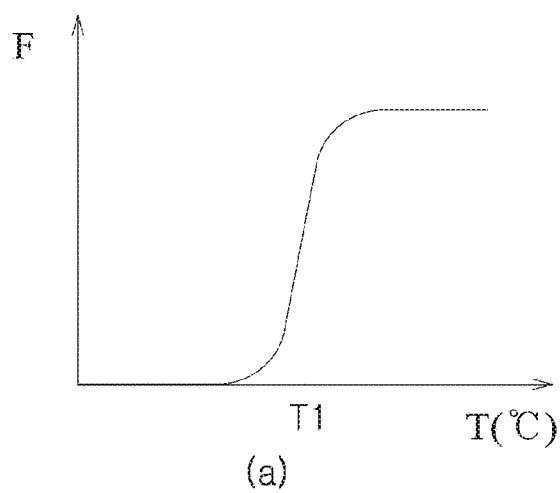
(a)
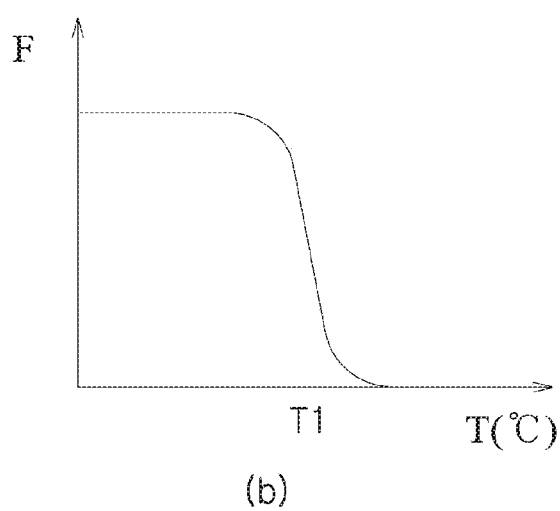
(b)

FIG. 11
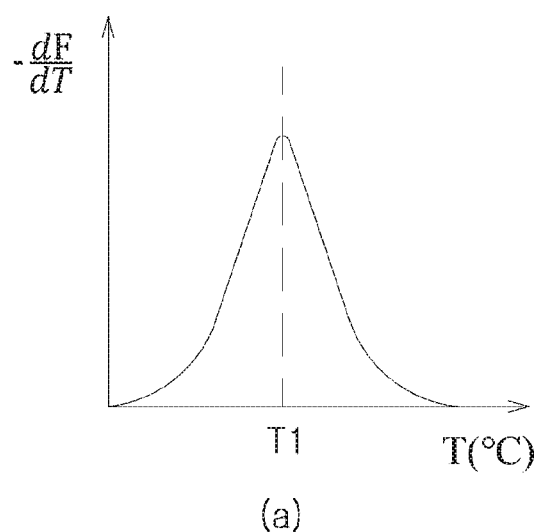
(a)
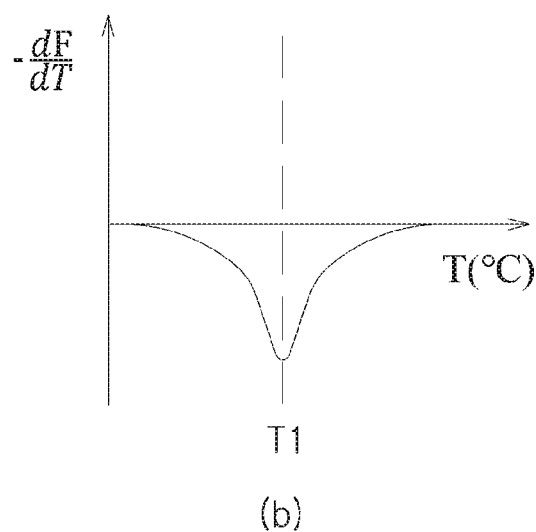
(b)

FIG. 12
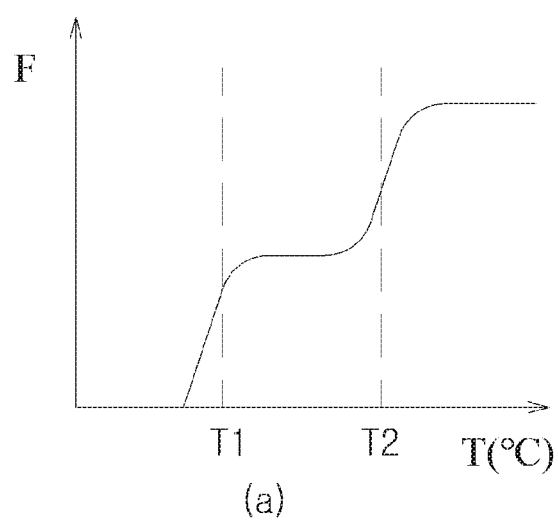
(a)
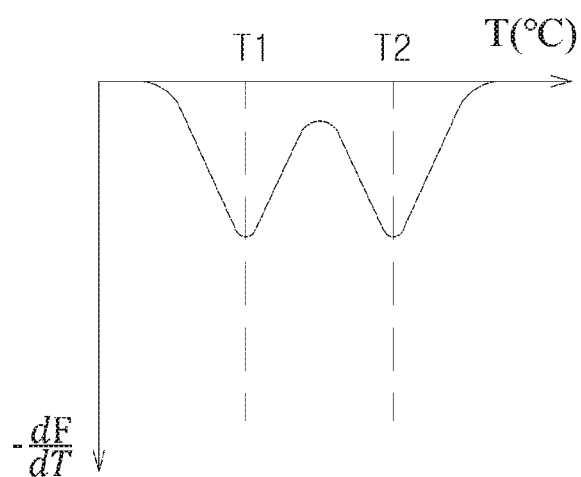
(b)

FIG. 14
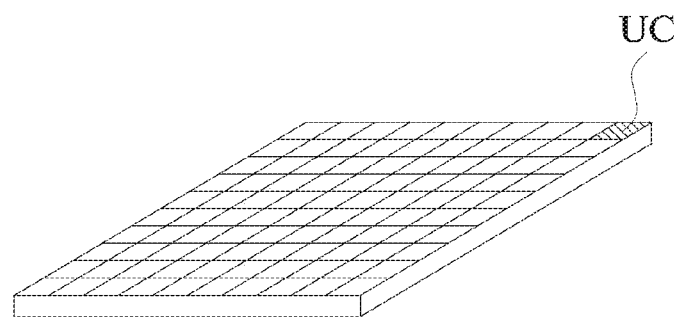
(a)
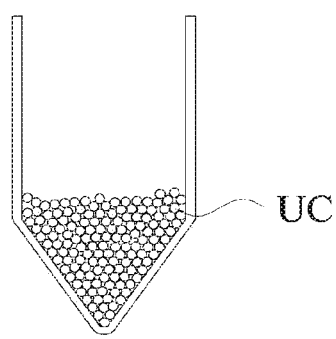
(b)

FIG. 16
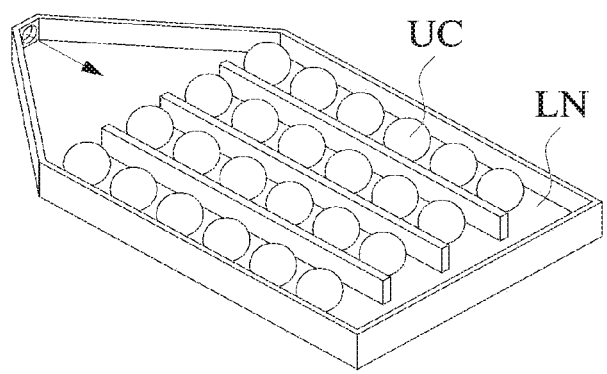
(a)
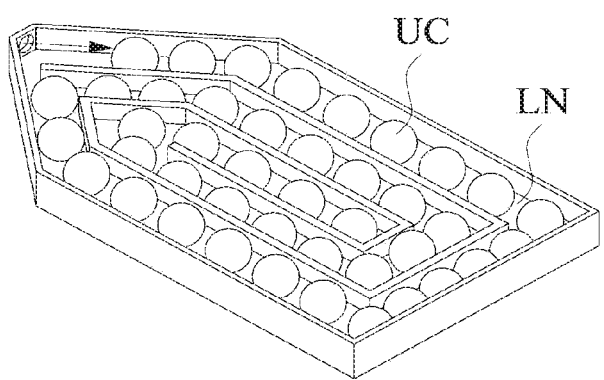
(b)

SEQUENCE LISTING

<160> NUMBER OF SEQ ID NOS: 19

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
agctcctatt gccaacgta                                                19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gtgtggagca tcttgtaatc                                               20

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic probe

<400> SEQUENCE: 3
cactcatata cagc                                                     14

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
tgaagttgaa gcaaatgcac g                                             21

<210> SEQ ID NO 5
<211> LENGTH: 23
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 5
tctgaagttt taccatcaac tgc                                          23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
actacgcaat catcagccaa agc                                          23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaaactctgc gactccaaat tta                                          23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agaagctgat tgttctagtc aat                                          23

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
ttctaaatca ttaaaatcaa cagc                                         24

<210> SEQ ID NO 10
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 cccgcgcg                                                            8

<210> SEQ ID NO 11
<211> LENGTH: 19
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 11
tggagataca cctacattg                                              19

<210> SEQ ID NO 12
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 cgcgcggg                                                           8

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gctggaccat ctatttcatc                                             20

<210> SEQ ID NO 14
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 aaaaaaaa                                                           8

<210> SEQ ID NO 15
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 tttttttt                                                           8

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aaaaaaaaaa                                                        10

<210> SEQ ID NO 17
<211> LENGTH: 10
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 17
tttttttttt                                                          10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aaccttggga                                                          10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tcccaaggtt                                                          10
```

NUCLEIC ACID COMPLEX PAIR AND TARGET DETECTION METHOD USING THEREOF

CROSS-REFERENCE TO RELATED APPLICATIONS

This application claims the benefit of U.S. provisional Applications No. 62/536,898 filed on Jul. 25, 2017, No. 62/580,335 filed on Nov. 1, 2017 in United States Patent & Trademarks Office and Korean Patent Applications No. 10-2018-0007355, filed on Jan. 19, 2018 and No. 10-2018-0014739 filed on Feb. 6, 2018 in the Korean Intellectual Property Office, the disclosure of which is incorporated herein in its entirety by reference.

SEQUENCE LISTING

The instant application contains a Sequence Listing which has been filed electronically in ASCII format and is hereby incorporated by reference in its entirety. Said ASCII copy, created on May 29, 2019, is named 128205-8001_US01_SL.txt and is 4,802 bytes in size.

BACKGROUND

1. Field of the Invention

The present invention relates to a nucleic acid complex pair, and more specifically to a nucleic acid complex pair which can complementary bind to each other and thereby can simultaneously perform the functions of a primer and a probe.

2. Description of the Related Art

Molecular diagnostics is a field of diagnosing diseases by analyzing genes and it currently shows the highest growth among in vitro diagnostics. In fact, with the wide spread of new types of viruses that are presumed to be resulted from environmental pollution and rapid changes in climate, a lot of research on molecular diagnostics are being continued because highest diagnostic accuracy can be secured among in vitro diagnostics and that there is an advantage of enabling a rapid identification of an infection when a new virus emerges.

In the field of molecular diagnostics, DNA sequencing and polymerase chain reaction (hereinafter, PCR) are mainly used. At present, the cost of equipment to perform DNA sequencing is still very high, and the equipment does not enable rapider detection of a target than PCR. Therefore, in most of the small- and medium sized hospitals, large hospitals and health examination centers, PCR test methods are currently performed on samples such as blood of patients to diagnose patients' disease.

According to the conventional PCR diagnosis method, it was possible to detect one type of target in one PCR tube, or to design a plurality of fluorescent channels to emit light according to the presence or absence of different targets using probes, and by using these probes, it was possible to simultaneously detect many types of targets corresponding to the number of fluorescent channels in one PCR tube.

However, the PCR method for detecting one kind of target in one PCR tube had problems in that there is a significant waste of reagents and the time required and the labor cost involved are tremendous. Additionally, the PCR method using a probe where of a plurality of fluorescent channels are designed to emit light according to the presence or absence of different targets had problems in that the designing of probes was difficult and that it had low reactivity (S A Bustin, *J. Mol. Endoorinol*, Vol. 29, pp. 23-39, 2002).

Accordingly, there is a demand for a means capable of detecting multiple types of targets atone time in one PCR tube.

Under these circumstances, the present inventors have made extensive efforts to develop a nucleic acid complex that can simultaneously perform the functions of a primer and a probe, and as a result, they have confirmed that when a nucleic acid complex pair is prepared by combining a nucleic acid structure which does not affect amplification while being able to complementarily bind to a nucleic acid structure pair acting as a primer, the nucleic acid complex pair may not only amplify a target nucleic acid as a primer but also detect the presence of absence of a target nucleic acid as a probe, thereby completing the present invention.

The information described in the background section is only intended to improve the understanding of the Background of the present invention, and thus it may not include information establishing prior art already known to those skilled in the art to which the present invention belongs.

SUMMARY

An object of the present invention is to provide a nucleic acid complex pair having a simple design that can be used for the detection of a target in a sample.

Another object of the present invention is to provide a PCR kit including a nucleic acid complex pair which can detect a plurality of kinds of targets per one fluorescent channel.

A further object of the present invention is to provide a method for detecting a target using the nucleic acid complex.

The problems to be solved by the present application are not limited to the above problems, and the problems which are not described above will be able to be understood by those skilled in the art to which the present application belongs from the present specification and the accompanying drawings.

According to an embodiment of the present application, there is provided a nucleic acid complex pair used for detecting a target DNA in a sample, wherein the nucleic acid complex pair includes a first nucleic acid complex including a first determination region, a first pairing region, and a first detection region and a second nucleic acid complex including a second determination region, a second paring region, and a second detection region, wherein the first determination region includes a forward primer corresponding to the target DNA, wherein the second determination region includes a reverse primer corresponding to the target DNA, wherein at least a part of the first pairing region and at least a part of the second pairing region are configured to complementarily bind to each other, wherein the first detection region or the second detection region comprises a signal material generating a detectable signal.

According to an embodiment of the present application, there is provided a method for detecting a target DNA in a sample, wherein the method includes providing a mixed solution including the sample and at least one type of a nucleic acid complex pair, wherein the nucleic acid complex pair includes a first nucleic acid complex and a second nucleic acid complex, wherein the first nucleic acid complex includes a first determination region having a forward primer corresponding to the target DNA, wherein the second nucleic acid complex includes a second determination region having a reverse primer corresponding to the target DNA, wherein at least a part of a first pairing region of the first nucleic acid complex and at least a part of a second pairing region of the second nucleic acid are configured to complementarily bind to each other, and wherein a property of a signal detected from a first detection region of the first nucleic acid complex and a second detection region of the second nucleic acid complex can be regulated based on whether at least a part of the first pairing region and at least a part of the second pairing region are complementarily bound to each other, amplifying at least a part of the target DNA with a cyclic heating of the mixed solution, and detecting a signal from the mixed solution including the target DNA and an amplification product for at least of a part of the target DNA.

A nucleic acid complex pair according to an embodiment can perform the detection of a target in a sample using the dissociation temperature of a tag that forms a complementary binding to the tag.

The PCR kit according to an embodiment can be used to perform the detection of a plurality of types of targets per fluorescence channel, including a plurality of kinds of nucleic acid complex pairs designed, so as to have different dissociation temperatures of tags.

The effects of the present application are not limited to the effects described above, and the effects which are not described above will be able to be understood by those skilled in the art to which the present application belongs from the present specification and the accompanying drawings.

BRIEF DESCRIPTION OF THE DRAWINGS

The above and other features and advantages of the present invention will become more apparent by describing in detail exemplary embodiments thereof with reference to the attached drawings in which:

FIG. 3 shows views illustrating the binding of a first nucleic acid complex 110 and/or a second nucleic acid complex 120 to a target material TM according to an embodiment of the present application;

FIG. 4 shows views illustrating the direction of the binding between the first nucleic acid complex 110 and the second nucleic acid complex 120 according to an embodiment of the present application:

FIG. 5 shows views illustrating the interaction between a first detection region 113 and a second detection region 123 according to an embodiment of the present application:

FIGS. 7 and 8 show views illustrating the changes in the binding relationship of a nucleic acid complex pair in PCR reaction according to an embodiment of the present application;

FIG. 10 shows views illustrating the graphs obtained during the detection of melting curves according to an embodiment of the present application;

FIG. 11 shows views illustrating the identified dissociation peak values obtained during the identification according to an embodiment of the present application:

FIG. 12 shows views illustrating the melting curve with regard to one fluorescent channel according to an embodiment of the present application (see 12(a)), and views illustrating the differential melting curve with regard to one fluorescent channel according to an embodiment of the present application (see 12(b)):

FIG. 14 shows views illustrating a unit cell UC in digital PCR according to an embodiment of the present application;

FIG. 16 shows views illustrating a method for performing the detection of melting curves in digital PCR according to an embodiment of the present application;

DETAILED DESCRIPTION OF THE INVENTION

Figure 1:
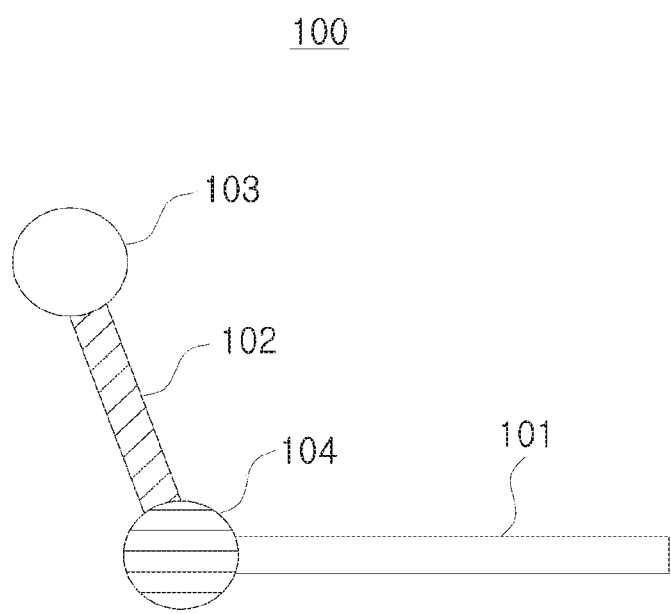
FIG. 1 shows a view illustrating a nucleic acid complex 100 according to an embodiment of the present application.

It should be understood that the embodiments described herein are for the purpose of clarifying the idea of the present application to those skilled in the art to which the present application belongs and thus the present application is not limited to the embodiments described herein, and should be interpreted to include modifications or variations that do not depart from the spirit of the present application.

Although the terms used in the present specification have been selected considering the functions in the present application and the general terms currently in widespread use have been chosen, these terms may vary depending on the intent, custom, or the emergence of new technology by those of ordinary skill in the art to which this application belongs. However, if a specific term is defined as an arbitrary meaning, the meaning of the term will be described separately. Accordingly, the terms used herein should be interpreted based on the actual meaning of the term rather than on the name of the term, and on the content throughout the description.

The drawings accompanied hereto are intended to facilitate the description of the present application. As occasion demands, the shapes shown in the drawings may be exaggerated to facilitate understanding of the present application, and thus the present application is not limited to the drawings.

In the following description, a detailed description of known configurations or functions related to the present application will be omitted when it is determined that the gist of the present application may be obscure.

According to an embodiment of the present application, there is provided a nucleic acid complex pair used for detecting a target DNA in a sample, wherein the nucleic acid complex pair includes a first nucleic acid complex including a first determination region, a first pairing region, and a first detection region; and a second nucleic acid complex including a second determination region, a second paring region, and a second detection region, wherein the first determination region includes a forward primer corresponding to the target DNA, wherein the second determination region includes a reverse primer corresponding to the target DNA, wherein at least a part of the first pairing region and at least a part of the second pairing region are configured to complementarily bind to each other, wherein the first detection region or the second detection region includes a signal material that generates a detectable signal.

The target DNA herein may have a single-stranded DNA structure containing a first target nucleic acid sequence to be described below. Alternatively, the target DNA may have a double-stranded DNA structure containing a first target nucleic acid sequence to be described below. Alternatively, the target DNA may have a single-stranded DNA structure containing a second target nucleic acid sequence to be described below. Alternatively, the target DNA may have a double-stranded DNA structure containing a second target nucleic acid sequence to be described below. Alternatively, the target DNA may have a single-stranded DNA structure containing a first target nucleic acid sequence and a second target nucleic acid sequence to be described below. Alternatively, the target DNA may have a double-stranded DNA structure containing. Alternatively, the target DNA may have a double-stranded DNA structure containing a first target nucleic acid sequence and a second target nucleic acid sequence to be described below.

A forward primer herein for the target DNA may be a forward primer that complementarily binds to one region of the target DNA. The forward primer for the target DNA may be a forward primer that complementarily binds to one region of the target DNA when the double-strand of the target DNA is heat-denatured into be in the form of single-stranded DNA.

A reverse primer for the target DNA may be a reverse primer that complementarily binds to one region of the target DNA. The reverse primer for the target DNA may be a reverse primer that complementarily binds to one region of the target DNA when the double-strand of the target DNA is heat-denatured into be in the form of single-stranded DNA.

According to an embodiment of the present application, there may be provided a nucleic acid complex pair used for detecting a target DNA in a sample, wherein the nucleic acid complex pair includes a forward primer and a reverse primer, wherein the forward primer includes at least one of deoxyribonucleic acid (DNA), peptide nucleic acid (PNA), locked nucleic acid (LNA), hexose nucleic acid (HNA), and ribonucleic acid (RNA), wherein the reverse primer includes at least one of the deoxyribonucleic acid (DNA), the peptide nucleic acid (PNA), the locked nucleic acid (LNA), the hexose nucleic acid (HNA), and the ribonucleic acid (RNA).

According to an embodiment of the present application, there may be provided a nucleic acid complex, wherein when the first detection region includes a signal material, the second detection region includes a quenching material involved in changing a property of the detectable signal generated from the first detection region, wherein when the second detection region includes the signal material, the first detection region includes a quenching material involved in changing a property of the detectable signal generated from the second detection region.

According to an embodiment of the present application, there may be provided a nucleic acid complex pair on which the properties of signals obtained from the first detection region and the second detection region can be regulated, wherein the characteristics of signals can be regulated based on whether or not at least a part of the first pairing region is complementarily bound to at least a part of the second pairing region each other.

What is meant by that the first detection region includes a signal material is that the first detection region may include a fluorescent material from which an optical signal can be detected based on the version of the device (e.g., an optical signal included in a wavelength range corresponding to a predetermined wavelength band), what is meant by that the first detection region includes a signal material is that the first detection region may include a signal-generating material from which an electrical signal can be detected based on the version of the device (e.g., an electric field that is densified more than a predetermined threshold)

What is meant by that the second detection region includes a signal material is that the second detection region may include a fluorescent material from which an optical signal can be detected based on the version of the device (e.g., an optical signal included in a wavelength range corresponding to a predetermined wavelength band). What is meant by that the second detection region includes a signal material is that the second detection region may include a signal-generating material from which an electrical signal can be detected based on the version of the device (e.g., an electric field that is densified more than a predetermined threshold).

What is meant by that the first detection region includes a quenching material involved in changing a property of a signal generated from the second detection region may be that the first detection region includes a quencher acting on the fluorescence of the second detection region when the second detection region includes a fluorescent material, wherein the quencher acts according to the principle of Förster resonance energy transfer (FRET) that the recipient's energy is abolished by the energy transfer while the donor is in an excited state.

What is meant by that the first detection region includes a quenching material involved in changing a property of a signal generated from the second detection region may be that the first detection region includes an electrical signal-inhibiting material that cancels off the signal generated from the second detection region when the second detection region includes the electrical signal-generating material What is meant by that the second detection region includes a quenching material involved in changing a property of a signal generated from the first detection region may be that the second detection region includes a quencher that acting on the fluorescence of the first detection region when the first detection region includes a fluorescent material, wherein the quencher acts according to the principle of Förster resonance energy transfer (FRET) that the recipient's energy is abolished by the energy transfer while the donor is in an excited state.

What is meant by that the second detection region includes a quenching material involved in changing a property of a signal generated from the first detection region may be that the second detection region includes an electrical signal-inhibiting material that cancels off the signal generated from the first detection region, when the first detection region includes the electrical signal-generating material According to an embodiment of the present application, there may be provided a nucleic acid complex pair, wherein the first nucleic acid complex includes a first blocking region for preventing a generation of an amplification product for the first pairing region, and the second nucleic acid complex includes a second blocking region for preventing a generation of an amplification product for the second pairing region.

According to an embodiment of the present application, there may be provided a nucleic acid complex pair, wherein the first blocking region is positioned between the first determination region and the first detection region, and the second blocking region is positioned between the second determination region and the second detection region.

According to an embodiment of the present application, there may be provided a nucleic acid complex pair, wherein the nucleic acid complex pair is used for a PCR (polymerase chain reaction) process, and the PCR is performed for amplifying at least a part of the target DNA.

According to an embodiment of the present application, wherein at least a part of the first pairing region are complementary hybridized with at least a part of the second pairing region.

According to an embodiment of the present application, there may be provided a kit for polymerase chain reaction (PCR), which includes an enzyme involved in a PCR reaction and the nucleic acid complex pair described above.

According to an embodiment of the present application, there may be provided a method for detecting a target DNA in a sample, wherein the method comprises:

(a) providing a mixture solution comprising a sample and at least one type of a nucleic acid complex pair, wherein the nucleic acid complex pair comprises a first nucleic acid complex and a second nucleic acid complex, wherein the first nucleic acid complex comprises a first determination region having a forward primer corresponding to the target DNA, wherein the second nucleic acid complex comprises a second determination region having a reverse primer corresponding to the target DNA, wherein at least a part of a first pairing region of the first nucleic acid complex and at least a part of a second pairing region of the second nucleic acid are configured to complementarily bind to each other, and wherein a property of a signal obtained from a first detection region of the first nucleic acid complex and a second detection region of the second nucleic acid complex is regulated based on whether or not at least a part of the first pairing region and at least a part of the second pairing region are complementarily bound to each other:

(b) amplifying at least a part of the target DNA by cyclic heating of the mixture solution and (c) detecting a signal from the mixture solution comprising the target DNA and an amplification product for at least of a part of the target DNA.

With regard to the amplification product for at least a part of a target DNA, may be a product including a domain where dNTP provided in a mixture solution is elongated through a covalent bond at an end of a forward primer or reverse primer, when at least one cycle of nucleic acid sequence amplification reaction is carried out by binding a forward primer or a reverse primer to correspond to at least a part of the target DNA.

The product herein may be a single-strand having the same sequence as at least a part of the target DNA. Alternatively, the product may be a double-strand having the same sequence as at least a part of the target DNA. Alternatively, the product may be a single-strand having a sequence complementary to at least a part of the target DNA Alternatively, the product may be a double-strand having a sequence complementary to at least a part of the target DNA.

According to an embodiment of the present application, there may be provided a method for detecting a target DNA in a sample, wherein the first nucleic acid complex further includes a first blocking region for preventing a generation of an amplification product for the first pairing region, wherein the first blocking region is positioned between the first determination region and the first detection region, and the second nucleic acid complex further includes a second blocking region for preventing a generation of an amplification product for the second pairing region, wherein the second blocking region is positioned between the second determination region and the second detection region.

According to an embodiment of the present application, there may be provided a method for detecting a target DNA in a sample, which further includes, after the amplifying, lowering a temperature of the mixture solution below at least 40° C. for inducing a complementary binding between at least a part of the first pairing region and at least a part of the second pairing region.

According to an embodiment of the present application, there may be provided a method for detecting a target DNA in a sample, which further includes, after the detecting, identifying a dissociation peak value related to a dissociation temperature of the first pairing region and the second pairing region based on the detected signal in order to detect the target DNA in the sample.

According to an embodiment of the present application, there may be provided a method for detecting a target DNA in a sample, wherein on the step of providing the mixture solution in the method which is disclosed the above, at least a part of the first pairing region and a part of the second pairing region are complementary bound to each other.

According to an embodiment of the present application, the amplification of at least a part of the target DNA may be to produce an amplified product for at least a part of the target DNA by performing a PCR reaction using a primer (i.e., a forward primer and/or a reverse primer) corresponding to at least a part of the sequence of the target DNA of the sample contained in the mixture solution.

There may be provided a method for detecting a target DNA in a sample, which includes heat-denaturing the target DNA and the amplification product for at least of a part of the target DNA into a single-strand DNA; annealing the first determination region to a part of the target DNA; annealing the second determination region to the other part of the target DNA; and elongating DNA so as to produce the amplification product for at least of a part of the target DNA.

The elongation of DNA herein may be that, a nucleotide unit (e.g., DNA) is elongated through a covalent bond as having a nucleotide sequence complementary to the target material TM bound to the primer, in a polymerization where an amplification product is generated for a target material TM containing a target nucleic acid sequence to which a primer bound.

According to an embodiment of the present application, there may be provided a method for detecting a target DNA in a sample, wherein in the amplifying at least a part of the target DNA, the step of heat-denaturing, the step of annealing, and the step of extending DNA are sequentially performed at least twice.

According to an embodiment of the present application, there may be provided a method for detecting a target DNA in a sample, wherein the annealing of the first determination region and the step of annealing of the second determination region are performed simultaneously, which is disclosed the above.

According to an embodiment of the present application, there may be provided a PCR kit, which includes: a nucleic acid complex pair which includes a first nucleic acid complex including a forward primer and a second nucleic acid complex including a reverse primer, in which the first nucleic acid complex includes a first pairing region different from the forward primer and the pairing region includes a second pairing region different from the reverse primer and the first and second pairing regions are complementarily bound to each other; and a probe complex which complementarily binds to a second target nucleic acid sequence different from a first target nucleic acid sequence binding to the forward primer or the reverse primer.

A PCR kit, in which the first pairing region is connected to a first detection region and the second pairing region is connected to a second detection region, and the first detection region or the second detection region includes a signal material generating a signal, may be provided.

A PCR kit, in which the properties of the signals detected from the first detection region and the second detection region are changed based on the presence of a binding between the first pairing region and the second pairing region, may be provided. A PCR kit, in which the first nucleic acid complex comprises a first block core to prevent the production of an amplification product for the first pairing portion and the second nucleic acid complex comprises a first blocking portion for preventing the generation of an amplification product for the second pairing portion, A kit for PCR may be provided, comprising a second block coat A PCR kit, in which a target material including the first target nucleic acid sequence is a single-strand the same as a target material including the second target nucleic acid sequence, may be provided.

A PCR kit, in which the first nucleic acid complex includes a first blocking region to prevent the generation of amplification products for the first pairing region, and the second nucleic acid complex includes a second blocking region to prevent the generation of amplification products for the second pairing region, may be provided.

A PCR kit, in which an enzyme involved in the PCR reaction is further included, may be provided.

A PCR kit, in which the enzyme is a DNA polymerase, may be provided, wherein the DNA polymerase is involved in the production of an amplification product for at least a part of an oligonucleotide associated with a second target nucleic acid sequence and lacks the nucleic acid terminal hydrolase activity of the DNA polymerase.

A PCR kit, in which the probe complex includes a determination region binding to the second target nucleic acid sequence, and a pair region involved in the formation of a single-strand hairpin structure and not binding to the second target nucleic acid sequence, may be provided.

A PCR kit, in which the determination region is selected from the group consists of deoxyribonucleic acid (DNA), locked nucleic acid (LNA), peptide nucleic acid (PNA), hexose nucleic acid (HNA), and ribonucleic acid (RNA), or various nucleic acid analogs, or a combination thereof, may be provided.

A PCR kit, in which the binding force between the first pairing region and the second pairing region is different from the binding force between the probe complex and the second target nucleic acid sequence, may be provided.

A PCR kit, in which the probe complex includes a first probe binding to the second target nucleic acid sequence and a second probe not binding to the second target nucleic acid sequence, may be provided.

A PCR kit, in which at least a part of the nucleic acid sequence included in the first probe is separated from the first probe during a PCR process and binds to at least a part of the second probe, may be provided.

A PCR kit, in which the binding force between the second probe and the nucleic acid sequences isolated from the first probe is different from the binding force between the first pairing region and the second pairing region, may be provided.

A PCR kit, in which the ratio between the forward primers and the reverse primers included in the PCR kit is not limited to 1:1, may be provided.

<Nucleic Acid Complex 100>

FIG. 1 shows a view illustrating a nucleic acid complex 100 according to an embodiment of the present application.

A nucleic acid complex 100 according to one embodiment of the present application may include a determination region 101, a pairing region 102, a detection region 103, and/or a blocking region 104. In an embodiment, a nucleic acid complex 100 may include a determination region 101, a pairing region 102, a detection region 103, and a blocking region 104. In another embodiment, a nucleic acid complex 100 may include a detection region 101, a pairing region 102, and a detection region 103. As still another embodiment, a nucleic acid complex 100 may include a determination region 101, a pairing region 102, and a blocking region 104. As still another embodiment, a nucleic acid complex 100 may include a determination region 101 and a pairing region 102.

A nucleic acid complex 100 according to an embodiment of the present application is not limited to the combination of the components described above, and at least one of the above-described components may be omitted or other components may be included further.

A nucleic acid complex 100 may include a determination region 101. The determination region 101 may include a domain which complementarily binds to another nucleic acid sequence. The determination region 101 may include a domain that specifically binds to another nucleic acid sequence. What is meant by that the determination region 101 includes a domain which complementarily binds to another nucleic acid sequence is that a part of the domain of the determination region 101 corresponds to at least one of the electrical, chemical, and physical properties, to another nucleic acid sequence and thus may be associated with another nucleic acid sequence.

In an embodiment, the determination region 101 may include a domain in which a chemical bonding with a different nucleic acid sequence may occur. In other words, the determination region 101 may include a domain which can perform at least one binding among a covalent binding, a hydrogen binding, an ionic binding, and a hydrophobic binding, to another nucleic acid sequence.

The determination region 101 may include at least one nucleic acid sequence. Preferably, the determination region 101 may include 5 mer to 50 mer nucleic acid sequence. More preferably, the determination region 101 may include 10 mer to 25 mer nucleic acid sequence.

The at least one nucleic acid (or nucleic acid analogs) may consist of deoxyribonucleic acid (DNA), locked nucleic acid (LNA), peptide nucleic acid (PNA), hexose nucleic acid (HNA), and ribonucleic acid (RNA), or various nucleic acid analogs, or a combination thereof.

The nucleic acid complex 100 may include a pairing region 102. The pairing region 102 may include a domain which complementarily binds to another nucleic acid sequence. The pairing region 102 may include a domain that specifically binds to another nucleic acid sequence. What is meant by that the pairing region 102 includes a domain which complementarily binds to another nucleic acid sequence is that a part of the domain of the pairing region corresponds to at least one of the electrical, chemical, and physical properties, to another nucleic acid sequence and thus may be associated with another nucleic acid sequence.

In an embodiment, the pairing region 102 may include a domain in which a chemical bonding with a different nucleic acid sequence may occur. In other words, the pairing region 102 may include a domain which can perform at least one binding among a covalent binding, a hydrogen binding, an ionic binding, and a hydrophobic binding to another nucleic acid sequence.

The pairing region 102 may include a domain which complementarily binds to another nucleic acid complex 100. The pairing region 102 may include a domain which complementarily binds to a pairing region 102 of a different nucleic acid complex 100. In an embodiment, the pairing region 102 may include a domain which is implemented so as to have a complementary nucleotide sequence to a pairing region 102 of a different nucleic acid complex 100.

The pairing region 102 may include at least one nucleic acid sequence. In an embodiment, preferably, the pairing region 102 may include 2 mer to 15 mer nucleic acid sequence. In another embodiment, preferably, the pairing region 102 may include 5 mer to 10 mer nucleic acid sequence.

The at least one nucleic acid (or nucleic acid analogs) may consist of deoxyribonucleic acid (DNA), locked nucleic acid (LNA), peptide nucleic acid (PNA), hexose nucleic acid (HNA), and ribonucleic acid (RNA), or various nucleic acid analogs, or a combination thereof.

A nucleic acid complex 100 may include a detection region 103. The detection region 103 may include a domain capable of emitting energy.

The detection region 103 may include a domain capable of exchanging energy. Alternatively, the detection region 103 may include a domain capable of providing energy. Alternatively, the detection region may include a domain capable of receiving energy. The energy emitted from the detection region 103 may include at least one among the chemical energy, electrical energy, light-emitting energy, and electromagnetic energy. In an embodiment, the detection region 103 may include a fluorescent material. In another embodiment, the detection region 103 may include a domain where the electronegativity is relatively higher. In still another embodiment, the detection region 103 may include a domain which forms a hydrogen binding with a different domain.

The nucleic acid complex 100 may include a blocking region 104. The blocking region 104 may block information of any one domain connected to the blocking region 104 from being acquired by another material.

In a case where a nucleic acid complex 100 according to an embodiment of the present application is used in a PCR, the blocking region 104 may prevent a polymerase from acquiring at least a part of the nucleic acid sequence connected to the blocking region 104. The blocking region 104 may be regulated such that a polymerase can be prevented from acquiring at least a part of the nucleic acid sequence of the pairing region 102 connected to the blocking region 104. The blocking region 104 may prevent an amplification product from being produced for the pairing region 102 connected to the blocking region 104 by a polymerase.

The term "amplification product" herein may refer to a material produced as a result of at least one cycle of PCR reaction. The term "amplification product" herein may refer to a material which is produced as nucleotide units are extended through a covalent bond by performing a PCR reaction.

The term "amplification product for pairing region 102" may refer to a material which is produced as nucleotide units are extended through a covalent bond so as to complementarily correspond to the nucleotide sequence of the pairing region 102.

The blocking region 104 may include a factor interfering with the linkage of the sugar-phosphate backbone which constitutes a nucleic acid strand. In an embodiment, the blocking region 104 may include a sugar-phosphate backbone where the bases are removed. In another embodiment, the blocking region 104 may include a nucleotide where bases are modified. In another embodiment, the blocking region 104 may include polyethyleneglycol (PEG).

The determination region 101, pairing region 102, detection region 103, and/or blocking region 104 of the nucleic acid complex 100 according to an embodiment of the present application may have a predetermined positional relationship.

According to an embodiment of the present application, the determination region 101 and the pairing region 102 may be connected. The determination region 101 and the pairing region 102 may be connected in a directly-bound form. In an embodiment, the determination region 101 and the pairing region 102 may be connected based on the chemical binding force. The determination region 101 and the pairing region 102 may be connected based on at least one binding among the covalent binding, hydrogen binding, ionic binding, and hydrophobic binding. Alternatively, the determination region 101 and the pairing region 102 may be connected by being mediated through an additional material. In an embodiment, the additional material that mediates the connection between the determination region 101 and the pairing region 102 may be a chemical linker (e.g., PCR blocker), a fluorescent material, DNA fragment, etc.

According to an embodiment of the present application, the pairing region 102 and the detection region 103 may be connected. The detection region 103 may be disposed at an end of the pairing region 102. When detection region 103 is disposed at an end of the pairing region 102, the detection region 103 and the pairing region 102 may be connected by chemical binding force. Alternatively, the detection region 103 may be disposed such that it is inserted into the middle of the pairing region 102. In other words, the detection region 103 may be connected such that it is bound to at least one domain of the pairing region 102. Alternatively, the detection region 103 may be disposed to be spaced apart from the pairing region 102. For example, the detection region 103 may be connected such that it is bound to the blocking region 104 which is connected to the pairing region 102.

According to an embodiment of the present application, the determination region 101 and the detection region 103 may be connected. The detection region 103 may be disposed at an end of the determination region 101. When the detection region 103 is disposed at an end of the determination region 101, the detection region 103 and the determination region 101 may be connected by chemical binding force. Alternatively, the detection region 103 may be disposed such that it is inserted into the middle of the determination region 101. In other words, the detection region 103 may be connected such that it is bound to at least one domain of the determination region 101. Alternatively, the detection region 103 may be disposed to be spaced apart from the determination region 101. For example, the detection region 103 may be connected such that it is bound to the blocking region 104 which is connected to the determination region 101.

According to an embodiment of the present application, the blocking region 104 may be disposed between the determination region 101 and the pairing region 102. The determination region 101 may be disposed to be relatively closer to the blocking region 104 than to the pairing region 102. The pairing region 102 may be disposed to be relatively closer to the blocking region 104 than to the determination region 101.

According to an embodiment of the present application, when the detection region 103 is disposed between the determination region 101 and the pairing region 102, the blocking region 104 may be connected to the detection region 103. In other words, it may be implemented in the order of the determination region 101, detection region 103, blocking region 104, and pairing region 102, or may be implemented in the order of the determination region 101, blocking region 104, detection region 103, and pairing region 102, in the nucleic acid complex 100 according to an embodiment of the present application Up to now, the constituting elements of the nucleic acid complex 100 and the positional relationship thereof according to one embodiment of the present application have been described in detail. Hereinafter, a nucleic acid complex pair according to the present application will be disclosed in detail, which can be used in the field where nucleic acid is used <Nucleic Acid Complex Pair>

The nucleic acid complex pair according to one embodiment of the present application may include a first nucleic acid complex 110 and a second nucleic acid complex 120. The nucleic acid complex pair may comprise a first nucleic acid complex 110 and a second nucleic acid complex 120. The nucleic acid complex pair may be provided while forming a pair of the first nucleic acid complex 110 and the second nucleic acid complex.

Figure 2:
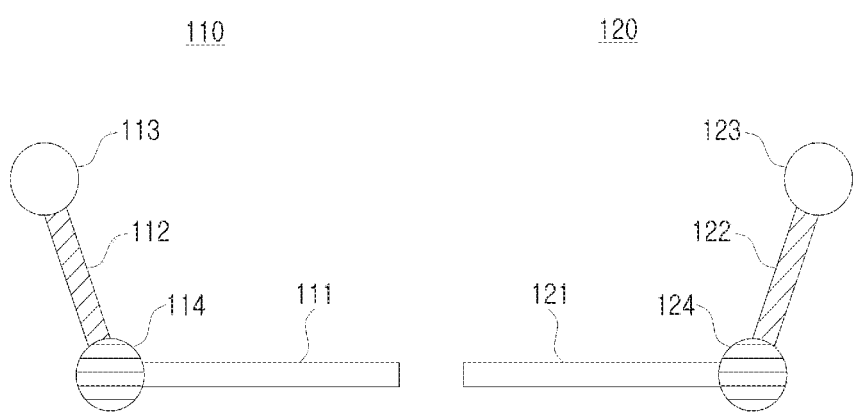
FIG. 2 shows a view illustrating a nucleic acid complex pair according to an embodiment of the present application.

FIG. 2 shows a view illustrating a nucleic acid complex pair according to an embodiment of the present application.

The nucleic acid complex pair according to one embodiment of the present application may include a first nucleic acid complex 110 and a second nucleic acid complex 120.

The first nucleic acid complex 110 may include a first determination region 11, a first pairing region 112, a first detection region 113 and/or a first blocking region 114. In an embodiment, the first nucleic acid complex 110 may include a first determination region 111, a first pairing region 112, a first detection region 113, and a first blocking region 114. In another embodiment, the first nucleic acid complex 110 may include a first determination region 111, a first pairing region 112, and a first detection region 113. In still another embodiment, the first nucleic acid complex 110 may include a first determination region 111, a first pairing region 112, and a first blocking region 114. In still another embodiment, the first nucleic acid complex 110 may include a first determination region 111 and a first pairing region 112.

The second nucleic acid complex 120 may include a second determination region 121, a second pairing region 122, a second detection region 123 and/or a second blocking region 124. In an embodiment, a second nucleic acid complex 120 may include a second determination region 121, a second pairing region 122, a second detection region 123, and a second blocking region 124. In another embodiment, a second nucleic acid complex 120 may include a second determination region 121, a second pairing region 122, and a second detection region 123. In still another embodiment, a second nucleic acid complex 120 may include a second determination region 121, a second pairing region 122, and a second blocking region 124. In still another embodiment, a second nucleic acid complex 120 may include a second determination region 121 and a second pairing region 122.

The nucleic acid complex 100 according to an embodiment of the present application 100 is not limited to the combination of the constitutional elements described above, but at least one constitutional element may be omitted or another constitutional element may be further included.

The first nucleic acid complex 110 and the second nucleic acid complex 120 of the nucleic acid complex pair according to one embodiment of the present application may have the same constitution. In an embodiment, the first nucleic acid complex 110 may include a first determination region 111, a first pairing region 112, a first detection region 113, and a first blocking region 114; and the second nucleic acid complex 120 may include a second determination region 121, a second pairing region 122, a second detection region 123, and a second blocking region 124.

The first nucleic acid complex 110 and the second nucleic acid complex 120 of the nucleic acid complex pair according to another embodiment of the present application may have a constitution different from each other. In an embodiment, the first nucleic acid complex 110 may include a first determination region 111, a first pairing region 112, and a first detection region 113; and the second nucleic acid complex 120 may include a second determination region 121, a second pairing region 122, and a second blocking region 124.

The first determination region 111 can complementarily bind to a first target nucleic acid sequence TS1. The first determination region 111 can specifically bind to the first target nucleic acid sequence TS1. "A first target nucleic acid sequence TS1" herein may refer to a particular nucleic acid sequence which has a nucleotide sequence that can complementarily bind to the first determination region 111.

The complementary binding between the first determination region 111 and the first target nucleic acid sequence TS1 may mean that at least one property among electrical, chemical, and physical properties may correspond to each other and they are thus associated. In an embodiment, the first determination region 111 may include a domain having a chemical binding force, and the first determination region 111 may be able to form hydrogen binding with the first target nucleic acid sequence TS1.

The binding force between the first determination region 111 and the first target nucleic acid sequence TS1 may be determined in connection with at least one of the types of unit nucleic acids, types of base of unit nucleic acids, the number of nucleotides involved in a complementary binding. In an embodiment, when at least one unit nucleic acid of a first determination region 111 that binds to the first target nucleic acid sequence TS1 is PNA, a binding between the first determination region 111 and the first target nucleic acid sequence TS1 with a relatively stronger binding force, may be implemented, compared to when the unit nucleic acid of the first determination region 111 is DNA. In another embodiment, the binding force between the first target nucleic acid sequence TS1 and a first determination region 101 may be determined based on the type of bases involved in the complementary binding between the first target nucleic acid sequence TS1 and the first determination region 111. As the C (cytosine)-G (guanine) content of the nucleotides involved in the complementary binding between the first target nucleic acid sequence TS1 and the first determination region 101 becomes higher, the binding force between the first target nucleic acid sequence TS1 and the first determination region 111 may be increased.

The first determination region 111 can perform a function of complementarily binding to a target material TM including a first target nucleic acid sequence TS1. The target material TM may be a single-strand including the target nucleic acid sequence or a double-strand including the target nucleic acid sequence. The target material TM may be an oligonucleotide, fluorescent material, protein, cell, etc which linked to the target nucleic acid sequence.

The second determination region 121 may complementarily bind to a second target nucleic acid sequence TS2. The second determination region 121 may specifically bind to the second target nucleic acid sequence TS2. "A second target nucleic acid sequence TS2" herein may refer to a particular nucleic acid sequence having a nucleotide sequence that can complementarily binds to the second determination region 121.

The complementary binding between the second determination region 121 and the second target nucleic acid sequence TS2 may mean that at least one property among electrical, chemical, and physical properties may correspond to each other and they are thus associated. In an embodiment, the second determination region 121 may include a domain having a chemical binding force, and the second determination region 121 may be able to form hydrogen binding with the second target nucleic acid sequence TS2.

The binding force between the second determination region 121 and the second target nucleic acid sequence TS2 may be determined in connection with at least one of the types of unit nucleic acids, types of bases of unit nucleic acids, the number of nucleotides involved in a complementary binding. In an embodiment, when at least one unit nucleic acid of a second determination region 121 that binds to the second target nucleic acid sequence TS2 is PNA, a binding between the second determination region 121 and the second target nucleic acid sequence TS2 with a relatively stronger binding force, may be implemented, compared to when the unit nucleic acid of the second determination region 121 is DNA. In another embodiment, the binding force between the second target nucleic acid sequence TS2 and a second determination region 121 may be determined based on the type of base involved in the complementary binding between the second target nucleic acid sequence TS2 and the second determination region 121. As the C (cytosine)-G (guanine) content of the nucleotides involved in the complementary binding between the second target nucleic acid sequence TS2 and the second determination region 101 becomes higher, the binding force between the first target nucleic acid sequence TS1 and the second determination region 121 may be increased.

The second determination region 121 can perform a function of complementarily binding to a target material TM including a second target nucleic acid sequence TS2. The target material TM may be a single-strand including the target nucleic acid sequence or a double-strand including the target nucleic acid sequence. The target material TM may be an oligonucleotide, fluorescent material, protein, cell, etc. which linked to the target nucleic acid sequence.

The first target nucleic acid sequence TS1 that binds to the first determination region 111 of the first nucleic acid complex 110 and the second target nucleic acid sequence TS2 that binds to the second determination region 121 may be included in the same target material TM. In an embodiment, the first determination region 111 and the second determination region 121 may bind to a target material TM, where a second target nucleic acid sequence is included in the other domain of a single-strand including the first target nucleic acid sequence TS1 (see FIG. 3(a)). Alternatively, the second target nucleic acid sequence TS2 may be included in one domain of the other single-strand bound to a single-strand including the first target nucleic acid sequence TS1. In an embodiment, the first determination region 111 and the second determination region 121 may bind to a target material TM, where a single-strand including the first target nucleic acid sequence TS1 and a single-strand including the second target nucleic acid sequence TS2 form a double-strand (see FIG. 3(b)).

When the nucleic acid complex 100 according to an embodiment of the present application pair is used in PCR, the first nucleic acid complex 110 and the second nucleic acid complex 120 may be used as primers. The first determination region 111 may function as a forward primer or reverse primer. The second determination region 121 may function as a forward primer or reverse primer. In an embodiment, when the first determination region 111 functions as a forward primer, the second determination region 121 may function as a reverse primer.

The first pairing region 112 may complementarily bind to a different pairing region 102. The nucleic acid complex 100 according to an embodiment of the present application pair may be implemented so that the first pairing region 112 and the second pairing region 122 can complementarily bind to each other. The first pairing region 112 may include a nucleotide sequence complementary to the second pairing region 122. The second pairing region 122 may include a nucleotide sequence complementary to the first pairing region 112.

According to an embodiment of the present application, the shapes of the nucleic acid complex pair by the binding between the first pairing region 112 and the second pairing region 122 may vary, according to the nucleotide sequences arrangement of the first pairing region 112 and the second pairing region 122. According to an embodiment of the present application, the shape of the structure of the nucleic acid complex pair by the binding between the first pairing region 112 and the second pairing region 122 may vary, according to the binding direction between the first pairing region 112 and the second pairing region 122.

FIG. 4 shows views illustrating the direction of the binding between the first nucleic acid complex 110 and the second nucleic acid complex 120 according to an embodiment of the present application.

According to an embodiment of the present application, when a nucleic acid complex pair may be implemented such that a domain adjacent to the first determination region 111 of the first pairing region 112 complementarily binds to a domain adjacent to the second determination region 121 of the second pairing region 122, a structure of a nucleic acid complex pair may be formed, where the first determination region 111 and the second determination region 121 are positioned on the same side with reference to the first pairing region 112 and the second pairing region 122.

According to an embodiment of the present application, when a nucleic acid complex pair may be implemented such that a domain adjacent to the first blocking region 114 of the first pairing region 112 complementarily binds to a domain adjacent to the second blocking region 124 of the second pairing region 122, a structure of a nucleic acid complex pair may be formed, where the first determination region 111 and the second determination region 121 are positioned on the same side with reference to the first pairing region 112 and the second pairing region 122 (see FIG. 4(a)).

According to an embodiment of the present application, when a nucleic acid complex pair may be implemented such that a domain adjacent to the first determination region 111 of the first pairing region 112 complementarily binds to a domain spaced apart from the second determination region 121 of the second pairing region 122, a structure of a nucleic acid complex pair may be formed, where the first determination region 111 and the second determination region 121 are positioned on different side with reference to the first pairing region 112 and the second pairing region 122.

According to an embodiment of the present application, when a nucleic acid complex pair may be implemented such that a domain adjacent to the first blocking region 114 of the first pairing region 112 complementarily binds to a domain spaced apart from the second blocking region 124 of the second pairing region 122, a structure of a nucleic acid complex pair may be formed, where the first determination region 111 and the second determination region 121 are positioned on different axes with reference to the first pairing region 112 and the second pairing region 122 (see FIG. 4(b)).

As explained above, according to an embodiment of the present application, the shape of a nucleic acid complex pair may vary according to the binding between the first pairing region 112 and the second pairing region 122 according to the nucleotide sequences arrangement of the first pairing region 112 and the second pairing region 122. When the nucleic acid complex pair is used in a PCR reaction, the shape of the nucleic acid complex pair may be implemented in various forms, such as a quasi-circular structure, an quasi-hairpin structure, etc. based on the binding with the first target nucleic acid sequence TS1 or the second target nucleic acid sequence TS2 for the first pairing region 112 and the second pairing region 122. These will be explained in greater detail herein below.

The complementary binding between the first pairing region 112 and the second pairing region 122 may mean that at least one property among electrical, chemical, and physical properties can be corresponded and thus associated with each other. In an embodiment, the first pairing region 112 may include a domain having a chemical binding force, and the first pairing region 112 may form a hydrogen binding with the second pairing region 122. The second pairing region 122 may include a domain having a chemical binding force, and the second pairing region 122 may form a hydrogen binding with the first pairing region 112.

The binding force between the first pairing region 112 and the second pairing region 122 may be determined in connection with at least one among the types of unit nucleic acids, types of base of unit nucleic acids, the number of nucleotides involved in the complementary binding, and the number of mismatches. In an embodiment, the binding force between the first pairing region 112 and the second pairing region 122 may be determined based on the number of nucleotides involved in the complementary binding between the first pairing region 112 and the second pairing region 122. As the number of nucleotides involved in the complementary binding between the first pairing region 112 and the second pairing region 122 increases, the binding force between the first pairing region 112 and the second pairing region 122 may be increased. In another embodiment, the binding force between the first pairing region 112 and the second pairing region 122 may be determined based on the base type of nucleotides involved in the complementary binding between the first pairing region 112 and the second pairing region 122. As the C (cytosine)-G (guanine) content of the nucleotides involved in the complementary binding between the first pairing region 112 and the second pairing region 122 becomes higher, the binding force between the first pairing region 112 and the second pairing region 122 may be increased.

The first pairing region 112 and the second pairing region 122 may be separated. The first pairing region 112 and the second pairing region 122 may include a domain at which the binding between the first pairing region 112 and the second pairing region 122 are dissociated. In an embodiment, the domain where the binding is dissociated may coincide with a domain where the first pairing region 112 and the second pairing region 122 form a complementary binding. In other words, the domain where the first pairing region 112 and the second pairing region 122 form a complementary binding may coincide with a domain where the first pairing region 112 and the second pairing region 122 are separated as the first pairing region 112 and the second pairing region 122 are dissociated after being bound by the complementary binding between the first pairing region 112 and the second pairing region 122.

According to an embodiment of the present application, the first detection region 113 and the second detection region 123 may interact with each other. The first detection region 113 and the second detection region 123 may exchange energy with each other. In an embodiment, the first detection region 113 may provide energy to a second detection region 123. The second detection region 123 may receive energy from the first detection region 113. In another embodiment, the first detection region 113 may receive energy from the second detection region 123. The second detection region 123 may provide energy to the first detection region 113. In still another embodiment, the first detection region 113 may provide energy to the second detection region 123 and receive energy from the second detection region 123. The second detection region 123 may provide energy to the first detection region 113 and receive energy from the first detection region 103.

The first detection region 113 and the second detection region 123 may have different properties from each other. When the first detection region 113 and the second detection region 123 have an optical property, the optical property possessed by the first detection region 113 may be different from the optical property by the second detection region 123. In an embodiment, the wavelength band of light emitted from the first detection region 113 may be different from the wavelength band of light emitted from the second detection region 123. In another embodiment, the intensity of light emitted from the first detection region 113 may be different from the intensity of light emitted from the second detection region 123. In still another embodiment, the first detection region 113 may release light at a particular wavelength band, and the second detection region 123 may release light by altering the optical property of the light being released from the first detection region 113.

FIG. 5 shows views illustrating the interaction between the first detection region 113 and the second detection region 123 according to an embodiment of the present application.

For the nucleic acid complex 100 according to an embodiment of the present application pair, it may be defined as the effective interactive distance (ID) between the first detection region 113 and the second detection region 123. "Effective interactive distance (ID)" herein may refer to a standard distance being spaced apart from the first detection region 113 or the second detection region 123, where the interaction between the first detection region 113 and a second detection region 123 can be performed (see FIG. 5(a)).

The effective interactive distance (ID) may be determined based on the properties of the first detection region 113 and the second detection region 123. In the nucleic acid complex 100 according to an embodiment of the present application pair, when the first detection region 113 includes a fluorescent material and the second detection region 123 includes a quenching material (e.g., a quencher), the effective interactive distance (ID) may vary according to the properties of the fluorescent material and the quenching material. In an embodiment, when the quencher is within a range of 100 Å, if the optical properties released from the fluorescent material and the quencher are altered, the effective interactive distance (ID) may be 100 Å.

The distance between the first detection region 113 and the second detection region 123 may vary based on the binding between the first pairing region 112 and the second pairing region 122. When a complementary binding is performed between the first pairing region 112 and the second pairing region 122, the first detection region 113 and the second detection region 123 may be disposed adjacently. With regard to the nucleic acid complex 100 according to an embodiment of the present application pair, the presence of an interaction between the first detection region 113 and the second detection region 123 may be determined based on the binding between the first pairing region 112 and the second pairing region 122.

When the second detection region 123 is disposed within the effective interactive distance (ID) of the first detection region 113 by binding between the first pairing region 112 and the second pairing region 122, the detection signal due to the signal-generating materials included in the first detection region 113 and/or a second detection region 123 may be changed (see FIG. 5(b)). In an embodiment, a change of a signal may refer to a change of a wavelength band (e.g., a wavelength band of light) of a signal being detected from the first detection region 113 and the second detection region 123. In another embodiment, a change of a signal may refer to a change of an intensity of a signal (e.g., intensity of light) of a signal being detected from the first detection region 113 and the second detection region 123. In still another embodiment, a change of a signal may refer to a change exceeding the range of a preset wavelength band for a device capable of detecting the optical property of a solution containing a nucleic acid complex pair. As a result, the change of a signal detected from the first detection region 113 and the second detection region 123 may be confirmed as on/off of a signal change due the limitation of the device. This will be explained in more detail herein below.

When the nucleic acid complex pair according to the present application is used in a PCR reaction, the production of an amplification product for the first pairing region 112 and the second pairing region 122 may be prevented by the first blocking region 114 and the second blocking region 124. Conclusively, even after the completion of a PCR reaction, the first pairing region 112 and the second pairing region 122 may be maintained as a single-strand.

In the nucleic acid complex 100 according to an embodiment of the present application pair, the length of the amplification product including the first target nucleic acid sequence TS1 and the second target nucleic acid sequence TS2 may be implemented constantly. In other words, the first blocking region 114 and the second blocking region 124 may be involved in a process of allowing the amplification product including the first target nucleic acid sequence TS1 and the second target nucleic acid sequence TS2 to be formed in a constant length.

Until now, the nucleic acid complex 100 and the constituting elements thereof and their positional relationships were described specifically.

The nucleic acid complex 100 according to an embodiment of the present application pair may be used in various fields where nucleic acids are utilized.

For example, the nucleic acid complex 100 according to an embodiment of the present application pair may be utilized as a primer for the synthesis of plasmids, preparation of DNA chips, and DNA sequencing. In still another embodiment, the nucleic acid complex 100 according to an embodiment of the present application pair may be utilized for confirming the presence of a target nucleic acid sequence in a sample.

Hereinafter, various embodiments in which a nucleic acid complex pair is used are specifically disclosed to confirm the presence of a target nucleic acid sequence in a sample.

<Use of Nucleic Acid Complex Pair>

1. Identification of Presence of Target Nucleic Acid Sequence in Sample

For gene analysis, the presence of a target nucleic acid sequence in a sample can be confirmed. In an embodiment, the presence of a target nucleic acid sequence in a sample can be confirmed so as to confirm whether a subject is infected with a viral disease. In another embodiment, the presence of a target nucleic acid sequence in a sample can be confirmed so as to identify a species from a particular sample. In still another embodiment, the presence of a target nucleic acid sequence in a sample can be confirmed so as to confirm whether a target treatment can be effective for a subject. In still another embodiment, the presence of a target nucleic acid sequence in a sample can be confirmed so as to confirm genetically modified foods, contaminated foods, etc.

1.1 Confirmation of Presence of Target Sequence Using PCR Reaction 1.1.1 Use in Conventional PCR The nucleic acid complex 100 according to an embodiment of the present application pair may be used to confirm the presence of a target nucleic acid sequence in a sample. The nucleic acid complex pair may be used in a PCR reaction. The nucleic acid complex pair may be involved in the production of an amplification product for a target nucleic acid sequence. The nucleic acid complex pair may be involved in the process of detecting signals from a mixture solution where the nucleic acid complex pair is contained. The nucleic acid complex pair may be involved in the change of a detection signal from the mixed solution where the nucleic acid complex pair is contained.

Figure 6:
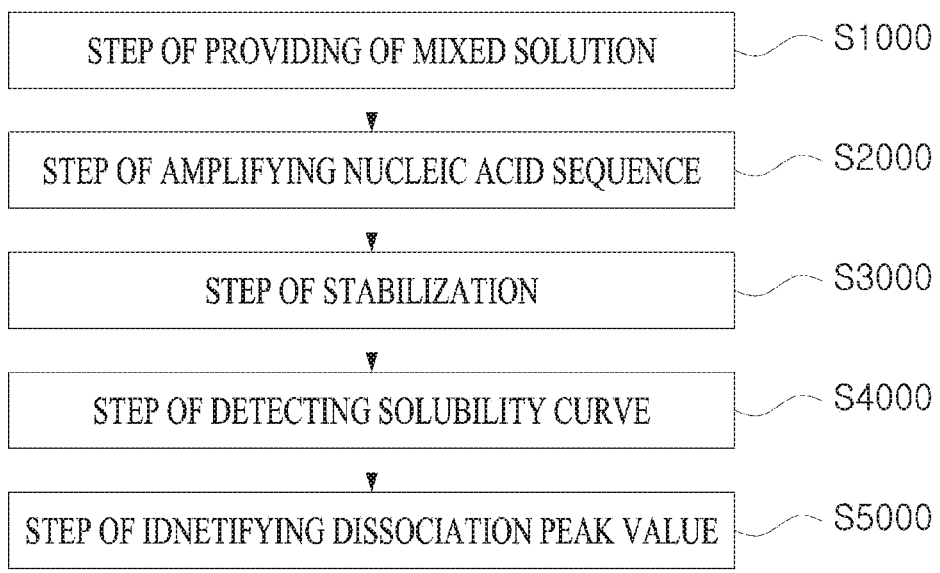
FIG. 6 shows a flowchart illustrating the sequence of identifying the presence of a target nucleic acid sequence in a sample according to an embodiment of the present application.

FIG. 6 shows a flowchart illustrating the sequence of identifying the presence of a target nucleic acid sequence in a sample according to an embodiment of the present application.

For identifying the presence of a target nucleic acid sequence in a sample, a step of providing a mixture solution S1000, a step of PCR reaction S2000, a step of stabilization S3000, a step of melting curve detection S4000, and a step of peak value detection S5000 may be performed.

Specifically, according to an embodiment of the present application, a sample and a mixture solution containing at least one type of a nucleic acid complex pair may be provided for the detection of presence of a target nucleic acid sequence in a sample S1000.

In an embodiment, the nucleic acid complex pair may include a first nucleic acid complex 110 and the second nucleic acid complex 120. The first nucleic acid complex 110 may include a first determination region 111, a first pairing region 112, a first detection region 113, and a first blocking region 114. The second nucleic acid complex 120 may include a second determination region 121, a second detection region 123, a second pairing region 122, and a second blocking region 124.

The first determination region 111 may perform a function of forming a complementary binding with a targeting nucleic acid sequence (i.e., a first target nucleic acid sequence TS1). The second determination region 121 may perform a function of forming a complementary binding with a targeting nucleic acid sequence (i.e., a second target nucleic acid sequence TS2). In an embodiment, the first target nucleic acid sequence TS1 and the second target nucleic acid sequence TS2 may be at least a part of the nucleic acid sequence associated with a disease to be detected. The first target nucleic acid sequence TS1 and the second target nucleic acid sequence TS2 may be included in a one double-strand.

In addition to the sample and the nucleic acid complex pair, the mixture solution may further contain at least one among a polymerizing enzyme involved in a polymerization reaction (e.g.; polymerase), a nucleotide fragment (e.g. deoxynucleotide triphosphate (dNTP)), a coenzyme involved in a PCR reaction (e.g.; $MgCl_2$, $MgSO_4$), and a buffer for providing an optimal pH and a salt concentration in a PCR reaction.

When a plurality of types of nucleic acid complex pairs are used, the first nucleic acid complex pair may contain a first signal material. The second nucleic acid complex pair may contain a second signal material. The first signal material and the second signal material may contain the same signal detecting material capable of detecting the same signal.

Herein, "same signal detecting material" may mean the same type of material. In an embodiment, when the first signal material contained in the first nucleic acid complex pair is JOE, the second signal material contained in the second nucleic acid complex pair may be JOE.

Herein, "same signal detecting material" may refer to a plurality of types of different material detected by the same signal (e.g., a signal included in the range of a wavelength band corresponding to a preset wavelength band) based on the version of a device. In an embodiment, when the first signal material included in the first nucleic acid complex pair is TET having a releasing wavelength of 548 lambda, the signal materials, JOE and TET may be detected by the light of the same wavelength band based on the version of a device, and herein the JOE and TET may be the same signal detecting material.

Additionally, the first target nucleic acid sequence TS1 of the first nucleic acid complex pair may be different from the first target nucleic acid sequence or the second target nucleic acid sequence of the second nucleic acid complex pair. The second target nucleic acid sequence TS2 of the first nucleic acid complex pair may be different from the first target nucleic acid sequence or the second target nucleic acid sequence of the second nucleic acid complex pair.

Additionally, the complementary binding force between the first pairing region 112 and the second pairing region 122 of the first nucleic acid complex pair may be different from the complementary binding force between the first pairing region 112 and the second pairing region 122 of the second nucleic acid complex pair. Specifically, the dissociation temperature at which the complementary binding between the first pairing region 112 and the second pairing region 122 of the first nucleic acid complex pair is dissociated may be different from the dissociation temperature at which the complementary binding between the first pairing region 112 and the second pairing region 122 of the second nucleic acid complex pair is dissociated.

Once a mixture solution is provided, a step of a PCR reaction for a mixture solution may be performed S2000.

Generally, a PCR reaction may include 1) a denaturation step where a nucleic acid structure constituting a double helix structure is separated using heat, 2) an annealing step where primers are allowed to bind to a target nucleic acid sequence, and 3) an extension (elongation) step where the amplification product for a target material TM including a target nucleic acid sequence to which primers are bound is produced. The above denaturation step, annealing step, and extension step may be repeatedly preformed in this order. Through the process, the amount of a target nucleic acid sequence in a mixture solution can be increased.

Figure 7:
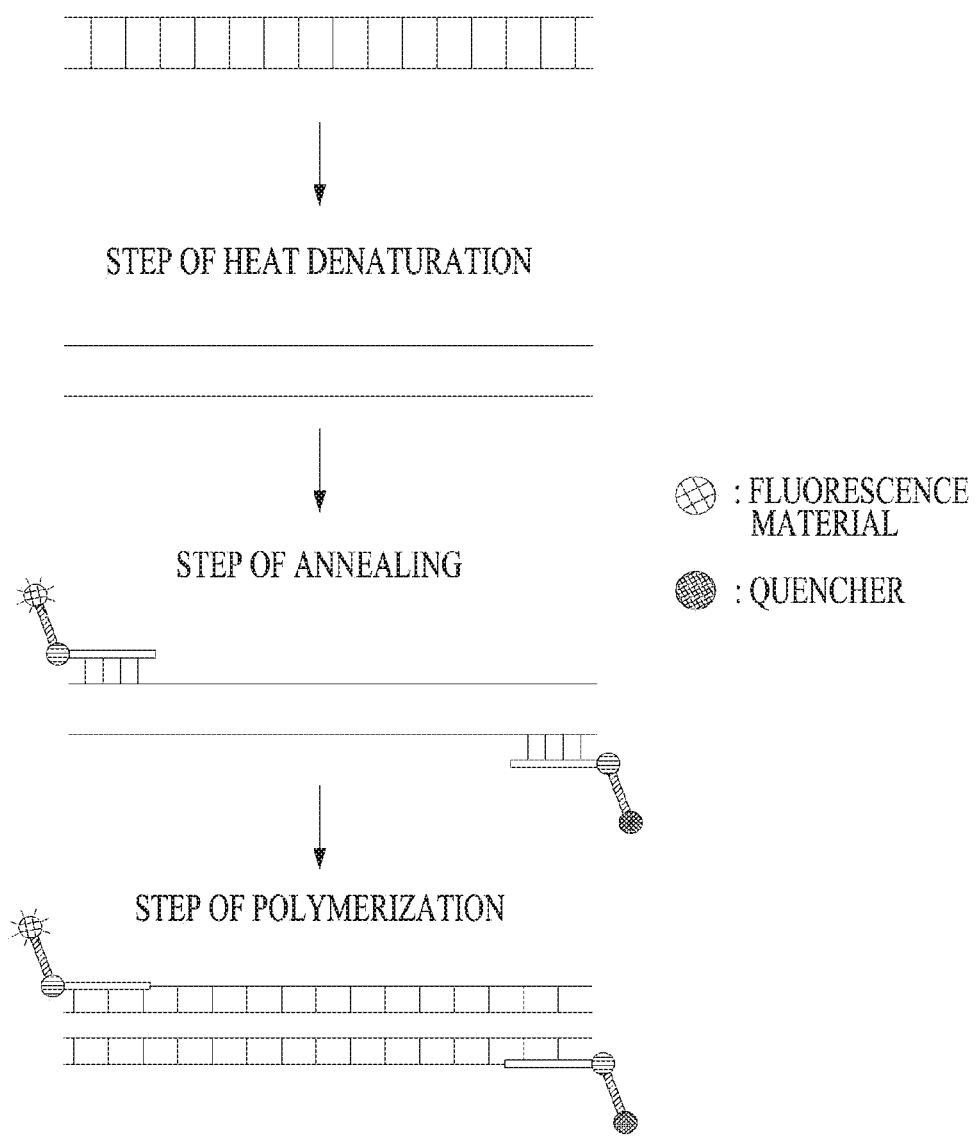

FIGS. 7 and 8 show views illustrating the changes in the binding relationship of a nucleic acid complex pair in PCR reaction according to an embodiment of the present application.

In the denaturation step, the temperature of the mixture solution containing the sample and the nucleic acid complex pair may be raised to separate the complementary hydrogen bond formed between the nucleotides of a double-stranded nucleic acid structure in a sample. In the denaturation step, the double-stranded nucleic acid structure in a sample may be separated into a single-stranded nucleic acid structure. Herein, the double-stranded nucleic acid structure being separated may include the first target nucleic acid sequence TS1 and/or the second target nucleic acid sequence TS2.

In the annealing step, the first determination region 111 or the second determination region 121 may bind to at least a part of the domain among the single-stranded nucleic acid structures. In other words, the first determination region 111 or the second determination region 121 may bind to a domain corresponding to at least one of the first target nucleic acid sequence TS1 or the second target nucleic acid sequence TS2 among the single-stranded nucleic acid structures.

To design an appropriate temperature in the annealing step (hereinafter, annealing temperature), the annealing temperature of the primer domain of the first determination region 111 and the annealing temperature of the primer domain of the second determination region 121 may be considered. The annealing temperature of the primer domain of the first determination region 111 may be determined based on the number of nucleotides, types of nucleotides, etc. The annealing temperature of the primer domain of the second determination region 121 may be determined based on the number of nucleotides, types of nucleotides, etc.

In a method for detecting the presence or absence of a target nucleic acid sequence in a sample according to an embodiment of the present application, when a plurality of types of nucleic acid complex pairs are added into a mixture solution, the annealing temperatures of the first determination region 111 and the second determination region 121 of the plurality of types of nucleic acid complex pairs may be similarly designed. Preferably, with regard to the first nucleic acid complex pair and the second nucleic acid complex pair, the dissociation temperature between the first pairing region 112 and the second pairing region 122 may be designed to be different from each other. And the binding temperature (i.e., annealing temperature) of the first determination region 111 and the second determination region 121 to a target nucleic acid sequence may be designed to be the same.

In the extension (elongation) step, the amplification product for a target material TM including the first target nucleic acid sequence TS1 or the second target nucleic acid sequence TS2 may be produced, by having the first determination region 111 and/or the second determination region 121 as a starting point. Through a one cycle of a PCR reaction, a double-stranded nucleic acid structure including the first target nucleic acid sequence TS1 and/or the second target nucleic acid sequence TS2 may include at least one first nucleic acid complex 110 or second nucleic acid complex 120.

In the denaturation step after one cycle, the double-stranded nucleic acid structure in the mixture solution may be separated into a single-stranded nucleic acid structure. The double-stranded nucleic acid structure formed in the extension step, including at least one nucleic acid complex 100 may be separated into a single-stranded nucleic acid structure.

In the annealing step after one cycle, the first nucleic acid complex 110 or the second nucleic acid complex 120 may bind to the first target nucleic acid sequence TS1 and/or the second target nucleic acid sequence TS2 among the single-strands in the mixture solution. The second nucleic acid complex 120 herein may bind to the single-stranded nucleic acid structure where the first nucleic acid complex 110 is included. In other words, the second nucleic acid complex 120 of a nucleic acid complex pair may bind to the single-stranded nucleic acid structure including the first nucleic acid complex 110 of a nucleic acid complex pair. The first nucleic acid complex 110 of a nucleic acid complex pair may bind to the single-stranded nucleic acid structure including the second nucleic acid complex 120 of a nucleic acid complex pair.

In the extension step after one cycle, the amplification product for a target material TM including the first target nucleic acid sequence TS1 or the second target nucleic acid sequence TS2 may be produced, by having the first determination region 111 or the second determination region 121 as a starting point.

Through at least two cycles of a PCR reaction, the double-stranded nucleic acid structure including the first target nucleic acid sequence TS1 and/or the second target nucleic acid sequence TS2 may include the first nucleic acid complex 110 and/or the second nucleic acid complex 120. At least one double-stranded nucleic acid structure including the first target nucleic acid sequence TS1 and the second target nucleic acid sequence TS2 in the mixture solution may include the first nucleic acid complex 110 and the second nucleic acid complex 120.

In the extension step, when the second nucleic acid complex 120 is bound to the single-stranded nucleic acid structure including the first nucleic acid complex 110, the production of the amplification product for the first pairing region 112 may be blocked by a first blocking region 114 of the first nucleic acid complex 110.

In the extension step, when the first nucleic acid complex 110 is bound to the single-stranded nucleic acid structure including the second nucleic acid complex 120, the production of the amplification product for the first pairing region 112 may be blocked by a second blocking region 124 of the second nucleic acid complex 120.

By the actions of the first blocking region 114 and the second blocking region 124, the first pairing region 112 and the second pairing region 122 may be maintained as a single-stranded nucleic acid structure, and the complementary binding between the first pairing region 112 and the second pairing region 122 may be possible even after the PCR reaction. Therefore the first pairing region 112 and the second pairing region 122 may be utilized as a marker (label) for the presence of a target nucleic acid sequence in a sample.

In a PCR reaction according to an embodiment of the present application, when the signals detected from the first detection region 113 and the second detection region 123 are designed to be extinct by the interaction between the first detection region 113 and the second detection region 123, a signal of a particular wavelength band may be released by the first detection region 113 and the second detection region 123, in the denaturation step, annealing step, and extension step. In an embodiment, the first detection region 113 may contain a fluorescent material, and the second detection region 123 may contain a quenching material for extinguishing the fluorescent signal from the first detection region 113.

In a PCR reaction according to an embodiment of the present application, when the signals detected from the first detection region 113 and the second detection region 123 are designed to be emitted by the interaction between the first detection region 113 and the second detection region 123, a signal of a particular wavelength band may not be released by the first detection region 113 and the second detection region 123, in the denaturation step, annealing step, and extension step. In an embodiment, the first detection region 113 may contain a fluorescent material that provides (or emits) the optical energy of the first wavelength band, and the second detection region 123 may contain a fluorescent material that receives an optical energy of the first wavelength band from the first detection region 113 and provides (or emits) the optical energy of the second wavelength band.

A mixture solution, in which performed at least two cycles, may contain a nucleic acid structure including a first nucleic acid complex 110 and the second nucleic acid complex 120, a nucleic acid structure including the first nucleic acid complex 110, a nucleic acid structure including the second nucleic acid complex 120, and a nucleic acid structure not including the first nucleic acid complex 110 and the second nucleic acid complex 120.

As the number of cycles (i.e., a denaturation step, an annealing step and an extension step) performed in a PCR reaction increases, the percentage of the nucleic acid structure containing the first nucleic acid complex 110 and the second nucleic acid complex 120 in the mixture solution may also increase. The method for detecting targets employing a PCR reaction may be suitable for detecting the presence of a trace amount of DNA in a sample.

Up to now, the binding relationship between a single type of a nucleic acid complex pair and a target nucleic acid sequence corresponding to the nucleic acid complex pair has been explained. Although the binding relationship between the single type of a nucleic acid complex pair and a target nucleic acid sequence was explained for convenience, the binding relationship between a plurality of types of nucleic acid complex pairs and a target nucleic acid sequence may sufficiently and easily be understood to those skilled in the art.

Following FIG. 6, according to an embodiment of the present application, a step of stabilization by lowering the temperature of the mixture solution to a certain temperature may be performed S3000, in which a PCR reaction is completed. The stabilizing step may be performed by lowering the temperature of the mixture solution to 40° C. or below and maintaining the temperature for a certain period of time. In the stabilization step, the complementary binding between the first pairing region 112 and the second pairing region 122 of a nucleic acid complex pair may be performed.

The first pairing region 112 and the second pairing region 122 of a nucleic acid complex pair may perform a complementary binding with each other by the stabilization step. The shape of a nucleic acid structure connected to the first pairing region 112 and the shape of a nucleic acid structure connected to the second pairing region 122 may vary by a complementary binding between the first pairing region 112 and the second pairing region 122 of a nucleic acid complex pair. The shape of a nucleic acid structure connected to the first determination region 111 and the shape of a nucleic acid structure connected to the second determination region 121 may vary by a complementary binding between the first pairing region 112 and the second pairing region 122 of a nucleic acid complex pair.

Figure 9:
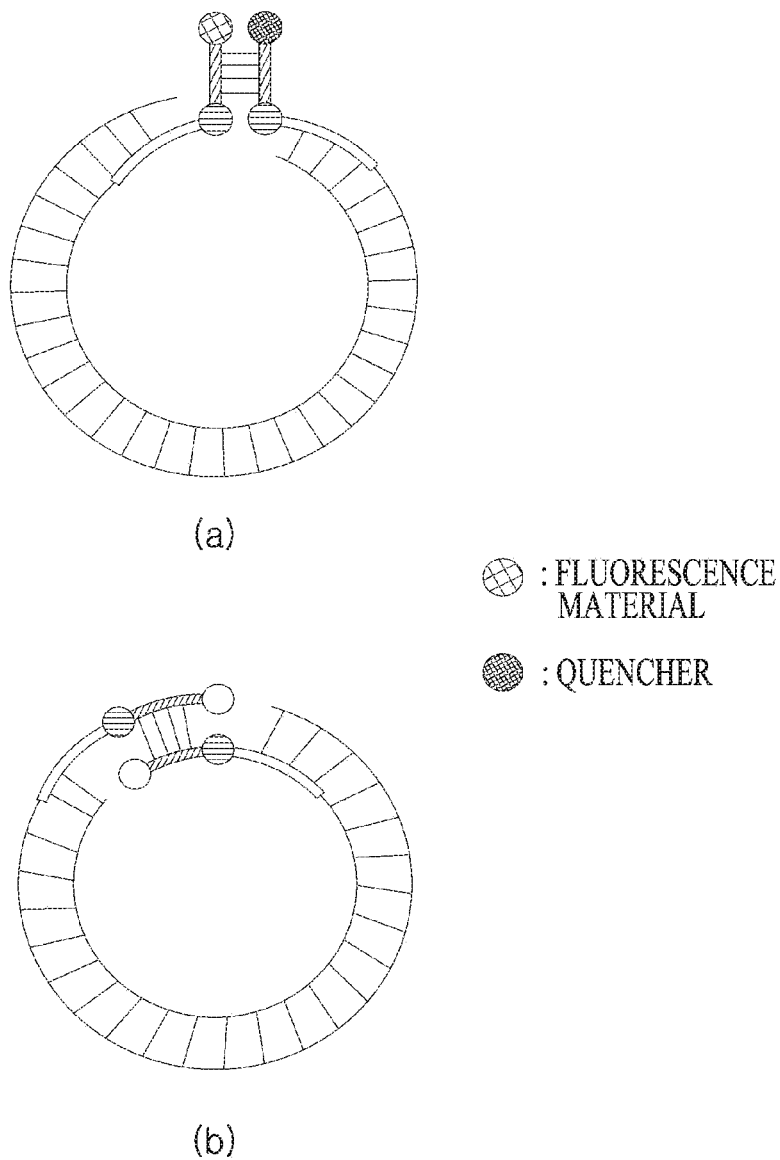
FIG. 9 shows views illustrating the shape of a nucleic acid structure including a nucleic acid complex pair according to an embodiment of the present application.

FIG. 9 shows views illustrating the shape of a nucleic acid structure including the nucleic acid complex pair according to an embodiment of the present application.

A nucleic acid structure including a nucleic acid complex pair may form an quasi-hairpin structure. In the present application, the term "quasi-hairpin structure" may mean a loop structure of double-stranded with any curvature and a stem structure linked to the loop structure. The stem structure comprises two extended strands which are extended from each strand forming the double strands and are bound to each other (see FIG. 9(a)).

A quasi-hairpin structure may be formed when a nucleic acid complex pair is implemented so that a domain adjacent to the first determination region 111 of the first pairing region 112 is complementarily bound to a domain adjacent to the second determination region 121 of the second pairing region 122. An quasi-hairpin structure may be formed when a nucleic acid complex pair is implemented so that a domain adjacent to the second blocking region 114 of the first pairing region 112 is complementarily bound to a domain adjacent to the second blocking region 124 of the second pairing region 122. The first pairing region 112 and the second pairing region 122 herein may form a stem structure. And the first determination region 111, the second determination region 121, the amplification product which is bound to the first determination region 111 and/or the second determination region 121 may form a loop structure.

A nucleic acid structure including a nucleic acid complex pair may form a quasi-circular structure. As used herein, the term "quasi-circular structure" may refer to a loop structure of double-stranded with any curvature and with being opened, thus regarded as an incomplete circle structure (see FIG. 9(b)).

A quasi-circular structure may be formed when a nucleic acid complex pair is implemented so that a domain adjacent to the first determination region 111 of the first pairing region 112 is complementarily bound to a domain spaced apart from the second determination region 121 of the second pairing region 122. A quasi-hairpin structure may be formed when a nucleic acid complex pair is implemented so that a domain adjacent to the first blocking region 114 of the first pairing region 112 is complementarily bound to a domain spaced apart from the second blocking region 124 of the second pairing region 122. The first determination region 111, the second determination region 121, the amplification product which is bound to the first determination region 111 and/or the second determination region 121, the first pairing region 112, and the second pairing region 122 may form a loop structure.

The shape of the above-described nucleic acid structure may vary according to the nucleotide sequences of the first pairing region 112 and the second pairing region 122. The shape of a nucleic acid structure may vary according to the nucleotide sequence from the first blocking region 114 to the first pairing region 112, and the nucleotide sequence from the second blocking region 124 to the second pairing region 122. The shape of a nucleic acid structure may vary according to the nucleotide sequence from the first determination region 111 to the first pairing region 112, and the nucleotide sequence from the second determination region 121 to the second pairing region 122.

Following FIG. 6, according to an embodiment of the present application, a step of melting curve detection for a mixture solution may be performed (S4000), in which a PCR reaction is completed A melting curve detection for a mixture solution performed a step of stabilization may be carried out S4000.

As used herein, the term "melting curve" refers to a graphing of the fluorescent value of a unit cell UC with regard to a temperature within the temperature range including the temperature at which at least two nucleic acid structures formed a complementary binding are separaled. Alternatively, as used herein, the term "melting curve" refers to a graphing of the fluorescent value of a unit cell UC with regard to a temperature within the temperature range including the temperature at which the binding between the first pairing region 112 and the second pairing region 122 is dissociated.

As used herein, the term "unit cell UC" refers to a unit which is a subject for detection. In an embodiment, in a real-time PCR where a PCR reaction and detection are performed for one tube, one tube may correspond to a unit cell.

In a step of melting curve detection, the fluorescent value of a mixture solution included in a unit cell UC may be detected bile increasing the temperature of a mixture solution included in a unit cell UC. In a step of melting curve detection, the fluorescent value of a mixture solution included in a unit cell UC may be detected while increasing the temperature of a mixture solution included in a unit cell UC at a constant rate.

Alternatively, in a step of melting curve detection, the fluorescent value of a mixture solution included in a unit cell UC may be detected while decreasing the temperature of a mixture solution included in a unit cell UC. In a step of melting curve detection, the fluorescent value of a mixture solution included in a unit cell UC may be detected while decreasing the temperature of a mixture solution included in a unit cell UC at a constant rate. In a step of melting curve detection, fluorescent values of a plurality of wavelength bands of a mixture solution included in a unit cell UC may be detected. In a step of melting curve detection, each the fluorescent values of a plurality of wavelength bands of a mixture solution included in a unit cell UC may be detected. In a step of melting curve detection, the fluorescent values for some preset wavelength bands (or some wavelength band groups) may be detected among the fluorescent values of a plurality of wavelength bands of a mixture solution included in a unit cell UC.

In a PCR reaction according to an embodiment of the present application, when the signals detected from the first detection region 113 and the second detection region 123 are designed to be extinct by the interaction between the first detection region 113 and the second detection region 123, a graph where a fluorescent value increases as the temperature increases in a step of melting curve detection may be shown (see FIG. 10(a)).

In a PCR reaction according to an embodiment of the present application, when the signals detected from the first detection region 113 and the second detection region 123 are designed to be emitted by the interaction between the first detection region 113 and the second detection region 123, a graph where a fluorescent value decreases as the temperature increases in a step of melting curve detection may be shown (see FIG. 10(b)).

A step of identifying a dissociation peak value (S5000) may be performed based on the information acquired from the step of melting curve detection (S4000) according to an embodiment of the present application.

As used herein, the term "dissociation peak value" may refer to a temperature at which the complementary binding between the first pairing region 112 and the second pairing region 122 of a nucleic acid complex pair is dissociated. Alternatively, as used herein, the term "dissociation peak value" may refer to a temperature value at a point where the amount of change in fluorescent value is highest or smallest based on the acquired information in the step of melting curve detection. Alternatively, as used herein, the term "dissociation peak value" may refer to a temperature value corresponding to a maximum point or a temperature value corresponding to a minimum point in a differential melting curve graph where the amount of change in fluorescent value with regard to temperature based on the melting curve (see FIGS. 11(a), 11(b)). Alternatively, as used herein, the term "dissociation peak value" may refer to a temperature value at a point where the amount of fluorescence is decreased corresponding to a half of the amount of fluorescence in the amount of altered amount of fluorescence, when there occurred a change in the amount of fluorescence greater than the reference value within a particular temperature range, based on the melting curve. Alternatively, as used herein, the term "dissociation peak value" may refer to a temperature value where the fluorescence value for one type of a nucleic acid complex pair decreases below the predetermined ratio.

According to confirmation of the presence of the nucleic acid complex 100 in a sample according to an embodiment of the present application, a value corresponding to the temperature at which the maximum (or minimum) point is shown in the differential melting curve graph may be a dissociation peak value associated with the first pairing region 112 and the second pairing region 122, wherein the differential melting curve graph is plotted the differential value of fluorescence value for temperature based on the melting curve corresponds. In other words, the value which corresponds to the temperature at which the maximum (or minimum) point is shown in the differential melting curve graph may be a dissociation peak value associated with the nucleic acid complex pair.

In confirming the presence of a target nucleic acid sequence in a target using a nucleic acid complex 100 according to an embodiment of the present application, when there is a dissociation peak value such that the amount of change in fluorescence confirmed with regard to temperature based on information acquired from the melting curve detection exceeds any reference value, it may be confirmed that the target nucleic acid sequence associated with a dissociation peak value is present in the sample.

The dissociation peak value according to an embodiment of the present application may be determined based on the dissociation of a binding between the first pairing region 112 and the second pairing region 122. However, the dissociation peak value confirmed experimentally may be a value greater than the temperature value (i.e., the dissociation temperature of a binding between the first pairing region 112 and the second pairing region 122) which is calculated by a known formula for obtaining the Tm value.

Specifically, when the first pairing region 112 and the second pairing region 122 include 7mer C-G, the Tm value may be calculated as 28° C. by applying Tm=4*(the number of C-G)+2*(the number of A-T). Even when the experimental correction value is applied to the calculated Tm value, the Tm value may be calculated to be in the range of 25° C. to 30° C. when the first pairing region 112 and the second pairing region 122 include 7mer C-G.

However, when the dissociation peak value was measured using a nucleic acid complex 100 according to an embodiment of the present application pair, it was confirmed that the dissociation peak value was about 40° C. when the first pairing region 112 and the second pairing region 122 include 7mer C-G.

With regard to the dissociation peak value according to an embodiment of the present application, 1) the position of a first detection region 113 or a second detection region 123; 2) the types of unit nucleic acids involved in the binding between the first pairing region 112 and the second pairing region 122; 3) the types of base of unit nucleic acids involved in the binding between the first pairing region 112 and the second pairing region 122; 4) the number of nucleotides involved in the binding between the first pairing region 112 and the second pairing region 122; 5) the complementary sequence arrangement of nucleotides between the first pairing region 112 and the second pairing region 122 (e.g., the binding direction between the first pairing region 112 and the second pairing region 122); and 6) the types of the first detection region 113 and the second detection region 123 may have an affection.

According to an embodiment of the present application, a plurality of types of targets may be detected in one unit cell UC using a plurality of types of nucleic acid complex pairs. According to an embodiment of the present application, a plurality of types of targets per one fluorescent channel may be detected in one unit cell UC using a plurality of types of nucleic acid complex pairs. According to an embodiment of the present application, a plurality of types of targets per one fluorescent channel may be detected in one unit cell UC using different dissociation peak values of a plurality of types of nucleic acid complex pairs.

The plurality of types of nucleic acid complex pairs for enabling the detection of a plurality of types of targets per one fluorescent channel may be respectively designed so as to have different dissociation peak values by appropriately using the factors described above, etc.

In an embodiment, each of the dissociation peak values associated with two types of nucleic acid complex pairs including the same first pairing region 112 and second pairing region 122 may be differently implemented by changing the position of at least one fluorescent material included in a nucleic acid complex pair. In another embodiment, a temperature having a higher dissociation peak value associated with a nucleic acid complex pair which has relatively many number of nucleotides involved in the complementary binding between the first pairing region 112 and the second pairing region 122 may be implemented by extending the number of nucleotides involved in the first pairing region 112 and the second pairing region 122 the complementary binding. In still another embodiment, a dissociation peak value associated with a nucleic acid complex pair may be implemented to have a higher temperature associated with a nucleic acid complex pair having an increased C-G content of nucleotides involved in the complementary binding between the first pairing region 112 and the second pairing region 122 by increasing the C-G content of nucleotides involved in the complementary binding between the first pairing region 112 and the second pairing region 122. In still another embodiment, each dissociation peak value associated with two types of nucleic acid complex pairs including the same first pairing region 112 and second pairing region 122 may be differently implemented by changing the direction of the complementary binding between the first pairing region 112 and the second pairing region 122.

In order to enable detection of a plurality of types of targets per fluorescent channel in one unit cell UC, a plurality of dissociation peak values may be assigned to a nucleic acid complex pair corresponding to a target nucleic acid sequence different from each other.

When a PCR reaction is performed using a first nucleic acid complex pair designed to have a dissociation peak value at a first temperature and a second nucleic acid complex pair designed to have a dissociation peak value at a second temperature, the presence or absence of the first target nucleic acid sequence TS1 and the second target nucleic acid sequence TS2 of the first nucleic acid complex pair may be confirmed based on whether or not a dissociation peak value is confirmed at the first temperature, and the presence or absence of a first target nucleic acid sequence TS1 and the second target nucleic acid sequence TS2 of the second nucleic acid complex pair may be confirmed based on whether or not a dissociation peak value is confirmed at the second temperature.

FIG. 12 shows views illustrating the melting curve with regard to one fluorescent channel according to an embodiment of the present application (see FIG. 12($a$)), and views illustrating the differential melting curve with regard to one fluorescent channel according to an embodiment of the present application (see FIG. 12($b$)).

When the sample contains the target sequence of the first nucleic acid complex pair and the target sequence of the second nucleic acid complex pair, the maximum or minimum point may be confirmed at a point corresponding to a first temperature (i.e. a dissociation peak value associated with the first nucleic acid complex pair) and a second temperature (i.e. a dissociation peak value associated with the second nucleic acid complex pair) of a graph of the change in the amount of fluorescence versus temperature (i.e., a graph of a differential melting curve).

When the maximum point or the minimum point is confirmed at the first temperature and the second temperature, the presence of a target nucleic acid associated with the first nucleic acid complex pair and a target nucleic acid associated with the second nucleic acid complex pair may be confirmed.

The temperature difference between the first temperature and the second temperature may be designed within a range that can be identified through a device. Preferably, a plurality of types of nucleic acid complex pairs can be designed such that the temperature difference between the first temperature and the second temperature is in the range of 1° C. to 10° C.

When the presence of a target nucleic acid sequence in a sample can be confirmed using a nucleic acid complex 10 according to an embodiment of the present application pair, the presence of a target nucleic acid sequence associated with the nucleic acid complex pair in a sample may be confirmed based on the detection of a dissociation peak value associated with the nucleic acid complex pair.

A dissociation peak value may be regulated by the nucleotide sequence of the first pairing region 112 and the second pairing region 122 of a nucleic acid complex pair. Accordingly, when the presence of a target nucleic acid sequence is confirmed using the nucleic acid complex 100 according to an embodiment of the present application pair, a plurality of types of target detection may be performed by adjusting the sequence design of the first pairing region 112 and the second pairing region 122 which do not need to bind to a target nucleic acid sequence, by comparing the results with those of other probes used to confirm the presence or absence of a target nucleic acid sequence through a melting curve analysis, and thus there is an advantage in that a simpler and more flexible design can be derived.

Additionally, according to the detection of the presence of a target nucleic acid sequence in a sample using the nucleic acid complex 100 according to an embodiment of the present application pair, since there is little need to use other probes used to confirm the presence of a target nucleic acid sequence, it may obtain a sufficient efficiency without PCR using the asymmetric method, and as a result, the advantage of increasing the detection sensitivity can be obtained.

The PCR kit containing the nucleic acid complex 100 disclosed in the present application may contain two or more nucleic acid complex pairs. The PCR kit can contain at least two different nucleic acid complex pairs. The PCR kit may further contain at least one among an enzyme and nucleotide fragments involved in the polymerization, a co-enzyme involved in a PCR reaction, and a buffer solution to provide optimal pH and/or salt concentration for a PCR reaction.

A PCR kit may be implemented in the form of a composition containing at least one material (e.g., a nucleic acid complex pair), and a plurality of containers in a single container to be sold A PCR kit may be implemented in the form of a single container in the form of a composition containing at least one material to be sold. A PCR kit may be implemented in such a form that at least one material is sold in a container in a dried state to be sold.

A PCR kit may contain up to X a nucleic acid complex pair. The X value may rely on a temperature section that can detect the difference ($\Delta T$) and signals between dissociation peak values due to the dissociation of a binding between the first pairing region 112 and the second pairing region 122 of a plurality of types of the nucleic acid complex 100. The X value may depend on the number of wavelength band groups that the device can identify. The value of X may depend on the type of the signal material contained in a nucleic acid complex pair.

For example, when the minimum temperature at which the signal can be measured is 40° C., the maximum temperature is 55° C., and the $\Delta T$ is 3° C., (55-40)/3=5 becomes the number of target types that can be detected through identification by one fluorescence channel. And when the number of wavelength band groups that can be identified by the device is 5, the X value can be 25. That is, when a composition for PCR including the nucleic acid complex 100 according to an embodiment of the present application pair is used, it is possible to identify the presence of 25 different targets in one tube.

The first detection region 113 and the second detection region 123 according to an embodiment of the present application, when the first detection region 113 and the second detection region 123 interact with each other (i.e., when the second detection region 123 is positioned within an effective interactive distance of the first detection region 113), may be designed such that the signals released from the first detection region 113 and the second detection region 123 are extinct (hereinafter, signal extinction method). Alternatively, the first detection region 113 and the second detection region 123 according to an embodiment of the present application, when the first detection region 113 and the second detection region 123 interact with each other (i.e., when the second detection region 123 is positioned within an effective interactive distance of the first detection region 113), may be designed such that the signals released from the first detection region 113 and the second detection region 123 are emitted (hereinafter, signal emission method).

When a plurality of types of nucleic acid complex pairs are used in a PCR reaction, at least the first nucleic acid complex pair and the second nucleic acid complex pair may be designed in the same manner or in a different method.

When an X number or less types of nucleic acid complex pairs are included, a PCR kit may consist of an X/2 number of nucleic acid complex pairs designed in a signal extinction method and an X2 number of nucleic acid complex pairs designed in a signal emission method. In this case, the number of types of targets that can be detected in one tube may be increased. When the nucleic acid complex pair is designed in a total of two types of a signal extinction method and a signal emission method, the X value associated with the number of types of targets that can be detected under the same conditions (e.g., the minimum temperature at which a signal can be detected is 40° C., the maximum temperature is 55° C., and the $\Delta T$ is 3° C.) may be increased twice (25*2=50).

1.1.2 Use in Digital PCR

One of the fields where a PCR reaction is used is a digital PCR. In the digital PCR field, the size of the unit cell UC from which a signal is to be detected is small, and a highly sensitive and precise target detection can be achieved. In an embodiment, the digital PCR may be used to detect nucleic acid strands of a subject infected with pathogens having a negligible amount, nucleic acid strands classified as mutations, etc.

Figure 13:
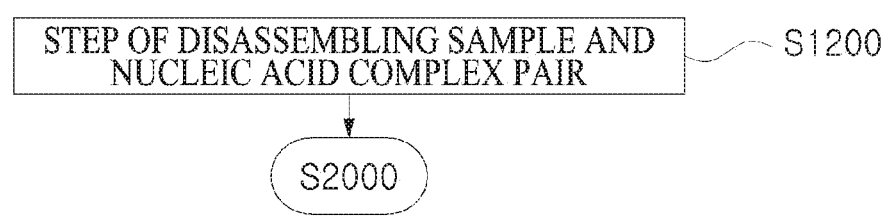
FIG. 13 shows a view illustrating the steps performed where a nucleic acid complex pair is used in digital PCR according to an embodiment of the present application.

FIG. 13 shows a view illustrating the step performed when a nucleic acid complex pair is used in digital PCR according to an embodiment of the present application.

At least one type of a nucleic acid complex pair used in digital PCR may be similar to at least one type of a nucleic acid complex pair that is used in the general PCR described above. In other words, at least one type of a nucleic acid complex pair used in digital PCR may include the first nucleic acid complex 110 and the second nucleic acid complex 120, where the first nucleic acid complex 110 may include a first determination region 111, a first pairing region 112, a first detection region 113, and/or a first blocking region, and the second nucleic acid complex 120 may include a second determination region 121, a second pairing region 122, a second detection region 123, and/or a second blocking region, respectively.

The particular feature or specific behavior of each constituting element of the nucleic acid complex pair have been already described in association with the nucleic acid complex pair applied in general PCR, repeated description will be omitted, and thus the configuration, operation, and/or other embodiments that are changed in digital PCR will be described.

According to an embodiment of the present application, for confirmation of the presence of a target nucleic acid sequence in a sample in digital PCR, a step of distributing a sample and a nucleic acid complex pair into a unit cell UC (e.g., one well) may be performed before performing a PCR reaction for a unit cell UC (S2000).

A specific embodiment to implement the distribution of a mixture solution containing a sample and a nucleic acid complex pair in a unit cell UC may vary depending on which method among the well method and droplet method of digital PCR is applied.

First, digital PCR may be performed according to a method where a sample, etc. are dispensed into a plate where a plurality of wells are formed, a PCR reaction is performed, and fluorescent values are detected by having each well as a unit cell UC (hereinafter, well method, see FIG. 14(*a*)).

The sample and a nucleic acid complex pair may be sequentially dispensed into each unit cell UC (i.e., well). After dispensing the sample into each unit cell UC, a nucleic acid complex pair may be dispensed into each unit cell UC. The sample and a nucleic acid complex pair may be dispensed into each unit cell UC in the form of dispensing the mixture solution containing the sample and the nucleic acid complex pair.

The method of dispensing a sample, etc. into each unit cell UC may be various. In an embodiment, the sample, etc. may be dispensed into each unit cell UC through the method using a microfluidic channel. In another embodiment, the sample, etc. may be dispensed into each unit cell UC in the form of smearing a sample or the like on a plate implemented as an open top of the well.

Second, digital PCR may be performed according to a method where a sample is dispensed in the form of a plurality of droplets, a PCR reaction is performed for the plurality of droplets, and fluorescent values for each of the plurality of droplets are detected (hereinafter, droplet method, see FIG. 14(*b*)).

Each of the sample and the nucleic acid complex pair may be dispensed by being implemented in the form of a droplet smaller than each unit cell UC and incorporated before a PCR reaction. The sample and the nucleic acid complex pair may be dispensed into each unit cell UC in the form of dispensing the mixture solution containing the sample and the nucleic acid complex pair into a size of a unit cell UC.

In an embodiment of the present application, in the process of dispensing the nucleic acid complex pair into each unit cell UC, there may occur a problem that the first nucleic acid complex 110 and the second nucleic acid complex 120 may not be dispensed uniformly. Specifically, in cases where the first nucleic acid complex 110 may be dispensed more in a particular unit cell UC compared to the second nucleic acid complex 120, the second nucleic acid complex 120 may be dispensed more in a particular unit cell UC compared to the first nucleic acid complex 110, or any of the first nucleic acid complex 110 or second nucleic acid complex 120 is not dispensed at all in a particular unit cell UC, there may occur a problem that the presence of the target nucleic acid sequence cannot be accurately confirmed while the reagents are being consumed.

To solve the problem, the may be used in digital PCR field where the complementary binding between the first pairing region 112 and the second pairing region 122 is formed, before dispensing the nucleic acid complex pair into each unit cell UC.

Figure 15:
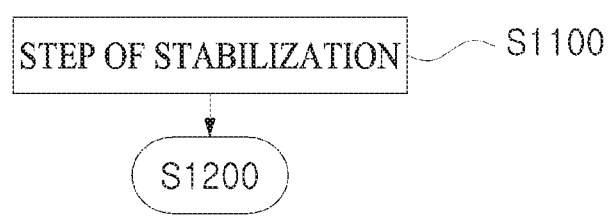
FIG. 15 shows a flowchart illustrating a process of performing a stabilization step before the dispensing step according to an embodiment of the present application.

FIG. 15 shows a flowchart illustrating a process of performing a stabilization step before the dispensing step according to an embodiment of the present application.

A step of stabilization inducing the binding between the first pairing region 112 and the second pairing region 122 of a nucleic acid complex pair may be performed before dispensing the sample and the nucleic acid complex pair into each unit cell UC (S1200). The step of stabilization may be performed in the form of maintaining for a predetermined period of time after lowering the temperature of the mixture solution to 40° C. or lower.

According to an embodiment of the present application, the first nucleic acid complex 110 may at least include a forward primer and a first pairing region 112, and the second nucleic acid complex 120 may include at least a reverse primer and a second pairing region 122. The nucleic acid complex pair may be stabilized in a form where the first pairing region 112 and the second pairing region 122 are complementarily bound to each other, before the nucleic acid complex pair is dispensed into each unit cell UC. When a nucleic acid complex pair containing stabilized first pairing region 112 and second pairing region 122 is dispensed into each unit cell UC, it may prevent either one of the forward primer or reverse primer from dispensing into the unit cells UC relatively higher compared to the other. Ultimately, when a nucleic acid complex pair containing stabilized first pairing region 112 and second pairing region 122 is dispensed into each unit cell UC, it may be possible to dispense the nucleic acid complex pair such that the ratio between the forward primer and the reverse primer is in a 1:1 ratio.

When the nucleic acid complex 100 according to an embodiment of the present application pair is used in digital PCR, a mixture solution containing the sample and the nucleic acid complex pair included in the unit cell UC may be used in a PCR reaction for the amplification of a target nucleic acid sequence (S2000) and/or the step of stabilization (S3000) where the temperature of the mixture solution is lowered to any temperature or less. The steps S2000 and S3000 may be performed in a manner similar to the general PCR.

However, in a specific embodiment, a step of melting curve detection (S4000) may be altered compared to that a nucleic acid complex pair is used in general PCR.

Specifically, in the well method, the temperature of a mixture solution (at least, including a sample and a nucleic acid complex pair) included in a unit cell UC may be regulated by adjusting the temperature of a plate where a plurality of wells are formed. The temperature of a plate may be regulated by adjusting the temperature of a thermocycler which is implemented in a domain where the plate is disposed.

However, in the case of digital PCR by the droplet method, there is a problem in that the detection of a melting curve from the current device where the fluorescent value of the unit cell UC that transports a microfluidic channel is detected is not simple. To solve the problem, a plurality of unit cells UC in the shape of a droplet may be evenly divided in the microfluidic lane LN formed on a plate, by using the plate where the microfluidic lane LN are formed.

FIG. 16 shows views illustrating a method for performing the detection of melting curves in digital PCR according to an embodiment of the present application.

A plurality of microfluidic lanes LN may be formed on the plate for melting curve detection according to an embodiment of the present application (see FIG. 16(a)). A plurality of unit cells UC may be evenly divided in each of the microfluidic lane LN of the plate where a plurality of microfluidic lanes LN are formed. A single microfluidic lane LN may be formed on the plate for melting curve detection according to an embodiment of the present application (see FIG. 16(b)). A plurality of unit cells UC may be aligned in a row on a plate where a single microfluidic lane LN is formed.

A microfluidic lane LN having a sufficient size for the entrance of the droplet of one unit cell UC may be formed on the plate for melting curve detection according to an embodiment of the present application. In at least one microfluidic lane LN, the width*length*depth may be determined based on the radius of the droplet. Additionally, it should be considered in determining the width*length*depth that, with regard to at least one microfluidic lane LN, the radius of the droplet may be altered according to the volume, temperature, or pressure.

Conclusively, according to an embodiment of the present application, the melting curve per each unit cell UC can be detected in digital PCR of the well method or droplet method, and a dissociation peak value can be confirmed based on the information associated with melting curve.

Accordingly, there is an advantage in that the presence of a target nucleic acid sequence in a sample can be confirmed even in the digital PCR method by using the nucleic acid complex pair disclosed in the present application.

Additionally, there is an advantage in that the presence of a plurality of types of target nucleic acid sequences in a sample can be confirmed even in digital PCR method by using a plurality of types of the nucleic acid complex pairs disclosed in the present application. In other words, there is an advantage in that the presence of a plurality of types of target nucleic acid sequences in a sample per fluorescent channel can be confirmed even in digital PCR method by using a plurality of types of the nucleic acid complex pairs including a labeling detected by the same fluorescence disclosed in the present application.

<Detection of Presence of Target Nucleic Acid by Utilizing Nucleic Acid Complex Pair and Probe Complex 200>

1. Defection of Target Nucleic Acid Sequence by Utilizing Nucleic Acid complex Pair and Probe Complex 200

Figure 17:
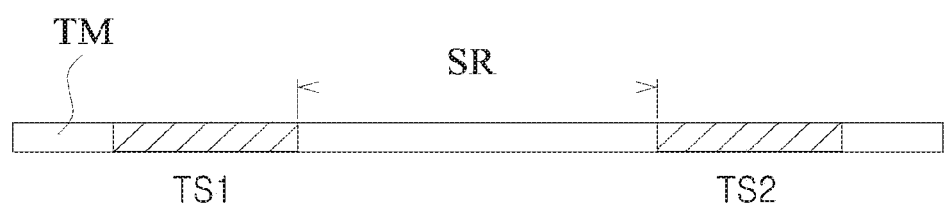
FIG. 17 shows a view illustrating an excess domain to a target material TM according to an embodiment of the present application.

FIG. 17 shows a view illustrating an excess domain to a target material TM according to an embodiment of the present application.

When the presence of a target nucleic acid sequence is confirmed by using the nucleic acid complex pair according to an embodiment of the present application in a PCR reaction, the nucleic acid complex pair becomes bound to the first target nucleic acid sequence TS1 and the second target nucleic acid sequence TS2 of the target material TM. Accordingly, the remaining domains among the domains used in the PCR reaction for the confirmation of presence of a target nucleic acid sequence (e.g., between the first target nucleic acid sequence TS1 and the second target nucleic acid sequence TS2), will remain as the excess domains excluding the first target nucleic acid sequence TS1 and the second target nucleic acid sequence TS2. Accordingly, the probe complex 20 used for detection of targets may be able to bind to at least a part of the excess domains (SR), and as a result, the target detection methods according to the first labeling method (e.g., a target detection method using a nucleic acid complex pair) and a second labeling method (e.g., a target detection method using a probe complex 200) may be applied simultaneously.

For example, the second labeling method may be a Taqman method, molecular beacon method, TOCE method, PNA probe method, or a combination thereof, and additionally, the second labeling method is not limited to these methods.

According to the labeling method disclosed by the present application, target nucleic acid sequences, which are close to 2-20 folds compared to the existing method, can be confirmed through one PCR tube.

For the detection of a target nucleic acid sequence in a sample using the first and second labeling methods, there may be required a design process that prevents the overlap between the dissociation peak value associated with the first labeling method and the dissociation peak value associated with the second labeling method. As used herein, the term "a dissociation peak value" may refer to a temperature value corresponding to the maximum point or a temperature value corresponding to the minimum point based on the melting curve, in a differential melting curve graph showing the amount of changes in fluorescent values associated with temperature.

Figure 18:
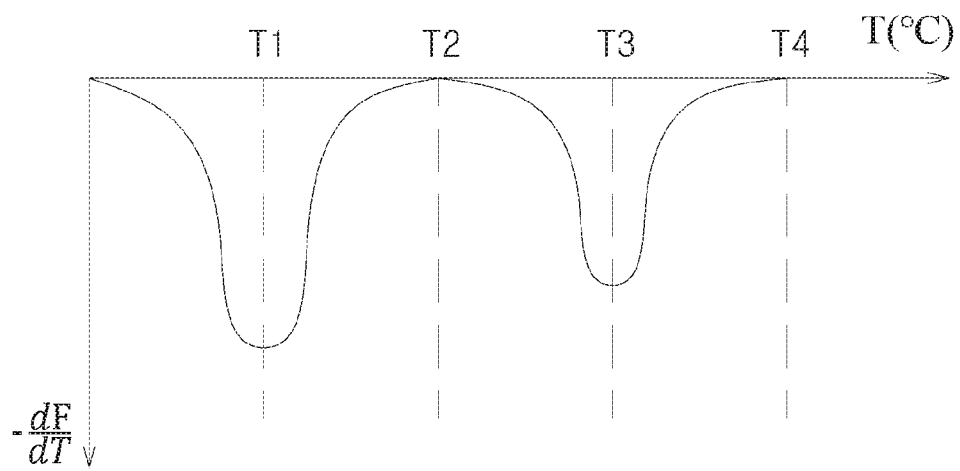
FIG. 18 shows a view illustrating the dissociation peak values with regard to a first labeling method and a second labeling method.

FIG. 18 shows a view illustrating the dissociation peak values with regard to the first labeling method and the second labeling method.

According to an embodiment of the present application, when the dissociation peak values that can be detected by a device, which can detect the fluorescent value of a mixture solution provided and confirm the dissociation peak values, are a total of 4 (i.e., T1, T2, T3, and T4), the nucleic acid complex pair and a probe complex 200 may be designed such that a dissociation peak value included in the first temperature section are assigned to the first labeling method and a dissociation peak value included in the second temperature section are assigned to the second labeling method. In an embodiment. T1 and T2 may be assigned to dissociation peak values associated with the first labeling method, whereas T3 and T4 may be assigned to dissociation peak values associated with the second labeling method.

Alternatively, according to another embodiment of the present application, when the dissociation peak values that can be detected by a device, which can detect the fluorescent value of a mixture solution provided and confirm the dissociation peak values, are a total of 4 (i.e., T1, T2. T3, and T4), the nucleic acid complex pair and a probe complex 200 may be designed such that some of the dissociation peak values included in the first temperature section are assigned to the first labeling method and other dissociation peak values which are not assigned to the first labeling method are assigned to the second labeling method. In an embodiment, T1 and T3 may be assigned to the first labeling method, and T2 and T4 may be assigned to the second labeling method.

In a more specific embodiment, when the minimum temperature that signals can be detected is 35° C., the maximum temperature that signals can be detected is 60° C., and the ΔT is 5° C., the temperatures that signals can be detected per one fluorescence channel may be 35° C., 40° C., 45° C., 50° C., 55° C., and 60C, thus a total number of dissociation peak values that can be used for detection is 6.

In particular, in an embodiment, 35° C., 40° C., and 45° C. may be assigned to the nucleic acid complex pair according to the first labeling method, 50° C., 55° C., and 60° C. may be assigned to the probe complex 200 according to the second labeling method. When the probe-binding domain PR of the probe complex 200 binds to a target DNA in a PCR reaction, the above-described design provides an advantage in that, considering the annealing temperature of a PCR reaction, each of 50° C., 55° C., 60° C. can be assigned as the dissociation peak value associated with the probe complex 200 and the remaining 35° C., 40° C., and 45° C. can each be assigned as the dissociation peak value associated with the nucleic acid complex pair, by using the nucleic acid complex pair and the probe complex 200 designed as described above.

In another embodiment, the nucleic acid complex pair may be designed such that 35° C., 45° C., and 55° C. are assigned as the dissociation peak values corresponding to the first labeling method, and the probe complex 200 may be designed such that 40° C., 50° C. and 60° C. are assigned as the dissociation peak values corresponding to the second labeling method. When it is difficult that the distinguishable difference between the adjacent dissociation values is designed to be under 5° C. in designing a plurality of types of nucleic acid complex pairs and/or a plurality of types of the probe complex 200, in the above design in which the difference between the adjacent dissociation peak values is 10° C. makes possible that relatively more temperatures can be used as the dissociation peak values.

Figure 19:
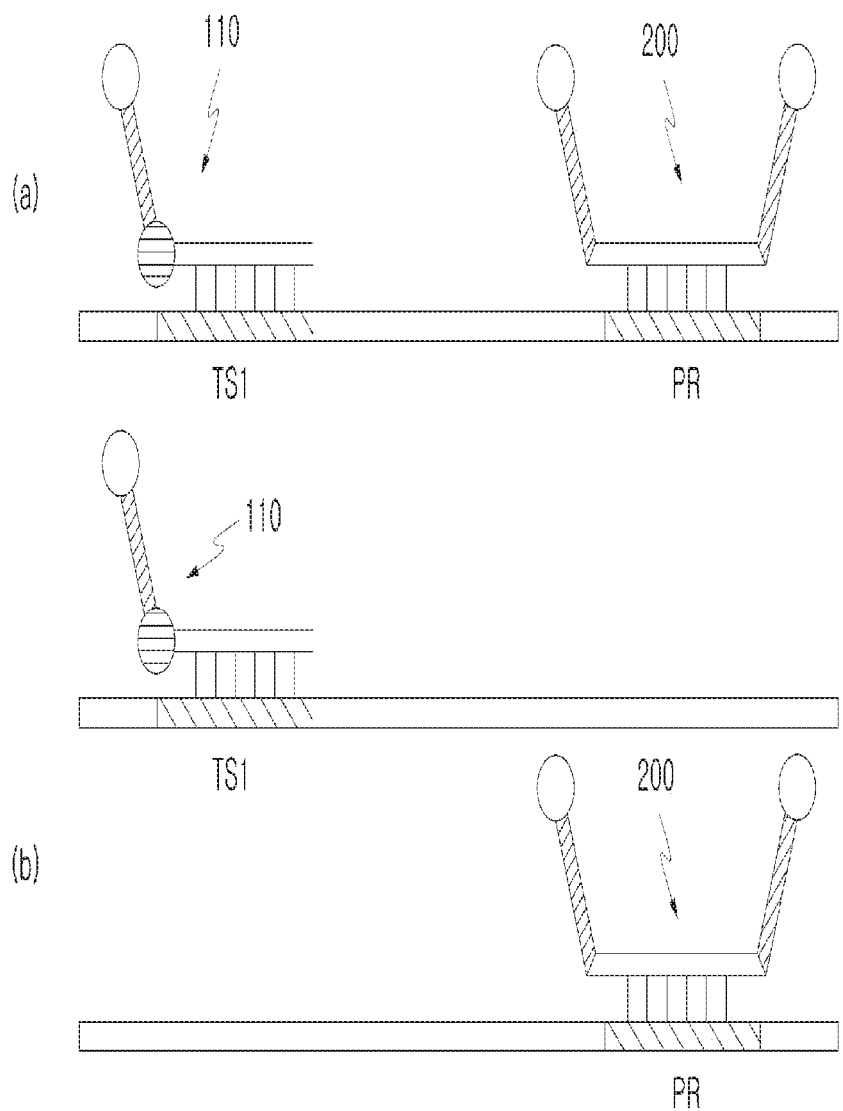
FIG. 19 shows views illustrating the binding between a nucleic acid complex pair and/or a probe complex 200 and a target material TM according to an embodiment of the present application.

FIG. 19 shows views illustrating the binding between a nucleic acid complex pair and/or a probe complex 200 and a target material TM according to an embodiment of the present application.

According to an embodiment of the present application, when a nucleic acid complex pair is used as a primer associated with the amplification product for the probe-binding domain PR to which the probe complex 200 binds, the number of targets from which the target nucleic acid sequences can be detected using the nucleic acid complex pair and the probe complex 200 may be a number of multiplying (the number of types of targets (N1) from which the target nucleic acid sequences can be detected using the probe complex 200) by (the number of types of targets (N2) from which the target nucleic acid sequences can be detected using the nucleic acid complex pair) (see 19(a)).

In a more specific embodiment, when the temperatures of the dissociation peak values assigned to the first labeling method are 40° C., 45° C., and 50C and the temperatures of the dissociation peak values assigned to the second labeling method are 55° C., 60° C., and 65° C., and a total of 5 fluorescent wavelength bands (or fluorescent materials) can be detected, if a nucleic acid complex pair is used as a primer associated with the amplification product for the probe-binding domain PR to which the probe complex 200 binds, a total of 225 targets ((3*5)*(3*5)=225) can be detected by performing the detection of target nucleic acid sequences using the nucleic acid complex pair and the probe complex 200.

TABLE 1

| Target ID | 1st Labeling | | | | | 2nd Labeling | | | | |
|---|---|---|---|---|---|---|---|---|---|---|
| | FAM | HEX | ROX | Cy5 | 705 | FAM | HEX | ROX | Cy5 | 705 |
| 1 | 40 | | | | | 55 | | | | |
| 2 | | 40 | | | | | 55 | | | |
| 3 | | | 40 | | | | | 55 | | |
| 4 | | | | 40 | | | | | 55 | |
| 5 | | | | | 40 | | | | | 55 |
| 6 | 40 | | | | | | 55 | | | |
| 7 | | 40 | | | | | | 55 | | |
| 8 | | | 40 | | | | | | 55 | |
| 9 | | | | 40 | | | | | | 55 |
| 10 | | | | | 40 | 55 | | | | |
| 11 | 40 | | | | | | | 55 | | |
| 12 | | 40 | | | | | | | 55 | |
| 13 | | | 40 | | | | | | | 55 |
| 14 | | | | 40 | | 55 | | | | |
| 15 | | | | | 40 | | 55 | | | |
| 16 | 40 | | | | | | | | 55 | |
| 17 | | 40 | | | | | | | | 55 |
| 18 | | | 40 | | | 55 | | | | |
| 19 | | | | 40 | | | 55 | | | |
| 20 | | | | | 40 | | | 55 | | |
| 21 | 40 | | | | | | | | | 55 |
| 22 | | 40 | | | | 55 | | | | |
| 23 | | | 40 | | | | 55 | | | |
| 24 | | | | 40 | | | | 55 | | |
| 25 | | | | | 40 | | | | 55 | |
| 26 | 40 | | | | | 60 | | | | |
| 27 | | 40 | | | | | 60 | | | |
| 28 | | | 40 | | | | | 60 | | |
| 29 | | | | 40 | | | | | 60 | |
| 30 | | | | | 40 | | | | | 60 |
| 31 | 40 | | | | | | 60 | | | |
| 32 | | 40 | | | | | | 60 | | |
| 33 | | | 40 | | | | | | 60 | |
| 34 | | | | 40 | | | | | | 60 |
| 35 | | | | | 40 | 60 | | | | |
| 36 | 40 | | | | | | | 60 | | |
| 37 | | 40 | | | | | | | 60 | |
| 38 | | | 40 | | | | | | | 60 |
| 39 | | | | 40 | | 60 | | | | |
| 40 | | | | | 40 | | 60 | | | |
| 41 | 40 | | | | | | | | 60 | |
| 42 | | 40 | | | | | | | | 60 |
| 43 | | | 40 | | | 60 | | | | |
| 44 | | | | 40 | | | 60 | | | |
| 45 | | | | | 40 | | | 60 | | |
| 46 | 40 | | | | | | | | | 60 |
| 47 | | 40 | | | | 60 | | | | |
| 48 | | | 40 | | | | 60 | | | |
| 49 | | | | 40 | | | | 60 | | |
| 50 | | | | | 40 | | | | 60 | |
| 51 | 40 | | | | | 65 | | | | |
| 52 | | 40 | | | | | 65 | | | |
| 53 | | | 40 | | | | | 65 | | |
| 54 | | | | 40 | | | | | 65 | |
| 55 | | | | | 40 | | | | | 65 |
| 56 | 40 | | | | | | 65 | | | |
| 57 | | 40 | | | | | | 65 | | |
| 58 | | | 40 | | | | | | 65 | |
| 59 | | | | 40 | | | | | | 65 |
| 60 | | | | | 40 | 65 | | | | |
| 61 | 40 | | | | | | | 65 | | |
| 62 | | 40 | | | | | | | 65 | |
| 63 | | | 40 | | | | | | | 65 |
| 64 | | | | 40 | | 65 | | | | |
| 65 | | | | | 40 | | 65 | | | |
| 66 | 40 | | | | | | | | 65 | |
| 67 | | 40 | | | | | | | | 65 |
| 68 | | | 40 | | | 65 | | | | |
| 69 | | | | 40 | | | 65 | | | |
| 70 | | | | | 40 | | | 65 | | |
| 71 | 40 | | | | | | | | | 65 |

TABLE 1-continued

| Target ID | 1st Labeling | | | | | 2nd Labeling | | | | |
|---|---|---|---|---|---|---|---|---|---|---|
| | FAM | HEX | ROX | Cy5 | 705 | FAM | HEX | ROX | Cy5 | 705 |
| 72 | | 40 | | | | 65 | | | | |
| 73 | | | 40 | | | | 65 | | | |
| 74 | | | | 40 | | | | 65 | | |
| 75 | | | | | 40 | | | | 65 | |
| 76 | 45 | | | | | 55 | | | | |
| 77 | | 45 | | | | | 55 | | | |
| 78 | | | 45 | | | | | 55 | | |
| 79 | | | | 45 | | | | | 55 | |
| 80 | | | | | 45 | | | | | 55 |
| 81 | 45 | | | | | | 55 | | | |
| 82 | | 45 | | | | | | 55 | | |
| 83 | | | 45 | | | | | | 55 | |
| 84 | | | | 45 | | | | | | 55 |
| 85 | | | | | 45 | 55 | | | | |
| 86 | 45 | | | | | | | 55 | | |
| 87 | | 45 | | | | | | | 55 | |
| 88 | | | 45 | | | | | | | 55 |
| 89 | | | | 45 | | 55 | | | | |
| 90 | | | | | 45 | | 55 | | | |
| 91 | 45 | | | | | | | | 55 | |
| 92 | | 45 | | | | | | | | 55 |
| 93 | | | 45 | | | 55 | | | | |
| 94 | | | | 45 | | | 55 | | | |
| 95 | | | | | 45 | | | 55 | | |
| 96 | 45 | | | | | | | | | 55 |
| 97 | | 45 | | | | 55 | | | | |
| 98 | | | 45 | | | | 55 | | | |
| 99 | | | | 45 | | | | 55 | | |
| 100 | | | | | 45 | | | | 55 | |
| 101 | 45 | | | | | 60 | | | | |
| 102 | | 45 | | | | | 60 | | | |
| 103 | | | 45 | | | | | 60 | | |
| 104 | | | | 45 | | | | | 60 | |
| 105 | | | | | 45 | | | | | 60 |
| 106 | 45 | | | | | | 60 | | | |
| 107 | | 45 | | | | | | 60 | | |
| 108 | | | 45 | | | | | | 60 | |
| 109 | | | | 45 | | | | | | 60 |
| 110 | | | | | 45 | 60 | | | | |
| 111 | 45 | | | | | | | 60 | | |
| 112 | | 45 | | | | | | | 60 | |
| 113 | | | 45 | | | | | | | 60 |
| 114 | | | | 45 | | 60 | | | | |
| 115 | | | | | 45 | | 60 | | | |
| 116 | 45 | | | | | | | | 60 | |
| 117 | | 45 | | | | | | | | 60 |
| 118 | | | 45 | | | 60 | | | | |
| 119 | | | | 45 | | | 60 | | | |
| 120 | | | | | 45 | | | 60 | | |
| 121 | 45 | | | | | | | | | 60 |
| 122 | | 45 | | | | 60 | | | | |
| 123 | | | 45 | | | | 60 | | | |
| 124 | | | | 45 | | | | 60 | | |
| 125 | | | | | 45 | | | | 60 | |
| 126 | 45 | | | | | 65 | | | | |
| 127 | | 45 | | | | | 65 | | | |
| 128 | | | 45 | | | | | 65 | | |
| 129 | | | | 45 | | | | | 65 | |
| 130 | | | | | 45 | | | | | 65 |
| 131 | 45 | | | | | | 65 | | | |
| 132 | | 45 | | | | | | 65 | | |
| 133 | | | 45 | | | | | | 65 | |
| 134 | | | | 45 | | | | | | 65 |
| 135 | | | | | 45 | 65 | | | | |
| 136 | 45 | | | | | | | 65 | | |
| 137 | | 45 | | | | | | | 65 | |
| 138 | | | 45 | | | | | | | 65 |
| 139 | | | | 45 | | 65 | | | | |
| 140 | | | | | 45 | | 65 | | | |
| 141 | 45 | | | | | | | | 65 | |
| 142 | | 45 | | | | | | | | 65 |
| 143 | | | 45 | | | 65 | | | | |
| 144 | | | | 45 | | | 65 | | | |
| 145 | | | | | 45 | | | 65 | | |
| 146 | 45 | | | | | | | | | 65 |
| 147 | | 45 | | | | 65 | | | | |

TABLE 1-continued

| Target ID | 1st Labeling | | | | | 2nd Labeling | | | | |
|---|---|---|---|---|---|---|---|---|---|---|
| | FAM | HEX | ROX | Cy5 | 705 | FAM | HEX | ROX | Cy5 | 705 |
| 148 | | | 45 | | | | 65 | | | |
| 149 | | | | 45 | | | | 65 | | |
| 150 | | | | | 45 | | | | 65 | |
| 151 | 50 | | | | | 55 | | | | |
| 152 | | 50 | | | | 55 | | | | |
| 153 | | | 50 | | | | | 55 | | |
| 154 | | | | 50 | | | | | 55 | |
| 155 | | | | | 50 | | | | | 55 |
| 156 | 50 | | | | | | 55 | | | |
| 157 | | 50 | | | | | | 55 | | |
| 158 | | | 50 | | | | | | 55 | |
| 159 | | | | 50 | | | | | | 55 |
| 160 | | | | | 50 | 55 | | | | |
| 161 | 50 | | | | | | | 55 | | |
| 162 | | 50 | | | | | | | 55 | |
| 163 | | | 50 | | | | | | | 55 |
| 164 | | | | 50 | | 55 | | | | |
| 165 | | | | | 50 | | 55 | | | |
| 166 | 50 | | | | | | | | 55 | |
| 167 | | 50 | | | | | | | | 55 |
| 168 | | | 50 | | | 55 | | | | |
| 169 | | | | 50 | | | 55 | | | |
| 170 | | | | | 50 | | | 55 | | |
| 171 | 50 | | | | | | | | | 55 |
| 172 | | 50 | | | | 55 | | | | |
| 173 | | | 50 | | | | 55 | | | |
| 174 | | | | 50 | | | | 55 | | |
| 175 | | | | | 50 | | | | 55 | |
| 176 | 50 | | | | | 60 | | | | |
| 177 | | 50 | | | | | 60 | | | |
| 178 | | | 50 | | | | | 60 | | |
| 179 | | | | 50 | | | | | 60 | |
| 180 | | | | | 50 | | | | | 60 |
| 181 | 50 | | | | | | 60 | | | |
| 182 | | 50 | | | | | | 60 | | |
| 183 | | | 50 | | | | | | 60 | |
| 184 | | | | 50 | | | | | | 60 |
| 185 | | | | | 50 | 60 | | | | |
| 186 | 50 | | | | | | | 60 | | |
| 187 | | 50 | | | | | | | 60 | |
| 188 | | | 50 | | | | | | | 60 |
| 189 | | | | 50 | | 60 | | | | |
| 190 | | | | | 50 | 60 | | | | |
| 191 | 50 | | | | | | | | 60 | |
| 192 | | 50 | | | | | | | | 60 |
| 193 | | | 50 | | | 60 | | | | |
| 194 | | | | 50 | | | 60 | | | |
| 195 | | | | | 50 | | | 60 | | |
| 196 | 50 | | | | | | | | | 60 |
| 197 | | 50 | | | | 60 | | | | |
| 198 | | | 50 | | | | 60 | | | |
| 199 | | | | 50 | | | | 60 | | |
| 200 | | | | | 50 | | | | 60 | |
| 201 | 50 | | | | | 65 | | | | |
| 202 | | 50 | | | | | 65 | | | |
| 203 | | | 50 | | | | | 65 | | |
| 204 | | | | 50 | | | | | 65 | |
| 205 | | | | | 50 | | | | | 65 |
| 206 | 50 | | | | | | 65 | | | |
| 207 | | 50 | | | | | | 65 | | |
| 208 | | | 50 | | | | | | 65 | |
| 209 | | | | 50 | | | | | | 65 |
| 210 | | | | | 50 | 65 | | | | |
| 211 | 50 | | | | | | | 65 | | |
| 212 | | 50 | | | | | | | 65 | |
| 213 | | | 50 | | | | | | | 65 |
| 214 | | | | 50 | | 65 | | | | |
| 215 | | | | | 50 | | 65 | | | |
| 216 | 50 | | | | | | | | 65 | |
| 217 | | 50 | | | | | | | | 65 |
| 218 | | | 50 | | | 65 | | | | |
| 219 | | | | 50 | | | 65 | | | |
| 220 | | | | | 50 | | | 65 | | |
| 221 | 50 | | | | | | | | | 65 |
| 222 | | 50 | | | | 65 | | | | |
| 223 | | | 50 | | | 65 | | | | |

TABLE 1-continued

| Target | 1st Labeling | | | | | 2nd Labeling | | | | |
|---|---|---|---|---|---|---|---|---|---|---|
| ID | FAM | HEX | ROX | Cy5 | 705 | FAM | HEX | ROX | Cy5 | 705 |
| 224 | | | 50 | | | | | 65 | | |
| 225 | | | | 50 | | | | | 65 | |

According to another embodiment of the present application, when a nucleic acid complex pair is not used as a primer associated with the amplification product for the probe-binding domain PR to which the probe complex 200 binds, the number of targets (N1) from which the target nucleic acid sequences can be detected using the nucleic acid complex pair and the probe complex 200, may be (the number of targets from which the target nucleic acid sequences can be detected using the probe complex 200)+(the number of targets (N2) from which the target nucleic acid sequences can be detected using the nucleic acid complex pair) (see 19(b)).

In a more specific embodiment, when the temperatures of the dissociation peak values assigned to the first labeling method are 40° C., 45° C. and 50° C. and the temperatures of the dissociation peak values assigned to the second labeling method are 55° C., 60° C., and 65° C., and a total of 5 fluorescent wavelength bands (or fluorescent materials) can be detected, even if a nucleic acid complex pair is not used as a primer associated with the amplification product for the probe-binding domain PR to which the probe complex 200 binds, a total of 30 targets ((3*5)+(3*5)=30) can be detected by performing the detection of target nucleic acid sequences using the nucleic acid complex pair and the probe complex 200.

Until now, the designing and operations of the nucleic acid complex pair and the probe complex 20, which are used in one tube (or a unit cell) for the detection of target nucleic acid sequences in a sample, are explained.

Hereinafter, the methods for detection of target nucleic acid sequences using the probe complex 200, and the nucleic acid complex pair and the probe complex 200 according to some embodiments of the present application will be described specifically.

Figure 20:
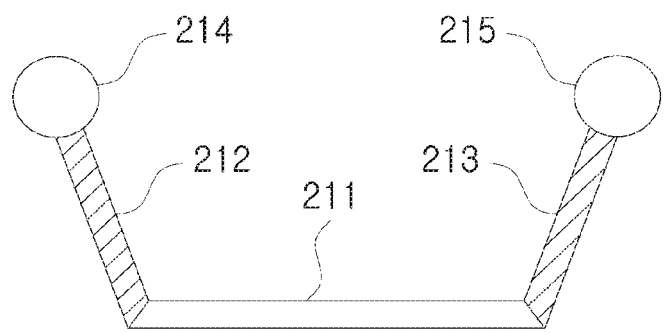
FIG. 20 shows a view illustrating a probe complex 210 according to the first embodiment of the present application.

2. Probe Complex 210 According to a First Embodiment 2.1 Probe Complex 210 According to a First Embodiment FIG. 20 shows a view illustrating a probe complex 210 according to the first embodiment of the present application.

The probe complex 210 according to the first embodiment of the present application may include a determination region 211, a first pairing region 212, a second pairing region 213, a first detection region 214 and the second detection region 215.

The determination region 211 may be linked to a first pairing region 212 and a second pairing region 213. The first pairing region 212 may be linked to one end of the determination region 211 and the second pairing region 213 may be linked to the other end of the determination region 211. The first detection region 214 may be linked to the first

TABLE 2

| Target | 1st Labeling | | | | | 2nd Labeling | | | | |
|---|---|---|---|---|---|---|---|---|---|---|
| ID | FAM | HEX | ROX | Cy5 | 705 | FAM | HEX | ROX | Cy5 | 705 |
| 1 | 40 | | | | | | | | | |
| 2 | | 40 | | | | | | | | |
| 3 | | | 40 | | | | | | | |
| 4 | | | | 40 | | | | | | |
| 5 | | | | | 40 | | | | | |
| 6 | 45 | | | | | | | | | |
| 7 | | 45 | | | | | | | | |
| 8 | | | 45 | | | | | | | |
| 9 | | | | 45 | | | | | | |
| 10 | | | | | 45 | | | | | |
| 11 | 50 | | | | | | | | | |
| 12 | | 50 | | | | | | | | |
| 13 | | | 50 | | | | | | | |
| 14 | | | | 50 | | | | | | |
| 15 | | | | | 50 | | | | | |
| 16 | | | | | | 55 | | | | |
| 17 | | | | | | | 55 | | | |
| 18 | | | | | | | | 55 | | |
| 19 | | | | | | | | | 55 | |
| 20 | | | | | | | | | | 55 |
| 21 | | | | | | 60 | | | | |
| 22 | | | | | | | 60 | | | |
| 23 | | | | | | | | 60 | | |
| 24 | | | | | | | | | 60 | |
| 25 | | | | | | | | | | 60 |
| 26 | | | | | | 65 | | | | |
| 27 | | | | | | | 65 | | | |
| 28 | | | | | | | | 65 | | |
| 29 | | | | | | | | | 65 | |
| 30 | | | | | | | | | | 65 | pairing region 212. The second detection region 215 may be linked to the second pairing region 213.

The determination region 211 may include a domain which complementarily binds to a different nucleic acid sequence. The determination region 211 may include a domain which specifically binds to the different nucleic acid sequence. What is meant by that the determination region 211 includes a domain which complementarily binds to a different nucleic acid sequence may be that at least a part of the domain of the determination region 211 have at least one property among the electrical, chemical, or physical properties that correspond to those of the different nucleic acid sequence, and is thus associated with the different nucleic acid sequence The determination region 211 may include at least one nucleic acid (or nucleic acid analogs). The at least one nucleic acid (or nucleic acid analogs) may consist of deoxyribonucleic acid (DNA), locked nucleic acid (LNA), peptide nucleic acid (PNA), hexose nucleic acid (HNA), and ribonucleic acid (RNA), or various nucleic acid analogs, or a combination thereof.

The determination region 211 may complementarily bind to a probe-binding domain PR. The determination region 211 may specifically bind to a probe-binding domain PR. As used herein, the term "probe-binding domain PR" may refer to a particular nucleic acid sequence, which has a nucleotide sequence that can complementarily bind to the determination region 211.

According to an embodiment of the present application, dissociation peak values may be determined based on the temperature at which the binding with the probe-binding domain PR is dissociated. The binding force between the determination region 211 and the probe-binding domain PR may be determined based on the types of nucleotides, nucleotide sequences, number of nucleotides, etc. and thus, dissociation peak values may be determined based on the types of nucleotides, nucleotide sequences, number of nucleotides, etc. used for the binding between the determination region 211 and the probe-binding domain PR.

The first pairing region 212 may bind to the second pairing region 213. The probe complex 210 according to an embodiment of the present application may be implemented such that the first pairing region 212 and the second pairing region 213 have a complementary binding to each other. The first pairing region 212 may include a nucleotide sequence which is complementary to at least a partial sequence of the second pairing region 213. The second pairing region 213 may include a nucleotide sequence which is complementary to at least a partial sequence of the first pairing region 212.

The first pairing region 212 and the second pairing region 213 may include at least one nucleic acid (or nucleic acid analogs). The at least one nucleic acid (or nucleic acid analogs) may consist of deoxyribonucleic acid (DNA), locked nucleic acid (LNA), peptide nucleic acid (PNA), hexose nucleic acid (HNA), and ribonucleic acid (RNA), or various nucleic acid analogs, or a combination thereof.

The first detection region 214 and the second detection region 215 may include an interactive domain. The first detection region 214 and the second detection region 215 may include a domain at which energy can be exchanged. In an embodiment, the first detection region 214 may include a domain that provides energy to the second detection region 215, and the second detection region 215 may include a domain at which the second detection region 215 receives energy from the first detection region 214.

The first detection region 214 and the second detection region 215 may properties which are different from each other. When the first detection region 214 and the second detection region 215 have an optical property, the optical property of the first detection region 214 may be different from that of the second detection region 215. In an embodiment, the wavelength band of light being released from the first detection region 214 may be different from that being released from the second detection region 215.

According to an embodiment of the present application, whether there is an interaction between the first detection region 214 and the second detection region 215 may be determined based on whether the first pairing region 212 and the second pairing region 213 are bound to each other.

Specifically, in case that the binding between the first determination region 211 and a probe-binding domain PR is dissociated, the first pairing region 212 and the second pairing region 213 may complementarily bind to each other by the self-aggregation of the probe complex 210. In case that the first pairing region 212 binds to the second pairing region 213, the distance between the first detection region 214 (which is linked to the first pairing region 212) and the second detection region 215 (which is linked to the second pairing region 213) become closer and thus an interaction may be possible.

When the second detection region 215 is positioned within an effective interactive distance (ID) of the first detection region 214 due to the binding between the first pairing region 212 and the second pairing region 213, the signals induced by a signal-generating material included in the first detection region 214 and/or the second detection region 215 may be changed. In an embodiment, the change in the detected signal may refer to a change in the wavelength band (e.g.; a wavelength band of light) of a signal detected from the second detection region 215.

2.2 Method for Detection of Presence of Target Nucleic Acid Using Probe Complex 210 According to the First Embodiment The probe complex 210 according to the first embodiment of the present application may be used in a PCR reaction for detecting a target nucleic acid sequence.

Specifically, the probe complex 210 according to the first embodiment of the present application may be contacted with a sample which is suspected as having a target nucleic acid sequence. A mixture solution containing the probe complex 210 and a sample may be provided. A part of an oligonucleotide associated with a target nucleic acid sequence within the mixture solution may be amplified by appropriately adjusting the temperature of the mixture solution. The oligonucleotide may be a target material containing a target nucleic acid sequence. With regard to the steps of a PCR reaction, a denaturation step, an annealing step, and an extension step may be performed sequentially. In the process of a PCR reaction, a denaturation step, an annealing step, and an extension step may be performed repeatedly.

For a mixture solution in which the amplification is completed, a step of detecting a melting curve may be performed. A dissociation peak value may be identified based on the melting curve. The dissociation peak value may be associated with the temperature at which the determination region 211 of the probe complex 210 is dissociated from the probe-binding domain PR The dissociation peak value may correspond to the temperature at which the determination region 211 of the probe complex 210 is dissociated from the probe-binding domain PR.

In detecting a plurality of types of target nucleic acid sequences using a plurality of types of the probe complex 210, a plurality of types of the probe complex 210 may be implemented by properly selecting the sequence of the probe-binding domain PR, which is targeted by the determination region 211, in considering the binding force between the determination region 211 and the probe-binding domain PR. As a result, the types of the target nucleic acid sequences in a sample can be confirmed by identifying the types of the probe complex 210 that correspond to the dissociation peak values which were confirmed by the above method. A target nucleic acid sequence may be a sequence corresponding to the probe-binding domain PR. The target nucleic acid sequence may be the same nucleic acid sequence that corresponds to the probe-binding domain PR.

In case that the unit nucleic acid of the determination region 211 of the probe complex 210 according to the first embodiment of the present application is PNA, the decomposition of the determination region 211 by the enzyme (e.g. polymerase), which is involved in the production of the amplification product with regard to oligonucleotides associated with a target nucleic acid sequence in the extension step, may not occur. This may be due to the relatively strong binding force of PNA. Alternatively, the strong biding force of PNA may be caused by a different structure of PNA from a structure of DNA.

However, in case that the unit nucleic acid of the determination region 211 of the probe complex 210 according to the first embodiment of the present application is DNA, the determination region 211 may be decomposed by the enzyme (e.g., polymerase), which is involved in the production of the amplification product with regard to oligonucleotides associated with a target nucleic acid sequence in the extension step. Accordingly, when the unit nucleic acid of the determination region 211 of the probe complex 210 is DNA, the above target detection method may not be performed.

To solve the problem, according to an embodiment of the present application, the probe complex 210 may comprise an enzyme for preventing the cleavage (decomposition) of the determination region 211 of the probe complex 210 by the above enzyme such as a polymerase in the extension step. The additional enzyme may be bound to the determination region 211 of the probe complex 210.

Alternatively, the cleavage of the determination region 211 of the probe complex 210 may be prevented by modifying the enzyme such as a polymerase. For example, at least some domains of the enzyme, which have a function to decompose the determination region 211 in extension step may be deactivated. In some embodiments, a a DNA polymerase which lacks the hydrolase activity may be used for PCR.

2.3 Method for Detecting Target Nucleic Acid Sequence Utilizing Probe Complex 210 and Nucleic Acid Complex Pair According to the First Embodiment For the detection of a target nucleic acid sequence using a probe complex 210 and a nucleic acid complex pair according to an embodiment of the present application, as explained in FIG. 6, a step of providing a mixture solution, a step of a PCR reaction, a step of stabilization, a step of melting curve detection, and a step of identifying peak detection values may be performed.

In the step of providing a mixture solution, at least one type of the probe complex 210 and at least one type of a nucleic acid complex pair may be provided.

When a plurality of types of a probe complex 210 are provided to the mixture solution, the plurality of types of a probe complex 210 may be designed such that the binding force between each of the determination region 211 of the probe complex 210 and the probe-binding domain PR is different from each other. In case that a plurality of types of a probe complex 210 are contained in the mixture solution, the plurality of types of a probe complex 210 may be designed such that the dissociation peak values based on the number of nucleotides, types of nucleotides, types of unit nucleic acids, etc. are different from each other.

In case that a plurality of types of a probe complex 210 are provided to the mixture solution, the plurality of types of a probe complex 210 may be designed such that the binding force between the first pairing region 112 and the second pairing region 122 is different from each other. When a plurality of types of a probe complex 210 are provided to the mixture solution, the plurality of types of a probe complex 210 may be designed such that dissociation peak values based on the number of nucleotides, types of nucleotides, types of unit nucleic acids, etc. are different from each other.

The mixture solution may be further provided with an enzyme, nucleotide fragments, co-enzyme, buffer, etc. The PCR kit that can be used in the step of providing a mixture solution may include at least one selected from the probe complex 210 according to the first embodiment, nucleic acid complex pair, enzyme used in a PCR reaction, nucleotide fragments, co-enzyme, buffer, etc.

A PCR kit may be implemented in a form where a composition containing at least one material (e.g., a nucleic acid complex pair) is contained in a container, and a plurality of containers in a single packed container to be sold. A PCR kit may be implemented in a form where a composition containing at least one material is contained in a container to be sold. A PCR kit may be implemented in a form where at least one material is included in a container in a dried state to be sold.

Figure 21:
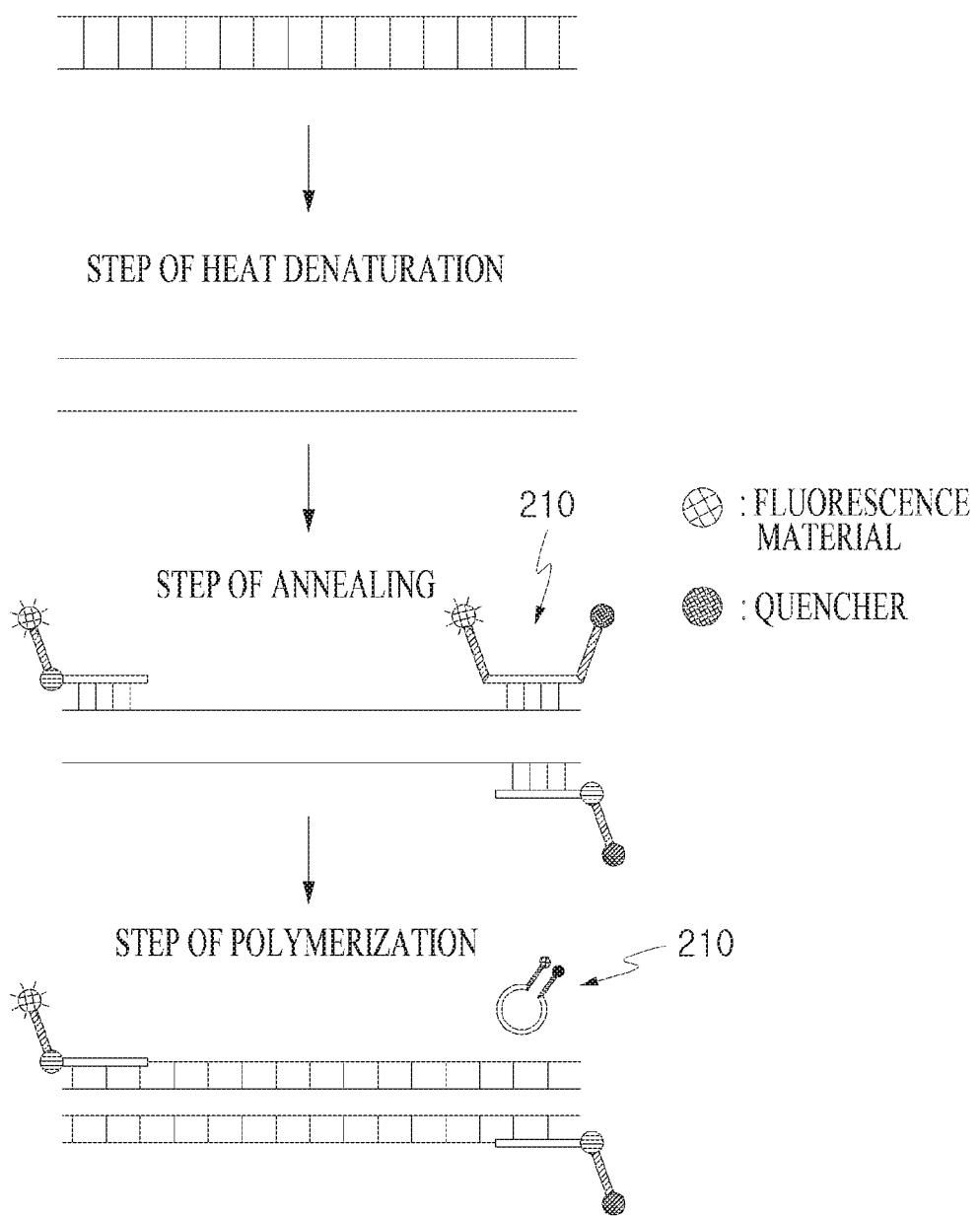
FIGS. 21 and 22 show views illustrating the procedures of a PCR reaction for a mixture solution containing a probe complex 210 and a nucleic acid complex pair according to an embodiment of the present application.
Figure 22:
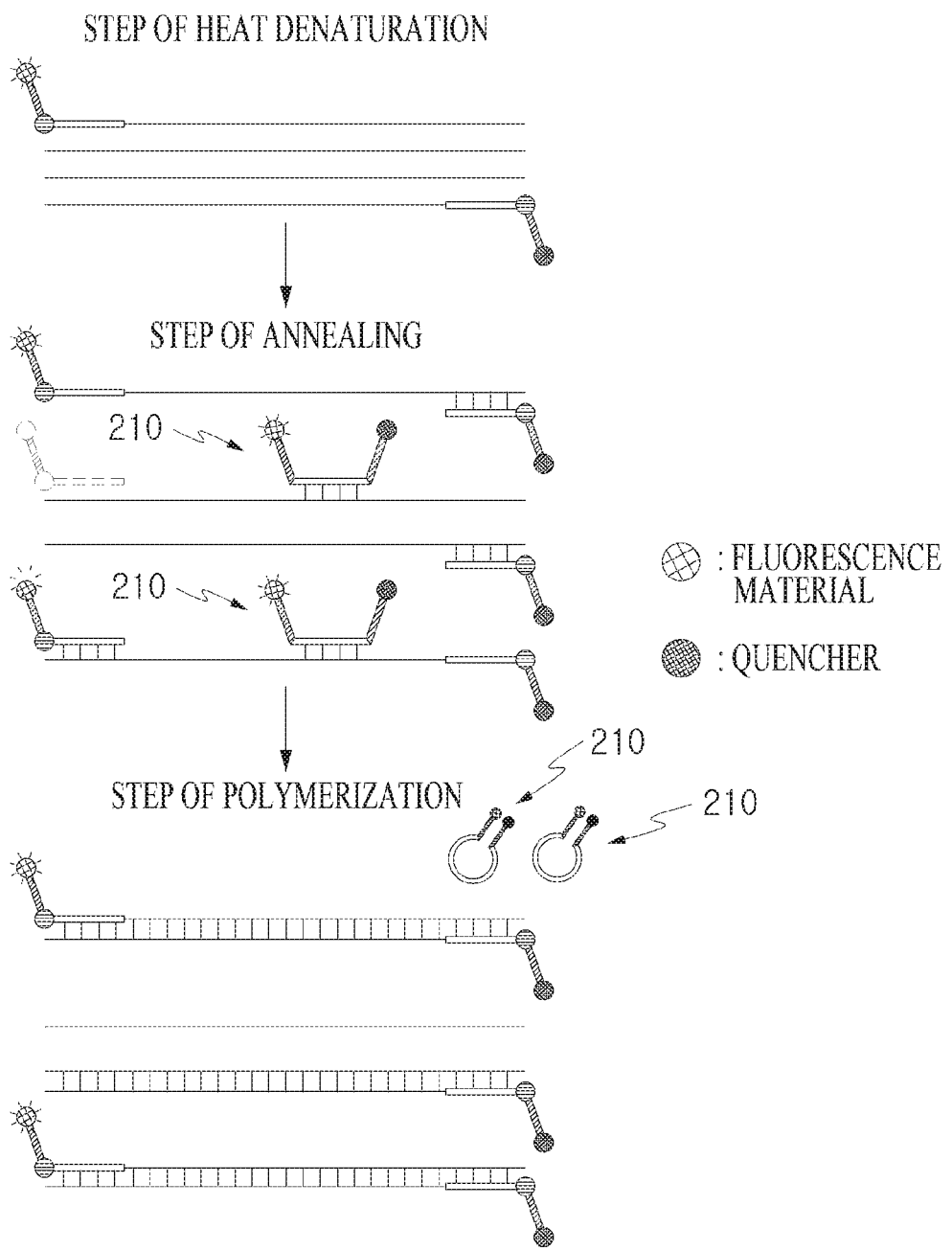

FIGS. 21 and 22 show views illustrating the procedures of a PCR reaction for a mixture solution containing a probe complex 210 and a nucleic acid complex pair according to an embodiment of the present application.

In proceeding a PCR reaction using the probe complex 210 and the nucleic acid complex pair according to an embodiment of the present application, the PCR reaction may be performed according to the Asymmetric PCR method. Herein below, the PCR reaction according to the Asymmetric PCR method will be explained. The mixture solution to perform the PCR reaction according to the Asymmetric PCR method may include a higher percentage of the first nucleic acid complex 110 compared to the second nucleic acid complex 120.

In the denaturation step, the double-stranded nucleic acid structure in a sample can be separated into a single-stranded nucleic acid structure by increasing the temperature of the mixture solution in which a sample, a probe complex 210, and a nucleic acid complex pair are contained. In particular, the double-stranded nucleic acid structure being separated may include a first target nucleic acid sequence TS1, a second target nucleic acid sequence TS2, and/or probe-binding domain PR.

In the annealing step, the first nucleic acid complex 110, the second nucleic acid complex 120 and/or the probe complex 210 may bind to at least a part of the single-stranded nucleic acid structure.

In the extension step, the amplification product for a target material TM, which includes a first target nucleic acid sequence TS1 or a second target nucleic acid sequence TS2, may be produced by having the first determination region 111 and/or the second determination region 121 as starting point. If the first determination region 111 or the second determination region 121 are used as primers associated with the probe complex 210, the probe complex 210 may be separated from the probe-binding domain PR by the production of an amplification product from the first determination region 111 or the second determination region 121. In other words, when the first determination region 111 or the second determination region 121 are used as primers associated with the probe complex 210, the probe complex 210 may be separated from the probe-binding domain PR at the time of producing the amplification product for the nucleic acid sequence, which is adjacent to a domain to which the probe complex 210 is bound, after the initiation of the production of the amplification product from the first determination region 111 or the second determination region 121.

In a denaturation step after one cycle of a PCR, the double-stranded nucleic acid structure in a mixture solution may be separated into a single-stranded nucleic acid structure. In particular, the double-stranded nucleic acid structure which includes at least one nucleic acid complex 100 formed during the extension step may be separated into a single-stranded nucleic acid structure.

In an annealing step after one cycle of a PCR, the first nucleic acid complex 110 or the second nucleic acid complex 120 may bind to the first target nucleic acid sequence TS1 and/or a second target nucleic acid sequence TS2 among the single-strands in the mixture solution. In particular, the second nucleic acid complex 120 may bind to the single-stranded nucleic acid structure where the first nucleic acid complex 110 is included. The first nucleic acid complex 110 of a nucleic acid complex pair may bind to the single-stranded nucleic acid structure including the second nucleic acid complex 120.

In an extension step after one cycle of a PCR, the amplification product for a target material TM including a first target nucleic acid sequence TS1 or a second target nucleic acid sequence TS2 may be produced by having the first determination region 111 or the second determination region 121 as a starting point. Likewise, when the first determination region 111 or the second determination region 121 are utilized as primers associated with the probe complex 210, the probe complex 210 may be separated from the probe-binding domain PR by the production of an amplification product from the first determination region 111 or the second determination region 121.

A mixture solution where the PCR reactions were performed at least twice may contain a nucleic acid structure which includes a first nucleic acid complex 110 and the second nucleic acid complex 120, a nucleic acid structure which includes a first nucleic acid complex 110, a nucleic acid structure which includes a second nucleic acid complex 120, and a nucleic acid structure which does not include a first nucleic acid complex 110 and a second nucleic acid complex 120.

However, since the ratio of the second nucleic acid complex 120 contained in the mixture solution is less than that of the first nucleic acid complex 110 (Asymmetric PCR method), a single-stranded nucleic acid structure to which a second nucleic acid complex 120 binds among the double-stranded nucleic acid structure including a first target nucleic acid sequence TS1 and/or a second target nucleic acid sequence TS2 remains as a single-stranded nucleic acid structure, without being amplified into a double-stranded nucleic acid structure.

Upon completion of a PCR reaction, a step of stabilization where the temperature of the mixture solution in which the PCR reaction is completed can be performed. In the step of stabilization, a probe complex 210 may bind to the remaining single-stranded nucleic acid structure which at least includes a second target nucleic acid sequence TS2. In the step of stabilization, a complementary binding between a first pairing region 112 and a second pairing region 122 of a nucleic acid structure including a first nucleic acid complex 110 and a second nucleic acid complex 120 may be performed.

After the step of stabilization, a step of melting curve detection for a mixture solution may be performed. Additionally, the identification of dissociation peak values based on the melting curve detection may be performed.

Figure 23:
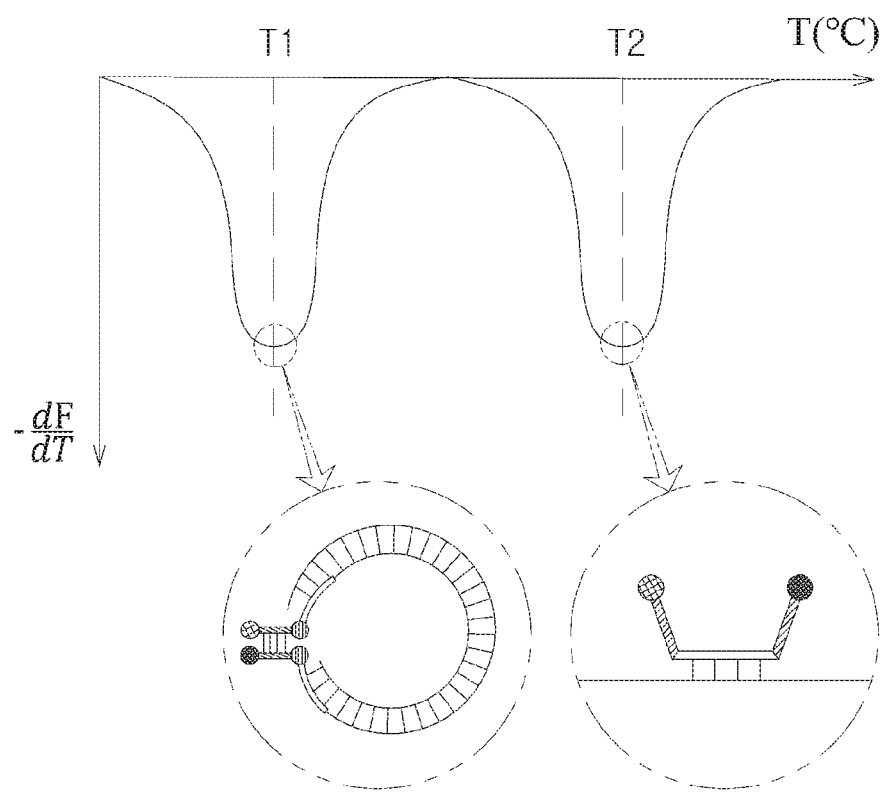
FIG. 23 shows a view illustrating the identified dissociation peak values of a mixture solution containing a probe complex 210 and a nucleic acid complex pair according to an embodiment of the present application.

According to an embodiment of the present application, in the differential curve graph based on the melting curve detection, a graph of the change in the amount of fluorescence with regard to the temperature where the maximum points at T1 and T2 temperatures are shown may be obtained (see FIG. 23). Alternatively, according to an embodiment of the present application, a graph of the change in the amount of fluorescence with regard to the temperature where the minimum points at T1 and T2 temperatures are shown may be obtained (see FIG. 23). Alternatively, according to an embodiment of the present application, a graph of the change in the amount of fluorescence with regard to the temperature where the maximum and minimum points at T1 and T2 temperatures are shown may be obtained (not shown).

In a specific embodiment. T1 where the maximum point (or minimum point) is shown in the differential melting curve may be a dissociation peak value associated with a nucleic acid complex pair. Here, the nucleic acid complex pair may be designed so as to perform the interaction of the signal extinction method. T2 where the maximum point (or minimum point) is shown in the differential melting curve may be a dissociation peak value associated with a complex probe 210. Here, the complex probe 220 may be designed so as to perform the interaction of the signal emission method.

In a more specific embodiment, with regard to the nucleic acid complex pair, a total of 15 different types of nucleic acid complex pairs, where dissociation peak values are assigned to 40° C., 45° C., or 50° C. and each of which is labeled with a total of 5 fluorescent materials, are designed and in connection with this, a total of 15 different types of probe complex 210, where dissociation peak values are assigned to 55° C., 60° C., or 65° C. and each of which is labeled with a total of 5 fluorescent materials, and the differential melting curve graph where a PCR reaction for a mixture solution containing the same was performed is the graph of FIG. 23, it can be confirmed that a target nucleic acid sequence corresponding to the Target ID 101 of Table 1 is present in the sample when T1 is FAM 45° C. and T2 is FAM 60° C.

Figure 24:
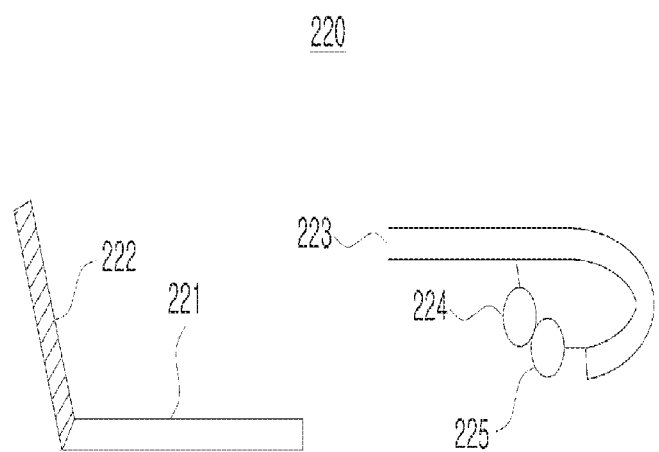
FIG. 24 shows views illustrating a probe complex 220 according to the second embodiment of the present application.

3. Probe Complex 220 According to a Second Embodiment and Method for Detecting Target Nucleic Acid Sequence Using the Same 3.1 Probe Complex 220 According to the Second Embodiment FIG. 24 shows views illustrating a probe complex 220 according to the second embodiment of the present application.

The probe complex 220 according to the second embodiment of the present application may comprise a first probe analog and a second probe analog, which are physically distinguished. The first probe analog may include a determination region 221 and a first pairing region 222. The first probe analog may be implemented in a form where the determination region 221 is linked to the first pairing region 222. The first probe analog may be implemented in a form where the first pairing region 222 is linked to the determination region 221. The second probe analog may include a second pairing region 223, a first detection region 224, and a second detection region 225. The second probe analog may be implemented in a form where a first detection region 224 and a second detection region 225 are linked to a second pairing region 223. The second probe analog may be implemented in a form where a first detection region 224 and a second detection region 225 are linked to a second pairing region 223.

The determination region 221 may include a domain which complementarily binds to a different nucleic acid sequence. The determination region 221 may include a domain which specifically binds to a different nucleic acid sequence. What is meant by that the determination region 221 includes a domain which complementarily binds to another nucleic acid sequence is that a part of the domain of the determination region 221 has at least one of the electrical, chemical, and physical properties, corresponding to that of the different nucleic acid sequence and is thus associated with the different nucleic acid sequence.

The determination region 221 may include at least one nucleic acid (or nucleic acid analogs). The at least one nucleic acid (or nucleic acid analogs) may consist of deoxyribonucleic acid (DNA), locked nucleic acid (LNA), peptide nucleic acid (PNA), hexose nucleic acid (HNA), and ribonucleic acid (RNA), or various nucleic acid analogs, or a combination thereof.

The determination region 221 may complementarily bind to a probe-binding domain PR The determination region 221 may specifically bind to a probe-binding domain PR. As used herein, the term "probe-binding domain PR" may refer to a particular nucleic acid sequence which has a nucleotide sequence that can complementarily bind to the determination region 221.

The first pairing region 222 may be separated from the determination region 221, when the amplification product for a target material TM containing the probe-binding domain PR is produced. The first pairing region 222 may be separated from the determination region 221, when the amplification product for a target material TM containing the probe-binding domain PR is initiated and proceeded to a domain adjacent to the probe-binding domain PR.

The first pairing region 222 may be separated from the determination region 221 by the action of an enzyme for polymerization (e.g.; polymerase). The first pairing region 222 may be cleaved and separated from the determination region 221. In an embodiment, the separation of the first pairing region 222 from the determination region 221 may be due to the activity of hydrolase for terminal nucleic acid of the polymerase.

The first pairing region 222 may bind to at least a part of the second pairing region 223. A probe complex 200 according to an embodiment of the present application may be implemented such that the first pairing region 222 and the second pairing region 223 form a complementary binding. The first pairing region 222 may include a nucleotide sequence which is complementary to the second pairing region 223. The second pairing region 223 may include a nucleotide sequence which is complementary to the first pairing region 222.

The first pairing region 222 may bind to the second pairing region 223 and thereby perform a function of a primer. In other words, when the first pairing region 222 binds to at least a part of the second pairing region 223, an amplification product for the second pairing region 223 may be produced by having the first pairing region 222 as a starting point.

The first pairing region 222 and the second pairing region 223 may include at least one nucleic acid (or nucleic acid analogs). The at least one nucleic acid (or nucleic acid analogs) may consist of deoxyribonucleic acid (DNA), locked nucleic acid (LNA), peptide nucleic acid (PNA), hexose nucleic acid (HNA), and ribonucleic acid (RNA), or various nucleic acid analogs, or a combination thereof.

The first detection region 224 and the second detection region 225 may include an interactive domain. The first detection region 224 and the second detection region 225 may include a domain for energy exchange. In an embodiment, the first detection region 224 may include a domain which provides energy to the second detection region 225, and the second detection region 225 may include a domain at which the second detection region 225 receives energy from the first detection region 224.

The first detection region 224 and the second detection region 225 may have a different property from each other. When the first detection region 224 and the second detection region 225 have an optical property, the optical property of the first detection region 224 may be different from that of the second detection region 225. In an embodiment, the wavelength band of light released from the first detection region 224 may be different from the wavelength band of light released from the second detection region 225.

According to an embodiment of the present application, in case that the second pairing region 223 is not in a self-aggregation state and the second pairing region 223 binds to the first pairing region 222, the distance between the first detection region 224 and the second detection region 225 may be far enough such that the interactions of the first detection region 224 and the second detection region cannot be occurred.

Accordingly, with regard to the probe complex 220 according to an embodiment of the present application, the interaction between the first detection region 224 and the second detection region 225 may be determined based on the presence of the production of an amplification product for the second pairing region 223.

Specifically, in case that the second pairing region 223 is a single-stranded oligonucleotide, the distance between the first detection region 224 and the second detection region 225 may become adjacent to each other due to self-aggregation. If the amplification is proceeding, the first pairing region 222 may be bound to the second pairing region 223 so that the first pairing region 222 and the second pairing region 223 may form double strands. As a result, the self-aggregation of the second pairing region is dissociated and the distance between the first detection region 224 and the second detection region 225 may be spaced apart from each other such that the interaction between the first detection region 224 and the second detection region 225 cannot be occurred.

When the amplification product for the second pairing region 223 is produced and thereby the first detection region 224 and the second detection region 225 are separated farther than the effective interactive distance (ID), detection signals due to signal-generation materials included in the first detection region 224 and/or a second detection region 225 may be changed. In an embodiment, the change of signals may refer to a change of the wavelength band (e.g.; a wavelength band of light) of a signal from the first detection region 224 and the second detection region 225.

3.2 Method for Detecting Target Nucleic Acid Sequence Using Probe Complex 220 According to the Second Embodiment The probe complex 220 according to the second embodiment of the present application may be used in a PCR reaction and thereby used for detecting a target nucleic acid sequence.

Specifically, the probe complex 220 according to the second embodiment may be contacted with a sample which is suspected of having a target nucleic acid sequence. A mixture solution containing a probe complex 220 and a sample may be provided. A part of the oligonucleotide associated with the target nucleic acid sequence in mixture solution may be amplified by appropriately adjusting the temperature of the mixture solution. The oligonucleotide may be a target material which contains the target nucleic acid sequence.

In the step of amplifying the oligonucleotide, the first pairing region 222 of the first probe analog bound to the probe-binding domain PR may be separated when it comes near to the time for producing the amplification product for the target material including the probe-binding domain PR.

Then, in an annealing step of a subsequent cycle, the first pairing region 222 may bind to the second pairing region 223, and in the extension step, an amplification product for the second pairing region 223 may be produced. The amplification product for the second pairing region 223 means a double stranded nucleic acid formed by binding the single-stranded first pairing region 222 and the single stranded second pairing region 223. With regard to the steps of a PCR reaction, a denaturation step, an annealing step, and an extension step may be performed sequentially. In the process of a PCR reaction, a denaturation step, an annealing step, and an extension step may be performed repeatedly.

For a mixture solution in which the amplification is completed, a step of detecting a melting curve may be performed. A dissociation peak value may be detected based on the melting curve. The dissociation peak value may be associated with the temperature at which the binding between the first pairing region 222 and the second pairing region 223 is dissociated.

In the detection of a plurality of types of a target nucleic acid sequence using a plurality of types of a probe complex 220, a plurality of types of a probe complex 220 may be implemented by adjusting the length of the second pairing region 223 and nucleotide sequence. As a result, the types of target nucleic acid sequences present in a sample can be confirmed by confirming the type of the probe complex 220 that corresponds to the dissociation peak value confirmed by the above method. The target nucleic acid sequence may be a sequence corresponding to the determination region 221. The target nucleic acid sequence may be a sequence corresponding to the probe-binding domain PR The target nucleic acid sequence may be the same sequence that corresponds to the probe-binding domain PR.

3.3 Probe Complex 220 According to the Second Embodiment and Method for Detecting Target Nucleic Acid Sequence Using Nucleic Acid Complex Pair For the detection of a target nucleic acid sequence using a probe complex 220 and a nucleic acid complex pair according to an embodiment of the present application, as explained in FIG. 6, a step of providing a mixture solution, a step of a PCR reaction, a step of stabilization, a step of melting curve detection, and a step of identifying peak detection values may be performed.

In the step of providing a mixture solution, at least one type of the probe complex 220 and at least one type of a nucleic acid complex pair may be provided.

When a plurality of types of a probe complex 220 are provided to the mixture solution, the plurality of types of the probe complex 220 may be designed such that the binding force between each of the second paring region 223 and the first pairing region 222 is different from each other. When a plurality of types of a probe complex 220 are provided to the mixture solution, the plurality of types of the probe complex 220 may be designed such that the dissociation peak values based on the number of nucleotides, types of nucleotides, types of unit nucleic acids, etc. are different from each other.

When a plurality of types of nucleic acid complex pairs are provided to a mixture solution, the plurality of types of nucleic acid complex pairs may be designed such that the binding force between the first pairing region 112 and the second pairing region 122 may be different from each other. When the plurality of types of nucleic acid complex pairs are provided to a mixture solution, the plurality of types of nucleic acid complex pairs may be designed such that the dissociation peak values based on the number of nucleotides, types of nucleotides, types of unit nucleic acids, etc. of the first pairing region 112 and the second pairing region 122 are different from each other.

A mixture solution may be further provided with an enzyme, nucleotide fragments, co-enzyme, buffer, etc. The PCR kit to be used in the step of providing the mixture solution may include at least one among the probe complex 220 according to the second embodiment, a nucleic acid complex pair, an enzyme used in a PCR reaction, an enzyme, nucleotide fragments, co-enzyme, buffer, etc.

The PCR kit according to an embodiment of the present application may include at least one among the probe complex 210 according to the first embodiment, the probe complex 220 according to the second embodiment, a nucleic acid complex pair, an enzyme used in a PCR reaction, an enzyme, nucleotide fragments, co-enzyme, buffer, etc. In an embodiment, when a device can measure a total of 6 dissociation peak values, the PCR kit may include two types of the probe complex 210 according to the first embodiment to which each of two dissociation peak values corresponds, two types of the probe complex 220 according to the second embodiment to which each of two dissociation peak values corresponds, and two types of then nucleic acid complex pairs to which each of two dissociation peak values corresponds.

Figure 25:
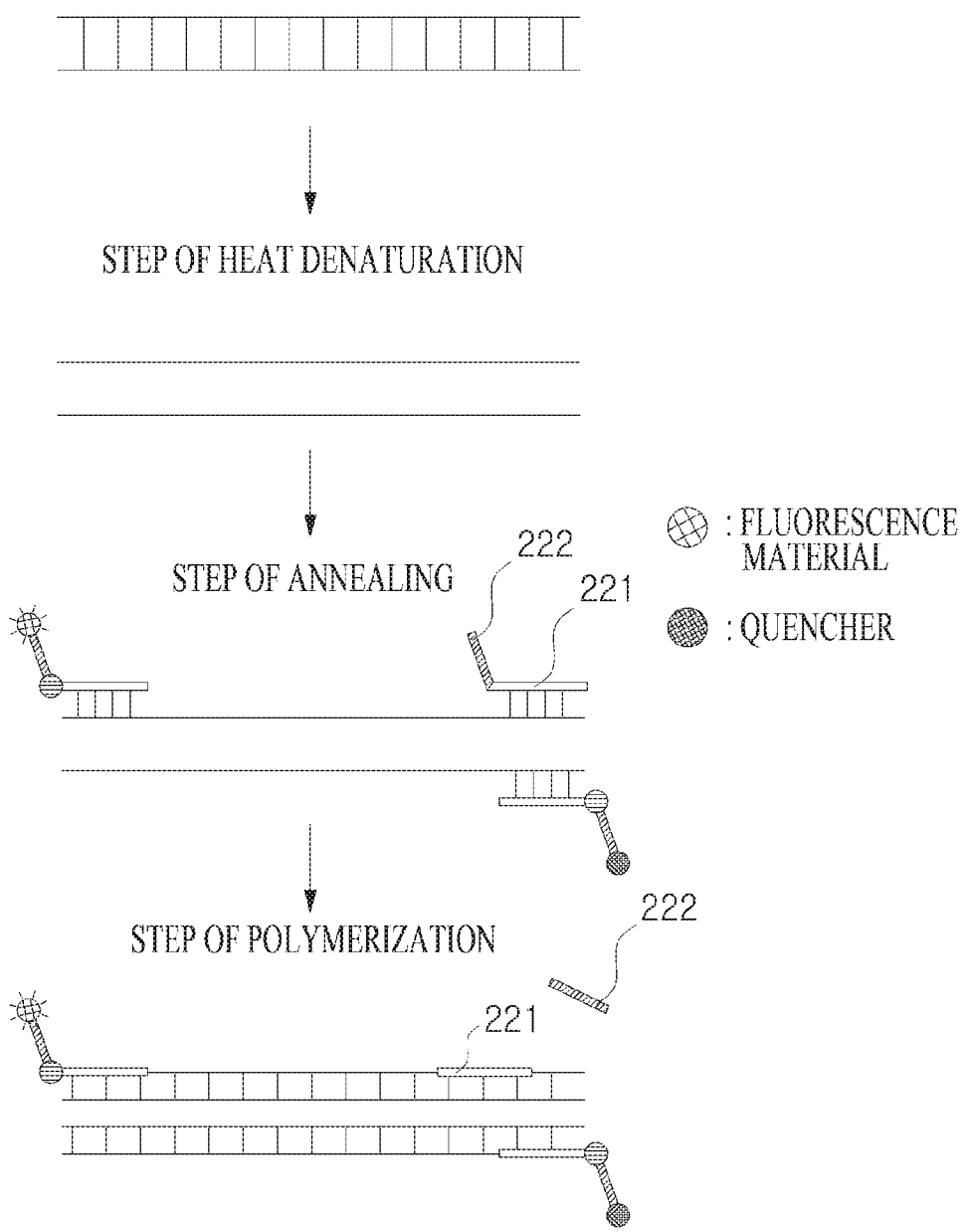
FIGS. 25 and 26 show views illustrating the procedures of a PCR reaction for a mixture solution containing a probe complex and a nucleic acid complex pair according to an embodiment of the present application.
Figure 26:
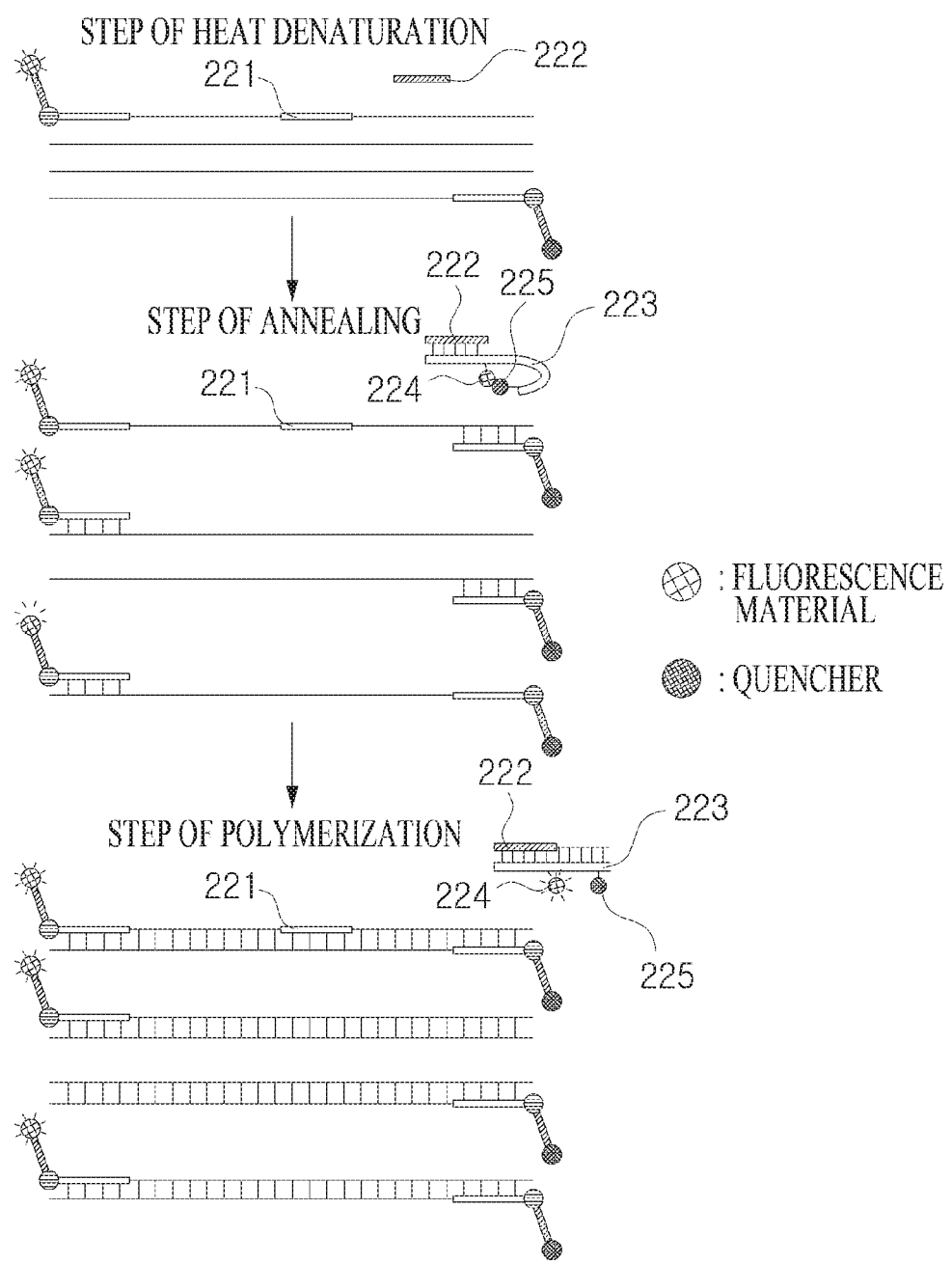

FIGS. 25 and 26 show views illustrating the procedures of a PCR reaction for a mixture solution containing a probe complex and a nucleic acid complex pair according to an embodiment of the present application.

According to an embodiment of the present application, in performing a PCR reaction using the probe complex 220 and a nucleic acid complex pair, the PCR reaction may be proceeded according to the Asymmetric PCR method. Alternatively, the PCR reaction may be proceeded according to the Symmetric PCR method. Herein below, the PCR reaction according to the Symmetric PCR method will be explained. The mixture solution to perform the PCR reaction according to the Symmetric PCR method may include an almost the same amount of the first nucleic acid complex 110 compared to the second nucleic acid complex 120. Preferably, the mixture solution to perform a PCR reaction according to the Symmetric PCR method may contain the first nucleic acid complex 110 and the second nucleic acid complex 120 in a 1:1 ratio.

In the denaturation step, the double-stranded nucleic acid structure in a sample can be denatured into a single-stranded nucleic acid structure by increasing the temperature of the mixture solution in which a sample, a probe complex 220, and a nucleic acid complex pair are contained. In particular, the double-stranded nucleic acid structure may include a first target nucleic acid sequence TS1, a second target nucleic acid sequence TS2, and/or probe-binding domain PR.

In the annealing step, the first nucleic acid complex 110, the second nucleic acid complex 120 and/or the probe complex 220 may bind to at least a part of the single-stranded nucleic acid structure. In the annealing step, the first nucleic acid complex 110, the second nucleic acid complex 120 and/or a first probe analog of the probe complex 220 may bind to at least a part of the single-stranded nucleic acid structure.

In the extension step, the amplification product for a target material TM, which includes a first target nucleic acid sequence TS1 or a second target nucleic acid sequence TS2, may be produced by having the first determination region 111 and/or the second determination region 121 as starting point. If the first determination region 111 or the second determination region 121 are utilized as primers associated with the probe complex 220, a part of the probe complex 220 may be separated from the probe-binding domain PR by the production of an amplification product from the first determination region 111 or the second determination region 121. In other words, when the first determination region 111 or the second determination region 121 are used as primers associated with the probe complex 220, a part of the probe complex 220 may be separated from the probe-binding domain PR at the time of producing the amplification product for the nucleic acid sequence, which is adjacent to a domain to which the probe complex 220 is bound, after the initiation of the production of the amplification product from the first determination region 111 or the second determination region 121.

With regard to the production of an amplification product from the first determination region 111 or the second determination region 121, a part of the first probe analog of the probe complex 220 may be spaced apart from the probe-binding domain PR. With regard to the production of an amplification product from the first determination region 111 or the second determination region 121, a first pairing region 222 of the first probe analog of the probe complex 220 may be separated from the determination region 221. With regard to the production of an amplification product from the first determination region 11 or the second determination region 121, a first pairing region 222 of the first probe analog of the probe complex 220 may be cleaved and separated from the determination region 221.

In a denaturation step after one cycle of a PCR, the double-stranded nucleic acid structure in a mixture solution may be separated into a single-stranded nucleic acid structure. In particular, the double-stranded nucleic acid structure which includes at least one nucleic acid complex 100 formed during the extension step may be separated into a single-stranded nucleic acid structure.

The first pairing region 222 may be fluidized in a mixture solution. The first pairing region 222 separated from the determination region 221 may be fluidized in a mixture solution.

In an annealing step after one cycle of a PCR, the first nucleic acid complex 110 or the second nucleic acid complex 120 may bind to the first target nucleic acid sequence TS1 and/or a second target nucleic acid sequence TS2 among the single-strands in the mixture solution. In particular, the second nucleic acid complex 120 may bind to the single-stranded nucleic acid structure where the first nucleic acid complex 110 is included. The first nucleic acid complex 110 of a nucleic acid complex pair may bind to the single-stranded nucleic acid structure including the second nucleic acid complex 120.

The first pairing region 222 may bind to a second probe analog of the probe complex 220. The first pairing region 222 which was fluidized within the mixture solution may bind to the second pairing region 223 of a second probe analog of the probe complex 220. Once the first pairing region 222 binds to the second pairing region 223, the first pairing region 222 can function as a primer.

In an extension step after one cycle of a PCR the amplification product for a target material TM including a first target nucleic acid sequence TS1 or a second target nucleic acid sequence TS2 may be produced by having the first determination region 111 or the second determination region 121 as a starting point. Additionally, in an extension step after one cycle of a PCR, the second pairing region 223 bound to the first pairing region 222 may be amplified. In other words, the amplification product for the second pairing region 223 bound to the first pairing region 222 may be amplified.

A mixture solution where the PCR reactions were performed at least twice may contain a nucleic acid structure which includes a first nucleic acid complex 110 and the second nucleic acid complex 120, a nucleic acid structure which includes a first nucleic acid complex 110, a nucleic acid structure which includes a second nucleic acid complex 120, a nucleic acid structure which does not include a first nucleic acid complex 110 and a second nucleic acid complex 120, and a nucleic acid structure which includes a first pairing region 222 and a second pairing region 223.

Upon completion of a PCR reaction, a step of stabilization where the temperature of the mixture solution in which the PCR reaction is completed can be performed. In the step of stabilization, a complementary binding between a first pairing region 112 and a second pairing region 122 of a nucleic acid structure including a first nucleic acid complex 110 and a second nucleic acid complex 120 may be performed.

After the step of stabilization, a step of melting curve detection for a mixture solution may be performed. Additionally, the identification of dissociation peak values based on the melting curve detection may be performed.

According to an embodiment of the present application, in the differential curve graph based on the melting curve detection, a graph of the change in the amount of fluorescence with regard to the temperature where the maximum points at T1 and T2 temperatures are shown may be obtained (not shown). Alternatively, according to an embodiment of the present application, in the differential curve graph based on the melting curve detection, a graph of the change in the amount of fluorescence with regard to the temperature where the minimum points at T1 and T2 temperatures are shown may be obtained (not shown). Alternatively, according to an embodiment of the present application, according to an embodiment of the present application, in the differential curve graph based on the melting curve detection, a graph of the change in the amount of fluorescence with regard to the temperature where the maximum point is shown at one of T1 and T2 temperatures and the minimum point is shown at one of T1 and T2 temperatures may be obtained (FIG. 27).

Figure 27:
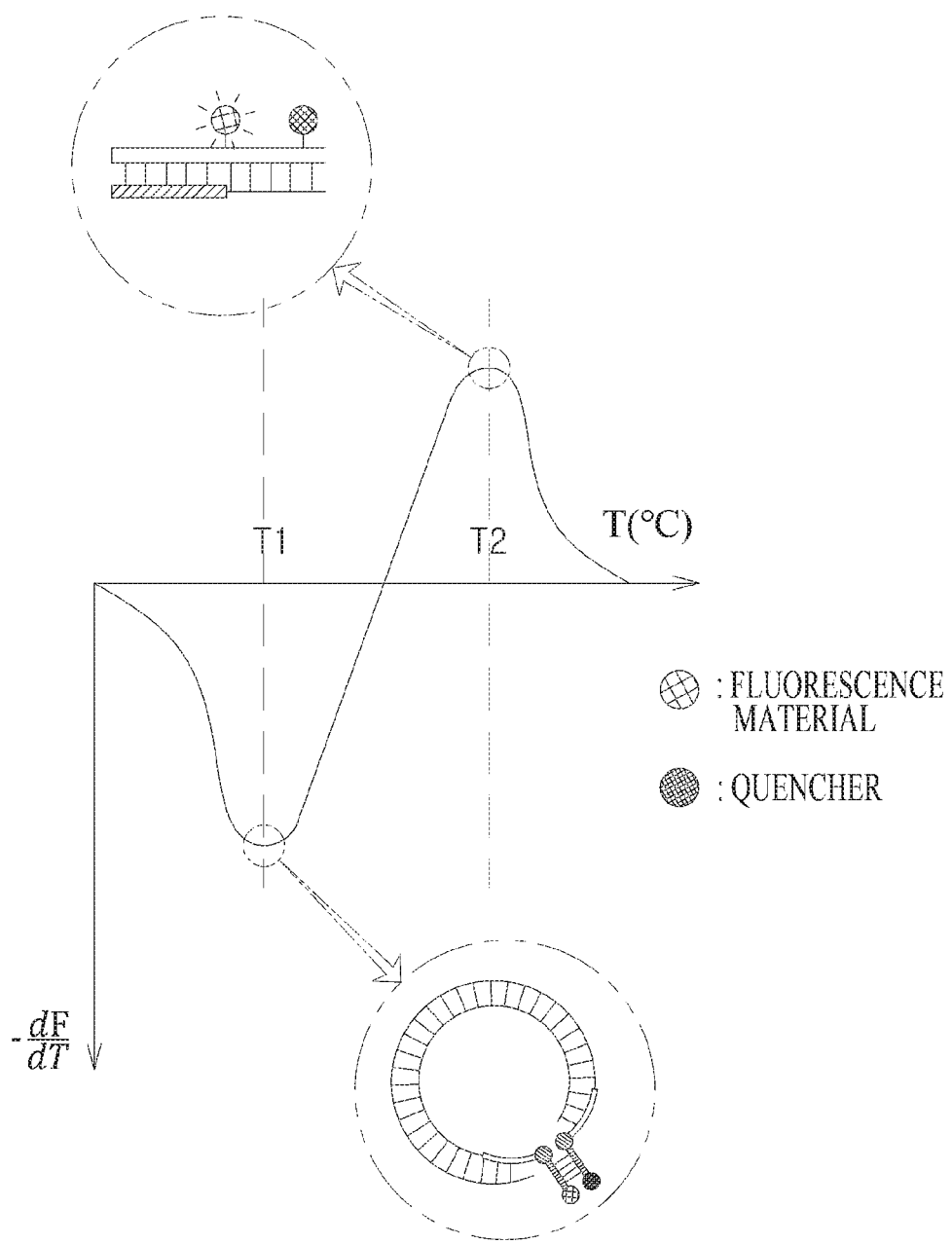
FIG. 27 shows a view illustrating the identified dissociation peak values of a mixture solution containing a probe complex 220 and a nucleic acid complex pair according to an embodiment of the present application.

In a more specific embodiment, referring to FIG. 27, T1, where the maximum point is shown in the differential melting curve may be a dissociation peak value associated with a nucleic acid complex pair. The nucleic acid complex pair at this time may be designed to perform an interaction of the signal extinction method. T2, where the minimum point is shown in the differential melting curve, may be a dissociation peak value associated with the complex probe 220. The complex probe 220 at this time may be designed to perform an interaction of the signal extinction method.

While the present invention has been described referring to exemplary embodiments and accompanying drawings, it will be understood by those skilled in the art that the present invention is not limited to these exemplary embodiments and drawings, but various changes in form and details may be made therein without departing from the spirit and scope of the invention. In addition, these embodiments described herein may not be limitedly applied, but all or some of the embodiments may be selectively combined so that various modifications can be made. Further, the steps constituting each embodiment can be used individually or in combination with the steps constituting other embodiments.

Hereinafter, the present invention will be described in more detail through experimental examples. It should be apparent to those skilled in the art that these examples are for illustrative purposes only and that the scope of the present invention is not construed as being limited by these examples.

Figure 28:
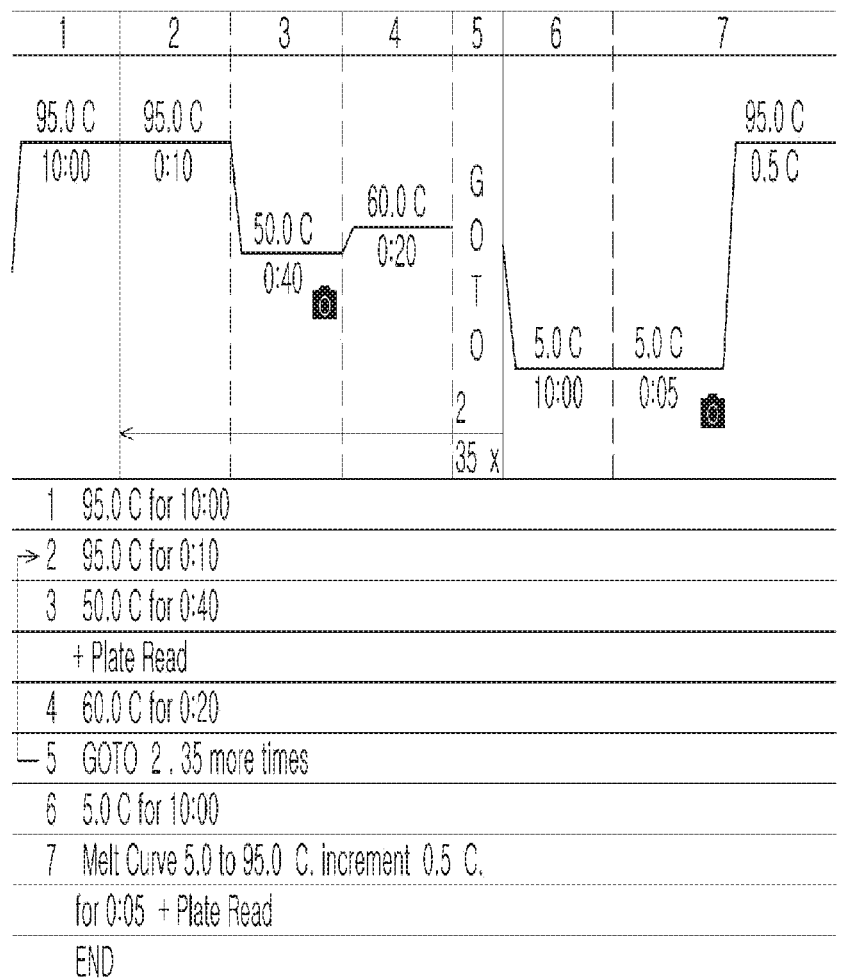
FIG. 28 shows a view illustrating the PCR process to perform a conventional probe/primer based target detection method, and temperature change conditions for melting temperature analysis, and PCR conditions according to an embodiment of the present application.

<Experimental the First Embodiment> Multi-Target Detection Using Conventional Probes and Pimers A target gene was amplified using a primer in a conventional manner, and then a multi-target detection method was performed using a target specific probe based on a melting temperature analysis method. PCR was performed based on the primer and probe as shown in Table 3 below as described in FIG. 28 and the melting temperature analysis was performed.

Figure 29:
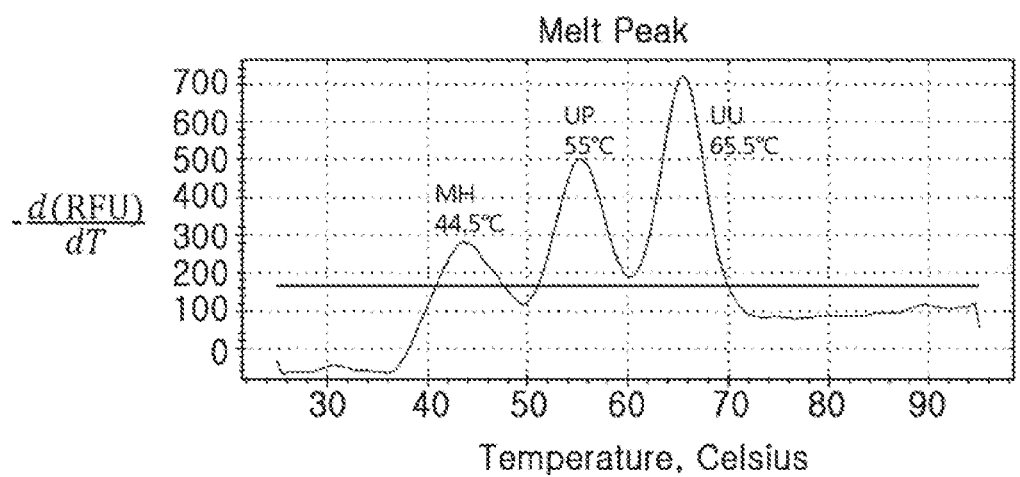
FIG. 29 shows a view illustrating the results of dissociation peak values of 3 types of targets in one sample according to an embodiment of the present application.

As a result, it was confirmed that the melting temperature appeared at desired points, as shown in FIG. 29.

TABLE 3

| target | primer_probe | Seq ID NO. | Sequence | Tm (° C.) |
|---|---|---|---|---|
| Mycoplasm hominis | MH MH_F | 1 | AGCTCCTATTGCCACGTA | 44.5 |
|  | MH_R | 2 | GTGTGGAGCATCTTGTAATC |  |
|  | MH_probe | 3 | CACTCATATACAGC |  |
| Ureaplasma urealyticum | UU UU_F | 4 | TGAAGTTGAAGCAAATGCACG | 65.5 |
|  | UU_R | 5 | TCTGAAGTTTTACCATCAACTGC |  |
|  | UU_probe | 6 | ACTACGCAATCATCAGCCAAAGC |  |
| Ureaplasma parvum | UP UP_F | 7 | GAAACTCTGCGACTCCAAATTTA | 35 |
|  | UP_R | 8 | AGAAGCTGATTGTTCTAGTCAAT |  |
|  | UP_probe | 9 | TTCTAAATCATTAAAATCAACAGC |  |

<Experimental the Second Embodiment> Multi-Target Detection Wing Nucleic Acid Complex of the Preesent Invention In a nucleic acid complex according to the present invention, in order to confirm the difference in the melting conventional temperature effect of according to the nucleotide sequence of the pairing regions, a nucleic acid complex which was prepared by varying the nucleotide constitution of pairing regions by applying the technique of the present invention to a nucleic acid primer for detection of HPV16, as shown in Table 4.

Figure 30:
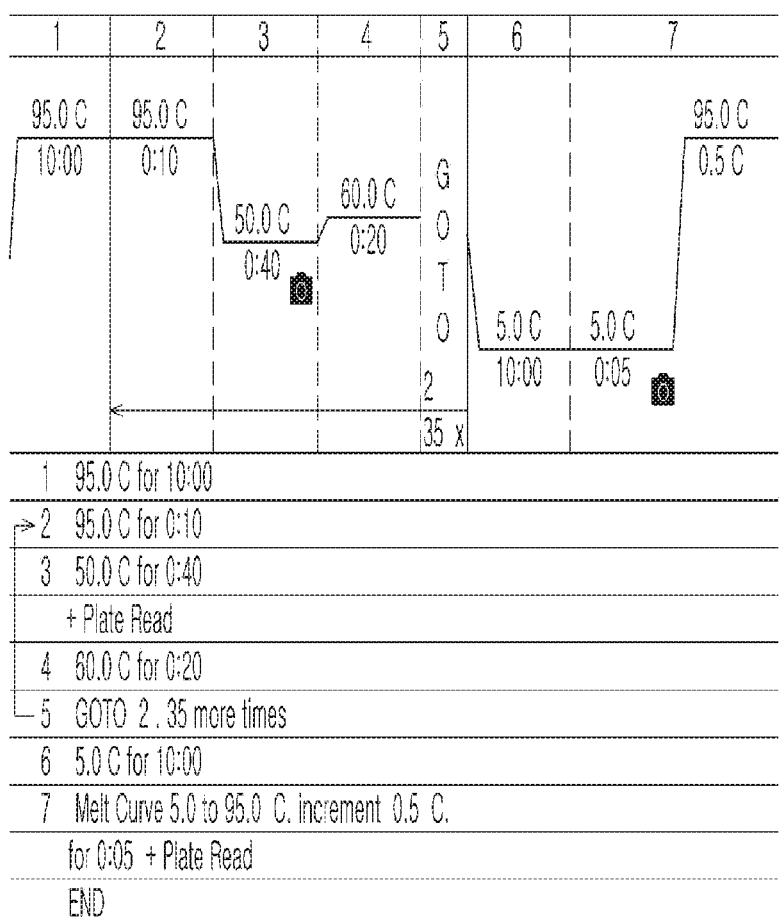
FIG. 30 shows a view illustrating the PCR conditions to perform a target detection method using a nucleic acid complex, and temperature change conditions for melting temperature analysis, and PCR conditions according to an embodiment of the present application

The nucleic acid complex pair was mixed with a target sample using the method of FIG. 30, followed by a PCR reaction, and the fusion temperature analysis was performed.

Figure 31:
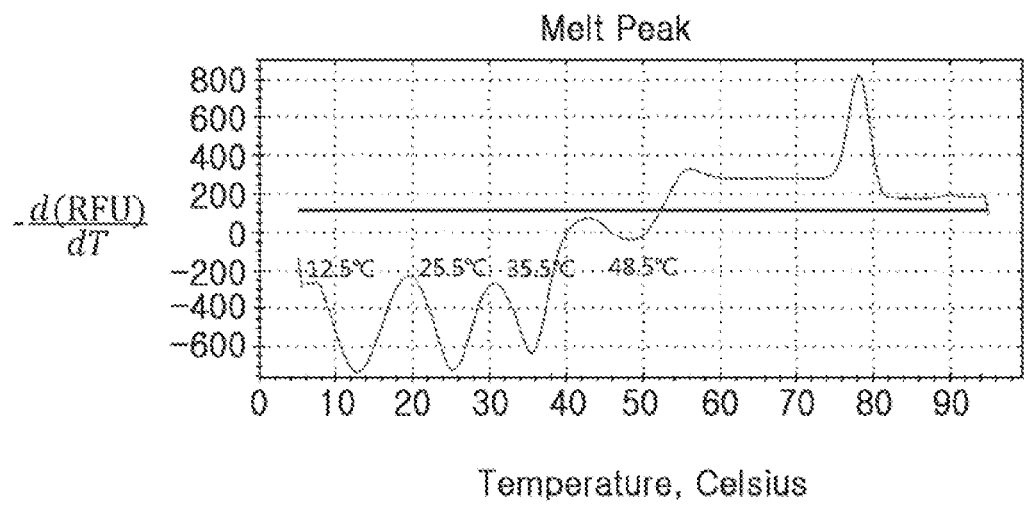
FIG. 31 shows a view illustrating the results of dissociation peak values of various types of targets in one sample according to an embodiment of the present application.

As a result, it was confirmed that the targets can be detected at various temperatures by controlling the compositions of the nucleotide sequences of the pairing regions as shown in FIG. 31.

Therefore, since the melting temperatures of the primers and probes used in Experimental Examples 1 and 2 are different from each other, these nucleic acid complexes can be simultaneously used for the detection of samples, and this indicates that a total of 7 types of samples can be detected with one fluorescent dye in one tube.

TABLE 41

| GCAT % | Mer | Seq ID No. | sequence | Tm (° C.) |
|---|---|---|---|---|
| GC 100% | 8 | 10 & 11 | /5IABkFQ/ CCCGCGCG/iSp18/TGGAGATACACCTACATTG | 48.5 |
| | | 12 & 13 | /56-FAM/ CGCGCGGG/iSp18/GCTGGACCATCTATTTCATC | |
| AT 100% | 8 | 14 & 11 | /5IABkFQ/ AAAAAAAA/iSp18/TGGAGATACACCTACATTG | 12.5 |
| | | 15 & 13 | /56-FAM/ TTTTTTTT/iSp18/GCTGGACCATCTATTTCATC | |
| AT 100% | 10 | 16 & 11 | /5IABkFQ/ AAAAAAAAAA/iSp18/TGGAGATACACCTACATTG | 25.5 |
| | | 17 & 13 | /56-FAM/ TTTTTTTTTT/iSp18/GCTGGACCATCTATTTCATC | |
| GC 50% | 10 | 18 & 11 | /5IABkFQ/ AACCTTGGGA/iSp18/TGGAGATACACCTACATTG | 35.5 |
| | | 19 & 13 | /56-FAM/ TCCCAAGGTT/iSp18/GCTGGACCATCTATTTCATC | |

In Table 4 above, iSP18 represents a blocking region.

What is claimed is:

1. A nucleic acid complex pair used for detecting target DNA in a sample, the nucleic acid complex pair comprising:
   a first nucleic acid complex including a first determination region, a first pairing region, and a first detection region, and
   a second nucleic acid complex including a second determination region, a second pairing region, and a second detection region,
      wherein the first determination region comprises a forward primer corresponding to a first sequence of the target DNA,
      wherein the second determination region comprises a reverse primer corresponding to a second sequence of the target DNA,
      wherein at least a part of the first pairing region and at least a part of the second pairing region are configured to complementarily bind to each other, and
      wherein one of the first detection region and the second detection region comprises a signal material generating a detectable signal, and the other of the first detection region and the second detection region comprises a quenching material absorbing at least some of the detectable signal when the first detection region and the second detection region are located within an effective interactive distance,
   wherein the target DNA consists of a first strand and a second strand,
   wherein the first sequence is located in the first strand of the target DNA,
   wherein the second sequence is located in the second strand of the target DNA, and
   wherein a distance between the first sequence and the second sequence of the target DNA is longer than the effective interactive distance.

2. The nucleic acid complex pair of claim 1,
   wherein the forward primer includes at least one of deoxyribonucleic acid (DNA), peptide nucleic acid (PNA), locked nucleic acid (LNA), hexose nucleic acid (HNA), and ribonucleic acid (RNA), and
   wherein the reverse primer includes at least one of deoxyribonucleic acid (DNA), peptide nucleic acid (PNA), locked nucleic acid (LNA), hexose nucleic acid (HNA), and ribonucleic acid (RNA).

3. The nucleic acid complex pair of claim 1,
   wherein when the first detection region comprises the signal material, the second detection region comprises the quenching material absorbing at least some of the detectable signal generated from the first detection region; and
   when the second detection region comprises the signal material, the first detection region comprises the quenching material absorbing at least some of the detectable signal generated from the second detection region.

4. The nucleic acid complex pair of claim 3,
   wherein a property of a signal detected from the first detection region and the second detection region is regulated based on whether the at least a part of the first pairing region and the at least a part of the second pairing region are complementarily bound to each other.

5. The nucleic acid complex pair of claim 1,
   wherein the first nucleic acid complex comprises a first blocking region for preventing a generation of an amplification product for the first pairing region, and the second nucleic acid complex comprises a second blocking region for preventing a generation of an amplification product for the second pairing region.

6. The nucleic acid complex pair of claim 5,
   wherein the first blocking region is positioned between the first determination region and the first detection region, and the second blocking region is positioned between the second determination region and the second detection region.

7. The nucleic acid complex pair of claim 1, wherein the at least a part of the first pairing region and the at least a part of the second pairing region are complementarily bound.

8. The nucleic acid complex pair of claim 1, wherein the distance between the first sequence and the second sequence of the target DNA is defined as a number of base pairs between the first sequence and the second sequence of the target DNA.

9. A PCR kit comprising the nucleic acid complex pair of claim 1 and an enzyme involved in a PCR reaction.

10. A method for detecting a target DNA in a sample, the method comprising:
   (a) providing a mixture solution comprising a sample and at least one nucleic acid complex pair,
   wherein the nucleic acid complex pair comprises a first nucleic acid complex and a second nucleic acid complex,
   wherein the first nucleic acid complex comprises a first determination region comprising a forward primer corresponding to the target DNA,
   wherein the second nucleic acid complex comprises a second determination region comprising a reverse primer corresponding to the target DNA,
   wherein at least a part of a first pairing region of the first nucleic acid complex and at least a part of a second pairing region of the second nucleic acid complex are configured to complementarily hybridize to each other, and
   wherein an intensity of a signal detected from a first detection region of the first nucleic acid complex and a second detection region of the second nucleic acid complex is regulated based on whether the at least a part of the first pairing region and the at least a part of the second pairing region are complementarily bound to each other;
   (b) amplifying at least a part of the target DNA by cyclic heating of the mixture solution such that an amplification product for at least a part of the target DNA is produced,
   wherein the amplification product includes a double-stranded region where the first determination region is incorporated in one strand and the second determination region is incorporated in the other strand, and
   wherein the first pairing region exists as a single strand at one end of the amplification product and the second pairing region exists as a single strand at the other end of the amplification product after the amplifying; and
   (c) detecting a signal from the mixture solution comprising the target DNA and the amplification product, wherein detecting the signal from the mixture solution comprises:
   detecting the signal from the mixture solution at a first temperature; and
   detecting the signal from the mixture solution at a second temperature,
   wherein the first temperature is lower than a dissociation temperature of the first pairing region and the second pairing region,
   wherein the second temperature is higher than the dissociation temperature of the first pairing region and the second pairing region, and
   wherein the dissociation temperature of the first pairing region and the second pairing region is related to a temperature at which a complementary binding between the at least a part of the first pairing region and the at least a part of the second pairing region is released.

11. The method of claim 10, wherein the first nucleic acid complex further comprises a first blocking region for preventing generation of an amplification product for the first pairing region, in which the first blocking region is positioned between the first determination region and the first detection region, and
   wherein the second nucleic acid complex further comprises a second blocking region for preventing generation of an amplification product for the second pairing region, in which the second blocking region is positioned between the second determination region and the second detection region.

12. The method of claim 10, the method further comprising, after the amplifying, lowering the temperature of the mixture solution below at least 40° C. for inducing the complementary binding between the at least a part of the first pairing region and the at least a part of the second pairing region.

13. The method of claim 10, the method further comprising, after the detecting the signal, identifying a dissociation peak value related to the dissociation temperature of the first pairing region and the second pairing region based on the detected signal in order to detect the target DNA in the sample.

14. The method of claim 10, wherein, during the provision of a mixture solution, at least a part of the first pairing region and a part of the second pairing region are complementarily bound.

15. The method of claim 10, wherein the amplification of at least a part of the target DNA comprises:
   heat-denaturing the target DNA and the amplification product for at least a part of the target DNA into a single strand;
   annealing the first determination region to a part of the target DNA;
   annealing the second determination region to the other part of the target DNA; and
   extending the DNA so as to produce the amplification product for at least a part of the target DNA.

16. The method of claim 15, wherein, in the amplification of at least a part of the target DNA, heat denaturing, annealing, and extending DNA are sequentially performed at least twice.

17. The method of claim 16, wherein the annealing of the first determination region and the annealing of the second determination region are performed simultaneously.

* * * * *